(12) United States Patent
Parker et al.

(10) Patent No.: US 7,482,119 B2
(45) Date of Patent: *Jan. 27, 2009

(54) SOLID PHASE METHODS FOR POLYNUCLEOTIDE PRODUCTION

(75) Inventors: Hsing-Yeh Parker, Woodinville, WA (US); John T. Mulligan, Seattle, WA (US)

(73) Assignee: Blue Heron Biotechnology, Inc., Bothell, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/965,018

(22) Filed: Oct. 13, 2004

(65) Prior Publication Data

US 2005/0106606 A1    May 19, 2005

Related U.S. Application Data

(63) Continuation-in-part of application No. 10/405,907, filed on Apr. 1, 2003, now abandoned.

(60) Provisional application No. 60/512,141, filed on Oct. 16, 2003, provisional application No. 60/511,770, filed on Oct. 15, 2003, provisional application No. 60/390,522, filed on Jun. 20, 2002, provisional application No. 60/369,478, filed on Apr. 1, 2002.

(51) Int. Cl.
*C12Q 1/68* (2006.01)
*C12P 19/34* (2006.01)
*C07H 21/04* (2006.01)

(52) U.S. Cl. .................. 435/6; 435/91.2; 435/91.15; 536/25.3; 536/25.4

(58) Field of Classification Search .............. 435/6, 435/91.2, 91.15, 91.1; 536/25.3, 25.4; 935/77, 935/78
See application file for complete search history.

(56) References Cited

U.S. PATENT DOCUMENTS

| 5,437,979 | A | | 8/1995 | Rampal et al. ............ 435/6 |
| 5,705,344 | A | | 1/1998 | Giordano et al. |
| 5,942,609 | A | | 8/1999 | Hunkapiller et al. ....... 536/25.3 |
| 6,048,734 | A | * | 4/2000 | Burns et al. ............ 436/180 |
| 6,277,622 | B1 | * | 8/2001 | Weiss ................... 435/252.3 |
| 6,670,127 | B2 | * | 12/2003 | Evans ..................... 435/6 |

OTHER PUBLICATIONS

Beattie et al. Solid-Phase gene Assembly, Nature, 1991, vol. 352(8).*
Beattie et al., "Gene synthesis Technology: Recent Developments and Future Prospects," *Biotechnology and Applied Biochemistry 10*: 510-521, Dec. 1988.
Beattie et al., "Solid-phase gene assembly," *Nature 352*: 548-549, Aug. 8, 1991. Also correction in *Nature 352*: 742, Aug. 22, 1991.
Correction, *Nature 352*:742, Aug. 22, 1991.

Constans, A., "Innovation in magnetic particle technology advance many fields," *The Scientist* 14(13): 23-EOA, Jun. 26, 2000. Also available at www.the-scientist.com.
Dietrich et al., "Gene assembly based on blunt-ended double-stranded DNA-modules," *Biotechnology Techniques* 12(1): 49-54, Jan. 1998.
Dombrowski et al., "Construction of a multiple mucin tandem repeat with a mutation in the tumor-specific epitope by a solid-phase gene assembly protocol," *Nucleic Acids Research* 20(24): 6743-6744, Dec. 25, 1992.
Gait, M.J. et al. "Rapid synthesis of oligodeoxyribonucleotides: a new solid-phase method," *Nucleic Acids Research* 4(4): 1135-1158, Apr. 1977.
Ghosh et al., "Covalent attachment of oligonucleotides to solid supports," *Nucleic Acids Research* 15(13): 5353-5372, Jul. 10, 1987.
Hostomský et al., "Solid-phase assembly of DNA duplexes from synthetic oligonucleotides," *Nucleic Acids Research Symposium Series 18*: 241-244, 1987.
Hostomský et al., "Solid-phase assembly of cow colostrum trypsin inhibitor gene," *Nucleic Acids Research* 15(12): 4849-4856, Jun. 25, 1987.
Hultman, T. et al., "Solid phase in vitro mutagenesis using plasmid DNA template," *Nucleic Acids Research* 18(17): 5107-5112, Sep. 11, 1990.
Jerala et al., "Regen: program for designing gene assembly," *Nucleic Acids Research* 16(5): 1759-1766, Mar. 11, 1988.
Joos et al., "Covalent Attachment of Hybridizable Oligonucleotides to Glass Supports," *Analytical Biochemistry* 247: 96-101, Apr. 5, 1997.
Kato et al., "A Method to Construct a Gene That Encodes a Repetitive Amino Acid Sequence by Polymerase Chain Reaction," *Analytical Biochemistry* 220: 428-429, Apr. 1, 1994.

(Continued)

*Primary Examiner*—Kenneth R. Horlick
*Assistant Examiner*—Joyce Tung
(74) *Attorney, Agent, or Firm*—Seed IP Law Group PLLC

(57) ABSTRACT

Polynucleotides having in excess of 1,000 nucleotides can be prepared using a solid phase synthesis technique. A feature of the technique is the use of a reusable solid support that contains covalently bound oligonucleotide. This covalently bound oligonucleotide is annealed to a bridge oligonucleotide, where the bridge is also annealed to a first oligonucleotide that forms a portion of the target polynucleotide. After the target polynucleotide is synthesized, it can be removed from the solid support under denaturing conditions, and the solid support re-used to prepare additional target polynucleotides. The yield of the target polynucleotide increases when shearing force is applied to the solid support that is linked to the growing oligonucleotide. This shearing force is thought to extend the growing end of the oligonucleotide away from contact with other oligonucleotide bound to the solid support and make that end more accessible to annealing with solution oligonucleotide. The synthesis is conveniently accomplished on a porous frit, where reagents and washing solutions are pumped through the frit.

6 Claims, 25 Drawing Sheets

OTHER PUBLICATIONS

Lohrmann, R. et al., "New Solid Supports for DNA Synthesis," *Fourth Annual Congress for Recombinant DNA Research*.

Makarova, K.S. et al., "DIROM—An Interactive System for Planning Experiments on Directed Mutagenesis and Construction of Artificial Genes," *Molecular Biology 26*: 72-80, 1992.

Maskos et al., "Oligonucleotide hybridisations on glass supports: A novel linker for oligonucleotide synthesis and hybridisation properties of oligonucleotide synthesised in situ," *Nucleic Acids Research 20*(7): 1679-1684, Apr. 11, 1992.

Mosaic Technologies, *Acrydite™: Technical Summary*, Mosaic Technologies, Inc., Boston, MA, Jan. 1998.

Nilsson et al., "Real-Time Monitoring of DNA Manipulations Using Biosensor Technology," *Analytical Biochemisty 224*: 400-408, Jan. 1, 1995.

Pachuk et al., "Chain reaction cloning: a one-step method for directional ligation of multiple DNA fragments," *Gene 243*: 19-25, 2000.

Rosenblum et al, "Amino Acid Sequence Analysis, Gene Construction, Cloning, and Expression of Gelnin, a Toxin Derived form *Gelonium multiflorum*," *Journal of Interferon and Cytokine Research 15*:547-555, Jun. 1995.

Schmitz et al., "Solid-Phase Enzymatic Synthesis of Oligonucleotides," *Organic Letters 1*(11): 1729-1731, 1999.

Soper et al., "Sanger DNA-Sequencing Reactions Performed in a Solid-Phase Nanoreactor Directly Coupled to Capillary Gel Electrophoresis," *Analytical Chemistry 70*: 4036-4043, Oct. 1, 1998.

Stahl et al., "Solid-Phase Genes Assembly of Constructs Derived from the *Plasmodium falciparum* Malaria Blood-Stage Antigen Ag332," *BioTechniques 14*(3): 424-434, Mar. 1993.

Van Ness et al., "A versatile solid support system for oligodeoxynucleotide probe-based hybridization assay," *Nucleic Acids Research 19*(12): 3345-3350, Jun. 25, 1991.

Walsh et al., "Optimizing the immobilization of single-stranded DNA onto glass beads," *Journal of Biochem. Biophys. Methods 47*: 221-231, 2001.

Wolf et al., "Rapid hybridization kinetics of DNA attached to submicron latex particles," *Nucleic Acids Research 15*(7): 2911-2926, Apr. 10, 1987.

Zhang et al., "A Solid-Support Methodology for the Construction of Geometrical Objects from DNA," *J. Am. Chem. Soc. 114*: 2656-2663, Mar. 25, 1992.

Zhang et al., "Single-base mutational analysis of cancer and genetic diseases using membrane bound modified oligonucleotides," *Nucleic Acids Rsearch 19*(14): 3929-3933, 1991.

* cited by examiner

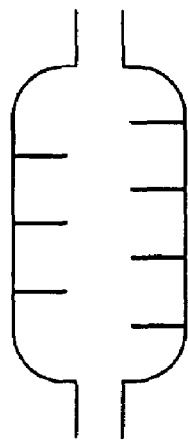
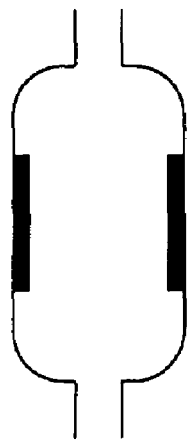
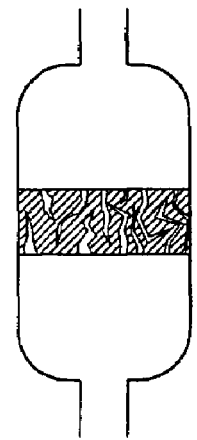
FIG. 5A　　　　FIG. 5B　　　　FIG. 5C
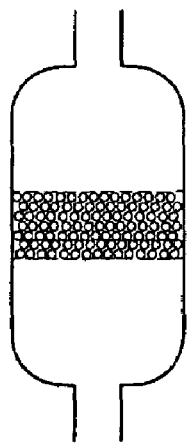
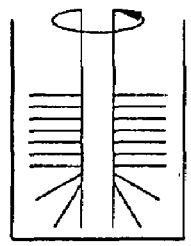
FIG. 5D　　　　FIG. 5E

CTTTC
CTTTC
FIG. 12A
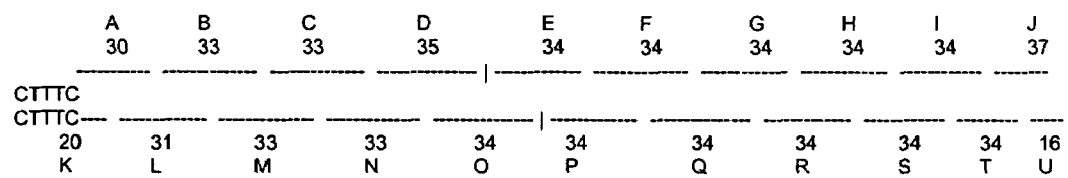
FIG. 12B
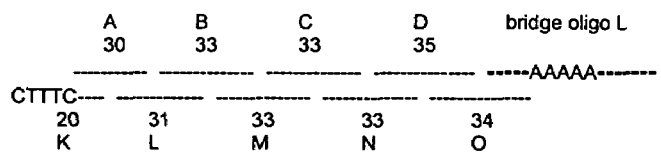
FIG. 12C
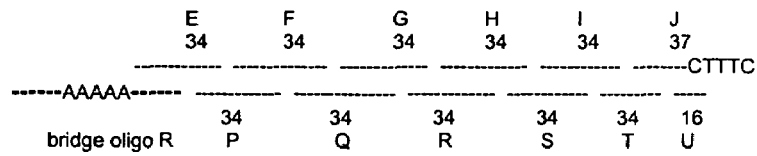
FIG. 12D

Lane: 1 2 3 4

Lane: 1 2 3 4

FIG. 13A
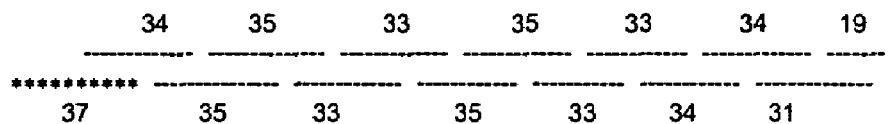
FIG. 13B
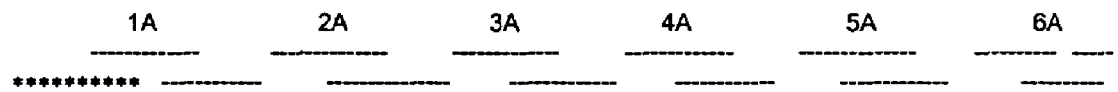
FIG. 13C

| 1A | 2A | 3A | 4A | 5A | 6A |
| 7A | 8A | 9A | 10A | 11A | 12A |

FIG. 17C

SOLID PHASE METHODS FOR POLYNUCLEOTIDE PRODUCTION

CROSS-REFERENCES TO RELATED APPLICATIONS

This application claims the benefit of U.S. Provisional Patent Application No. 60/512,141, filed Oct. 16, 2003; and U.S. Provisional Patent Application No. 60/511,770, filed Oct. 15, 2003, which are both incorporated herein by reference in their entireties. This application is also a continuation-in-part of U.S. patent application Ser. No. 10/405,907, filed Apr. 1, 2003, which is incorporated herein by reference in its entirety and which claims the benefit of U.S. Provisional Patent Application No. 60/369,478, filed Apr. 1, 2002 and U.S. Provisional Application No. 60/390,522, filed Jun. 20, 2002, which are both incorporated herein by reference in their entireties.

BACKGROUND OF THE INVENTION

1. Field of the Invention

The present invention relates to the synthesis of polynucleotides using solid phase synthesis techniques.

2. Description of the Related Art

A polynucleotide is a linear chain of nucleotides, where nucleotides are composed of a sugar, a base and a phosphate. The sugar of one nucleotide joins to the phosphate of the adjacent nucleotide in order to form the chain. A human gene is formed from a polynucleotide wherein the sugar is deoxyribose, and the base at each position in the chain is selected from adenine (A), cytosine (C), guanine (G) and thymine (T). Thus, the only chemical difference between links in a chain of polynucleotides is the base present in the link. In large part, genes differ from one another due to their different chain lengths and due to having a different sequence of the four bases along the chain.

Much of the discovery research in pharmaceutical companies is focused on genes, either as targets for drug development or as protein therapeutics. Due to recent and continuing efforts directed to determining the sequence of genomic DNA molecules, these companies have access to the base sequence a majority of the human genes. In fact, these companies are overwhelmed with potential opportunities, acutely aware that their competitors are looking at the same set of possibilities, and currently unable to work on more than a fraction of the genes that have been identified.

One of the major bottlenecks in performing research in the area of genes is the time and effort required to prepare genes of a desired base sequence which can be used, e.g., as a research or diagnostic tool, or a potential therapeutic agent. Genes are typically several hundred to a few thousand nucleotides long, and are defined by their nucleotide sequence. In order to successfully prepare a gene, the nucleotides of the gene must be in a precisely specified order, i.e., when a particular one of the four bases is specified to be at a particular location along the chain, then that base and no other base must be present at that particular location—there cannot be any extra or missing nucleotide bases.

The manufacture of short chains of nucleotides, often referred to as oligonucleotides when the chains are less than about 100 nucleotides in length, is a well developed and commercially employed process. Typically, an insoluble support is joined to a first nucleotide, and the support is placed into a solution with a reactive precursor of the second nucleotide. After the second nucleotide has been joined to the first nucleotide, the reaction mixture is washed through a frit, thus separating the solid support from any unreactive precursor. The solid phase containing the nascent oligonucleotide is then exposed to the reactive precursor of the third nucleotide, and this procedure is followed repetitively until the desired oligonucleotide is prepared.

Not all of the nascent oligonucleotide reacts as desired with a reactive precursor, and so even though the chemical yield is typically greater than 90%, the yield of desired product, based on the amount of first nucleotide bound to solid support, drops dramatically as the number of repetitive cycles increases. Also, it is empirically observed that some oligonucleotides made by this process, even when they contain the desired number of nucleotides, do not have precisely the desired base sequence. Perhaps a particular nucleotide precursor will occasionally react twice with a growing chain, or perhaps all of a particular nucleotide precursor is not washed away after a round of reaction and remains to compete with the next addition of nucleotide precursor. In any event, this approach to making polynucleotides has not proved effective at making chains of defined sequence having over about 100 nucleotides in length. See the following references for discussion of making oligonucleotides: Schmitz, C. and Reetz, M. T., *Org. Lett.* 1(11):1729-1731 (1999);

In part because genes are such a desirable research tool, and even potential therapeutic agents, several research groups have directed attention to finding ways to prepare polynucleotides, and particularly genes, having many hundred bases in a pre-defined sequence, and have published results from their studies. See, e.g., Pachuk, C. J. et al., *Gene* 243:19-25 (2000); Evans, G. A., PCT International Publication No. WO99/14318 (1999): Hunkapiller, M. W. et al., U.S. Pat. No. 5,942,609 issued August 1999; Dietrich, R. et al., *Biotech. Tech.* 12(1):49-54 (1998); Rosenblum, M. G. et al., *J. Interferon and Cytokine Res.* 15:547-555 (1995); Kato, T. et al., *Anal. Biochem.* 220:428-429 (1994); Ståhl, S. et al. *BioTechniques* 14(3):424-434 (1993); Dombrowski, K. E. and Wright, S. E., *Nucl. Acids Res.* 20(24):6743-6744 (1992); Makarova, K. S. et al. *Mol. Bio. (Mosk)* 26(1):93-103 (1992); Beattie, K. L. and Fowler, R. F., Nature 352:548-549, 742 (1991); Filippov, S. A. et al., *Bioorg. Khim.* 16(8):1045-1051 (1990); Beattie, K. L. et al., *Biotechnol. Appl. Biochem.* 10:510-521 (1988); and Jerala R. and Turk V, *Nuc. Acids Res.* 16(5):1759-1766 (1988); Hostomsk?, Z. et al., *Nuc. Acids Res.* 15(12):4849-4856 (1987).

Each of the approaches described in these publications has strengths and weaknesses. But none of these approaches has proved entirely successful in the efficient production of polynucleotides of pre-defined sequence having several hundred nucleotides. For instance, in one approach, genes or other large DNA fragments are synthesized by using the enzyme DNA ligase to join short, chemically-synthesized fragments of DNA into longer fragments. A few oligonucleotide fragments at a time are allowed to anneal under conditions that favor formation of correct, double-stranded fragments. These fragments are mixed with adjacent fragments in the target sequence and subjected to enzymatic DNA ligation reactions. The order in which the fragments assemble is determined by single-stranded overhangs at the end of each short fragments. One principal factor limiting the reliability of gene synthesis by this approach is the low fidelity of the DNA ligase reaction: the enzyme can join fragments with mismatched ends and thus assemble the fragments in the wrong order. Several variations on this basic strategy have been described (see, e.g., Khorana, H., *Science* 203:614-625 (1979); Stabinsky, Y., U.S. Pat. No. 4,652,639; and Hostomsky, Z. and J. Smrt, *Nucleic Acids Symposium Series* (18):241-244 (1987). Some of these strategies involve the use of polymerase to produce some or all of the product that is cloned (see, e.g., Withers Martinez C. et al. *Protein Engineering* 12:1113-20 (1999) and U.S. Pat. No. 5,492,609 to Hunkapiller and Hiatt). Other approaches have other shortcomings.

Because DNA is at the heart of modern biology, reliable and cost-effective gene synthesis has the potential to play a part in moving biology towards an engineering approach to product development rather than a purely discovery-based approach. More specifically, cost-effective gene synthesis has the potential to save drug discovery researchers hundreds of millions of dollars by allowing them to outsource complex molecular biology projects. As described in detail below, the present invention provides a significant advancement in the preparation of polynucleotides such as genes.

SUMMARY OF THE INVENTION

The present invention provides methods, devices and compositions that may be used in solid-phase polynucleotide synthesis. The technology of the present invention is advantageous for several reasons, including: 1) anchoring a growing chain on a support simplifies the reaction (only one end is exposed so fewer side reactions are available), 2) a molar excess of the solution phase component can drive the reaction, and 3) side reactions in solution are washed away with each cycle. Solid-phase techniques allow gene synthesis to be more reliable and more cost effective, and thus to allow it to substitute for a wider range of conventional cloning projects.

Solid phase synthesis can impact a polynucleotide manufacturing process in several ways, e.g.: 1) it can speed up production of up to 400 base pair fragments, 2) it has the potential to lower reagent usage and thus to allow the use of scaled-down oligo synthesis, and 3) it will increase the reliability of the assembly process, tightening delivery time variation and decreasing the costs associated with remaking failed fragments.

In one aspect, the present invention provides a method for gene assembly, comprising: (a) providing a universal oligo coupled to a solid support; (b) annealing a bridge oligo to the universal oligo to form a starting duplex comprising a sticky end; (c) annealing a first oligo or first duplex to the bridge oligo to form a first intermediate duplex; (d) annealing a second oligo or second duplex to the first intermediate duplex to form a second intermediate duplex; (e) repeating step (d) as needed to form a final duplex; (f) ligating together the oligo(s) and duplex(es) of the final duplex under conditions where the universal oligo does not undergo a ligation reaction, and the bridge oligo does not become ligated with either the first oligo or first duplex.

In another aspect, the present invention provides a composition comprising: (a) a universal oligo coupled to a solid support; and (b) a bridge oligo annealed to the universal oligo to form a starting duplex comprising a sticky end. This composition may optionally include: (c) a first oligo or first duplex annealed to the bridge oligo to form a first intermediate duplex; and optionally (d) a second oligo or second duplex annealed to the first intermediate duplex to form a second intermediate duplex; and optionally (e) a third oligo or third duplex annealed to the second intermediate duplex to form a third intermediate duplex; and optionally a ligase.

In another aspect, the present invention provides an article comprising a solid support coupled to a universal oligo, where one or more of a phosphate group and a polyoxyalkylene group are located between the solid support and a terminal nucleotide of the universal oligo. In a preferred embodiment this article further comprises a bridge oligo, where the bridge oligo comprises a linker polynucleotide region that is annealed to five or more nucleotides of the universal oligo. In a related aspect, the present invention provides a method of gene assembly, comprising (a) providing this article having a universal oligo but not having a bridge; (b) annealing a bridge oligo to the universal oligo; and (c) using a ligase to join two or more oligonucleotides together and form a target polynucleotide or fragment thereof. An advantage of this article and method is that the universal oligo/solid support construct is reusable. Accordingly, the method further includes the optional steps of (d) separating the universal oligo from the bridge oligo; and (e) re-using the article to make another target polynucleotide or fragment thereof.

In another aspect, the present invention provides a method for polynucleotide assembly on a solid support in an aqueous environment, the improvement comprising covalently coupling a universal oligo to a solid support either directly or through a linker group, annealing a bridge oligo to the universal oligo to form a starting duplex, the starting duplex having a portion of the bridge oligo in single stranded form to provide a sticky end, and hybridizing a first oligo or a first duplex to the sticky end of the starting duplex, where the first oligo or first duplex is subsequently subjected to ligation conditions and becomes incorporated into a target polynucleotide or fragment thereof.

The present invention prepares final genes, or fragments of genes, on a solid support. When the final desired gene is very long, e.g., more than about 1,000 base pairs, it may be more efficient to prepare two or more gene fragments on a solid support and then combine those gene fragments into the final desired gene. Accordingly, in one aspect the present invention provides a method for assembling a portion of a gene on a solid support, the method comprising: (a) assembling a first gene fragment on a solid support, the first fragment having at least 50 base pairs; (b) separating the first fragment from the solid support to provide a first fragment in a solution; (c) assembling a second gene fragment on a solid support, the second fragment having at least 50 base pairs and being non-identical to the first fragment; (d) separating the second fragment from the solid support to provide a second fragment in a solution; (e) assembling a third gene fragment on a solid support; (f) joining the third fragment to the first fragment to provide a longer gene fragment; (g) joining the second fragment to the longer gene fragment of step (e) to provide a final gene; and (h) separating the final gene from the solid support.

Basically, according to the method just described, any number of gene fragments may be prepared using the solid phase synthesis method of the present invention, and one of those gene fragments is left bound to the solid support while the previously made gene fragments are sequentially added to the support-bound gene fragment. Alternatively, all of the gene fragments may be released from the solid support and then assembled in solution. According to this aspect, the present invention provides a method for assembling a gene or portion thereof in solution, the method comprising: (a) assembling a first gene fragment on a solid support, the first fragment having at least 50 base pairs; (b) separating the first fragment from the solid support to provide a first fragment in a solution; (c) assembling a second gene fragment on a solid support, the second fragment having at least 50 base pairs and typically being non-identical to the first fragment; (d) separating the second fragment from the solid support to provide a second fragment in a solution; (e) combining the first fragment and the second fragment in a single solution; and (f) covalently joining the first and second fragments of step (e), typically under ligation conditions, to provide a final gene in solution.

In another aspect, the present invention provides a method of mixing support-bound oligo and solution phase oligo to achieve a high yield of hybridization between the two. Thus, in one aspect the present invention provides a method for gene or gene fragment assembly, comprising: (a) providing a partially double-stranded polynucleotide coupled to a solid support; (b) providing a solution of a single-stranded or a partially double-stranded polynucleotide that is at least partially complementary to a single stranded portion of the partially double-stranded polynucleotide of step (a); (c) contacting the solid support of step (a) with the solution of step (b) under the influence of a force exerted in one direction where at least some of the solution of step (b) passes by the partially double-stranded polynucleotide of step (a); and (d) reversing the direction of the force exerted in step (c) at least once so that at least some of the solution of step (b) passes by the partially double-stranded polynucleotide of step (a) at least twice; wherein the single-stranded or partially double-stranded polynucleotide of step (b) anneals to the single-stranded portion of the partially double-stranded polynucleotide of step (a).

Preferably, in this aspect of the invention, the direction of the force exerted in step (c) is reversed multiple times so that the partially double-stranded polynucleotide of step (a) is repetitively contacted with the solution of step (b). Even more preferably, in this aspect of the invention, the single-stranded or partially double-stranded polynucleotide of step (b) is partially double-stranded.

In another related aspect, this invention provides a method for gene or gene fragment assembly, comprising: (a) providing a partially double-stranded polynucleotide coupled to a solid support; (b) providing a solution of a single-stranded or a partially double-stranded polynucleotide that is at least partially complementary to a single stranded portion of the partially double-stranded polynucleotide of step (a); and (c) contacting the solid support of step (a) with the solution of step (b) under the influence of a force exerted in a direction where at least some of the solution of step (b) passes by the partially double-stranded polynucleotide of step (a); wherein the single-stranded or partially double-stranded polynucleotide of step (b) anneals to the single-stranded portion of the partially double-stranded polynucleotide of step (a).

Preferably, in this aspect of the invention, the single-stranded or partially double-stranded polynucleotide of step (b) is partially double-stranded.

In a related aspect, the present invention provides a method for gene assembly, comprising: (a) providing a partially double-stranded nucleic acid (ds-NA) coupled to a solid support; (b) providing a solution of single stranded nucleic acid (ss-NA) that is at least partially complementary to a single stranded portion of the ds-NA; and (c) contacting the ds-NA of step (a) with the solution of step (b) under conditions where at least some of the solution passes by the ds-NA under influence of a force, such that (i) the ss-NA anneals to the single-stranded portion of the ds-NA, and (ii) a reduction in the force will reduce the amount of ss-NA that anneals to the single-stranded portion of the ds-NA, under otherwise constant conditions.

The present invention also provides reactors and devices that are particularly useful in gene assembly. In one aspect, the present invention provides a device particularly well-suited for automated gene assembly comprising: (a) a reaction block comprising a plurality of cavities adapted to hold a plurality of reaction vessels, wherein each reaction vessel, when present within a cavity, comprises a first orifice, a second orifice, and a solid support positioned within the interior of the reaction vessel between the first and second orifice; and (b) a reagent delivery and mixing unit in fluid communication with the plurality of reaction vessels when present.

This device may be supplemented with additional components, e.g., the device may further comprise one or more means to control or monitor the temperature of the reaction block; the device may further comprise one or more means to monitor the fluid level within a reaction vessel when present; the device may further comprise one or more means to immobilize the plurality of reaction vessels within the plurality of the cavities of the reaction block; the device may further comprise one or more pumps in fluid communication with one or more valves; the device may further comprise a valve of the reagent delivery and mixing unit positioned between the first orifice of a reaction vessel when present and one of the pumps of the reagent delivery and mixing unit, where the valve is in fluid communication with the pump, the reaction vessel and one or more liquid storage containers, where a liquid in one of the liquid storage containers is transported from the liquid storage container through the valve into the reaction vessel by the action of the pump; the device may further comprise a microtiter plate (microplate) holding apparatus which may further comprise a temperature monitoring and control means; the device may further comprise a multi-microtiter plate (multi-microplate) storage system, which may further comprise a temperature monitoring and control means; the device may further comprise a means to transport a microplate from the multi-microplate storage system to the microplate holding apparatus; the device may further comprise a microplate-well seal-piercing means; and the device may further comprise a computer control unit, where the computer control unit executes pre-programmed commands to operate the various components of the device.

These and other aspects of the present invention are described in further detail below.

BRIEF DESCRIPTION OF THE SEVERAL VIEWS OF THE DRAWING(S)

FIG. 1 provides a schematic illustration of a method of assembly a gene fragment according to the present invention.

FIGS. 2 and 3 provide schematic illustrations of a construct formed between a solid support, a universal oligo, a bridge oligo, and a target gene or fragment thereof.

FIGS. 4A-D provides a schematic illustration of an assay method to determine ligation efficiency.

FIGS. 5A-5E depict reaction vessels having solid supports that may be used in the present invention.

FIG. 10A illustrates a reaction vessel in combination with a pump, valve and buffer reservoir according to the present invention.

FIG. 10B illustrates a reaction block containing a plurality of reaction vessels that may be used in gene synthesis according to the present invention.

Figure 11:
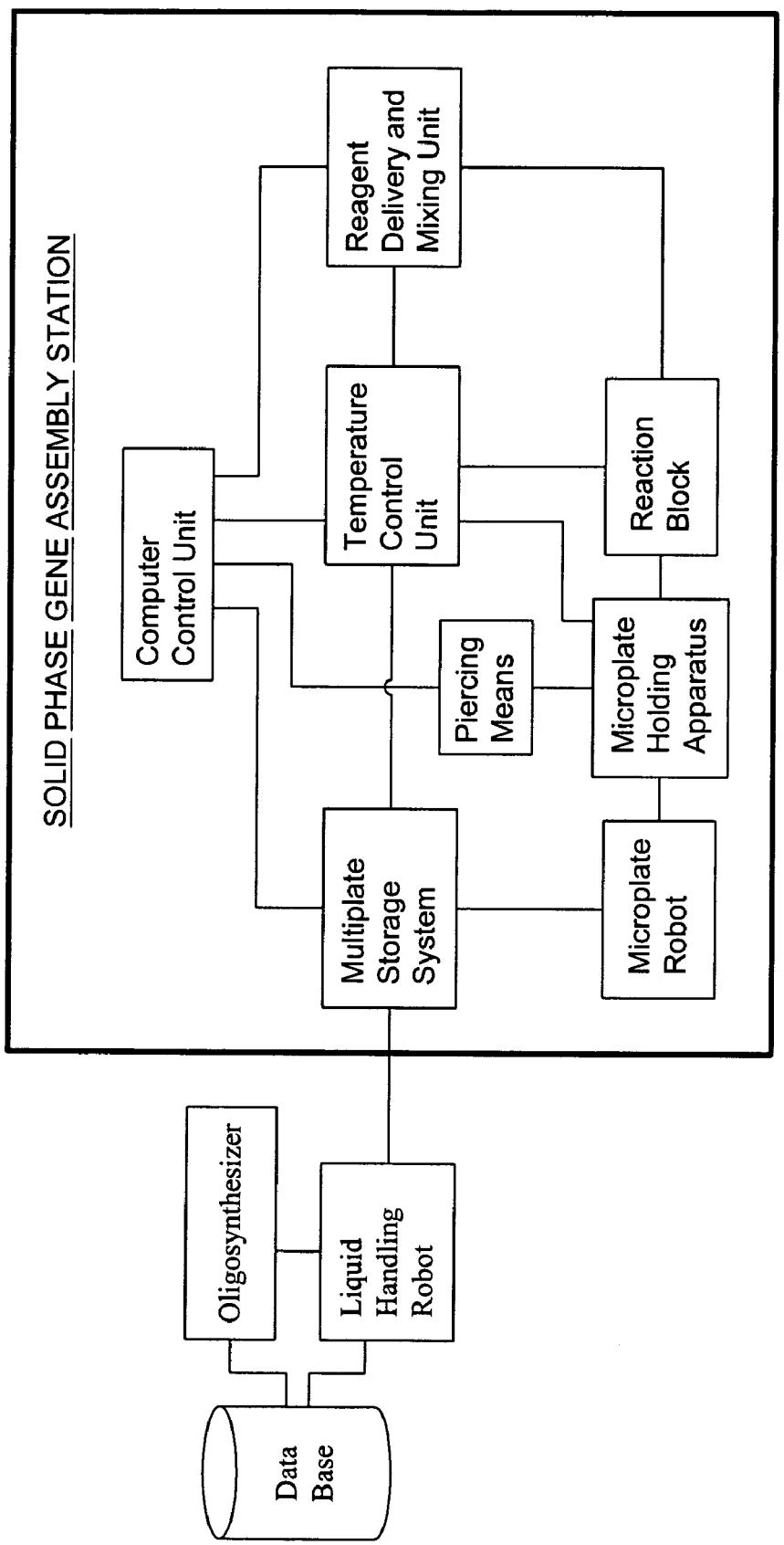

FIG. 11 provides a schematic of a solid phase gene assembly system of the invention.

FIGS. 12A-12F illustrate oligo assembly to prepare a gene fragment.

Figure 12E:
Figure 12F:
Figure 12G:
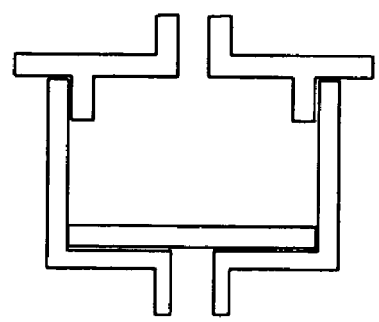

FIG. 12G is a schematic illustration of a reactor that may be used in the present method.

Figure 12H:
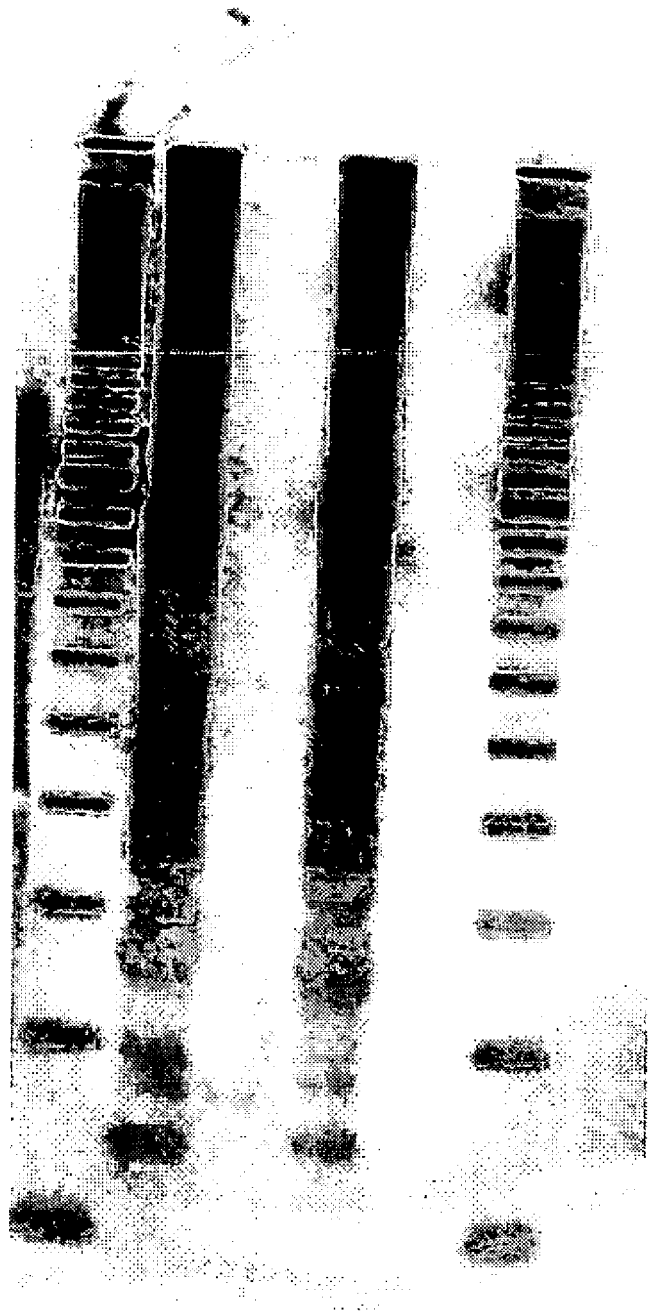
Figure 12I:

FIGS. 12H and 12I show gel electrophoresis results.

FIGS. 13A-13C illustrate oligo assembly to prepare a gene fragment.

Figure 13D:
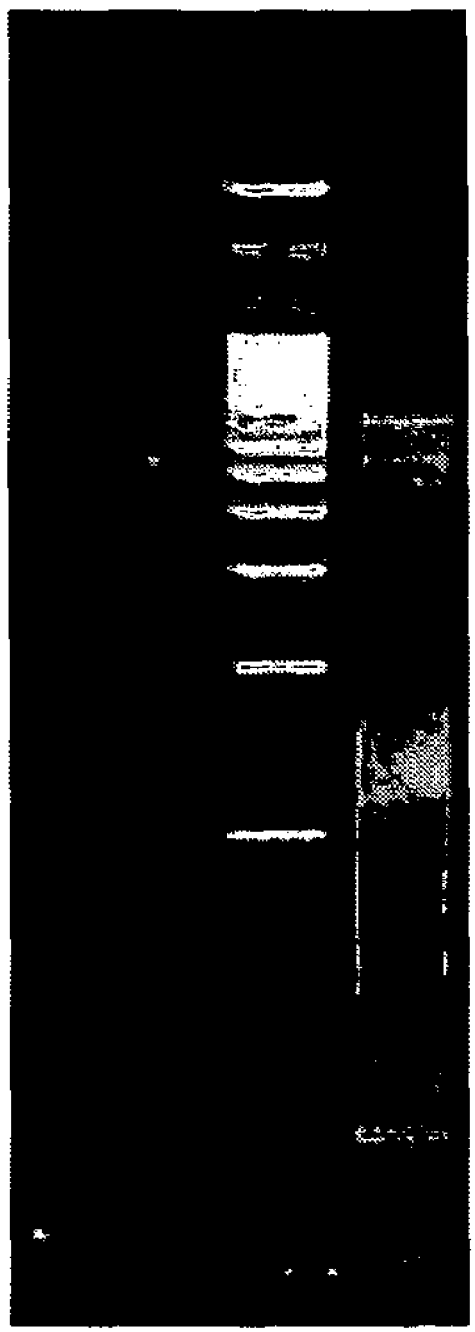

FIG. 13D provides a gel electrophoresis output.

Figure 14A:
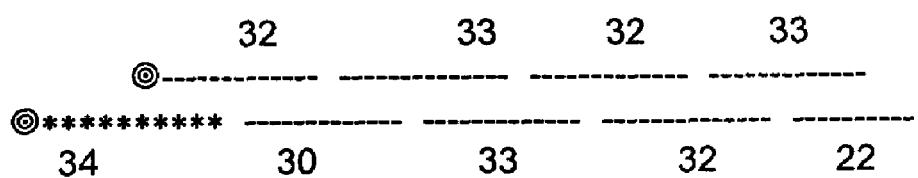
Figure 14B:
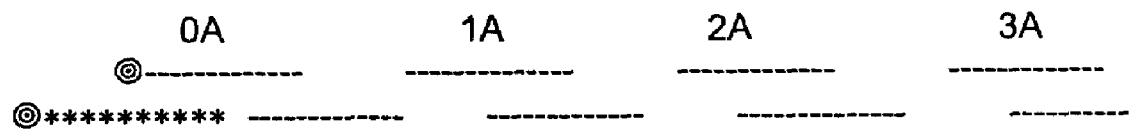

FIG. 14A and 14B illustrate oligo assembly to prepare a gene fragment.

Figure 14C:
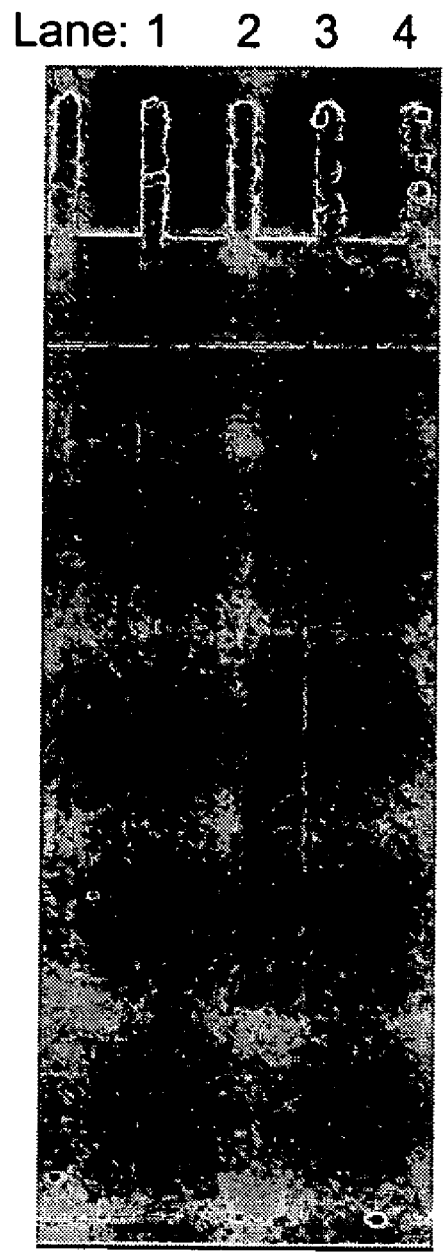
Figure 14D:
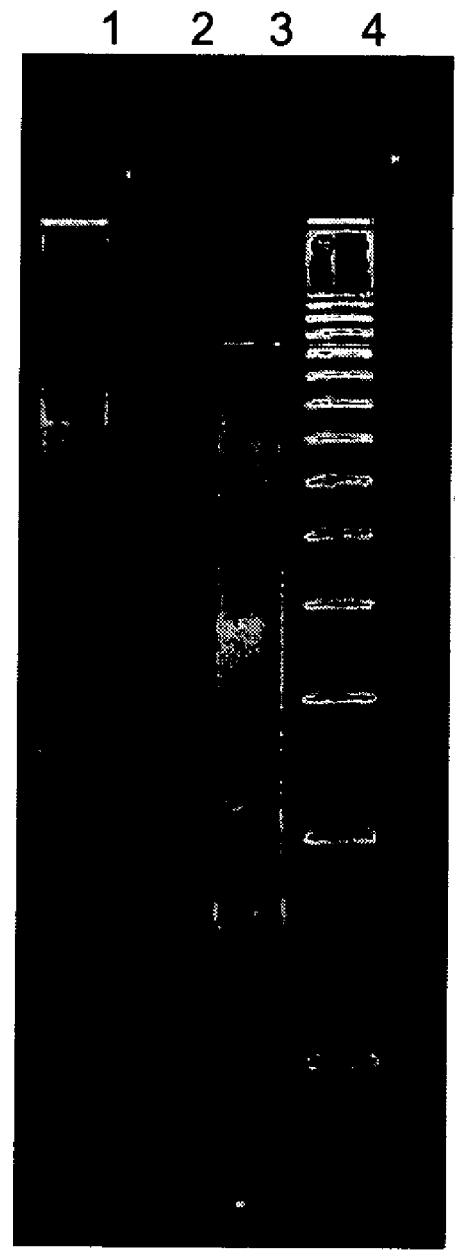

FIGS. 14C and 14D show gel electrophoresis results.

FIGS. 15A-15D illustrate oligo assembly to prepare a gene fragment.

Figure 15A:
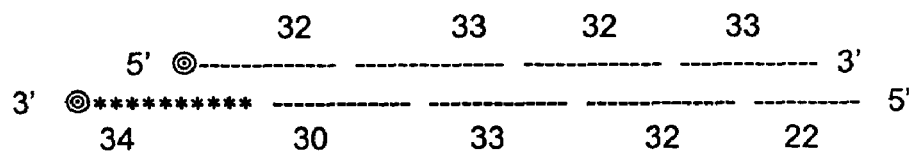
Figure 15B:
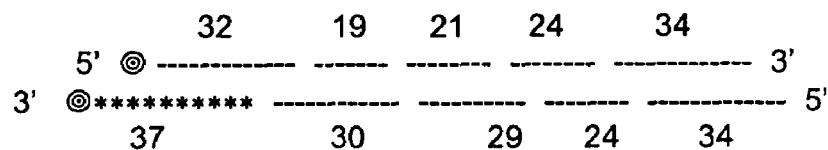
Figure 15C:
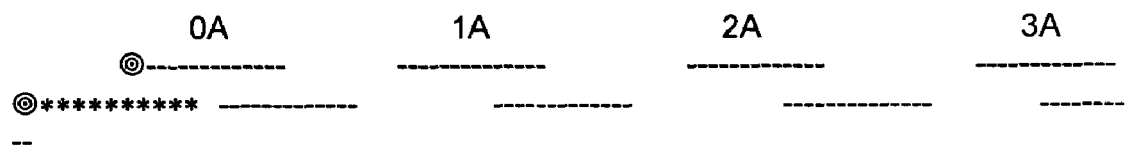
Figure 15D:
Figure 15E:
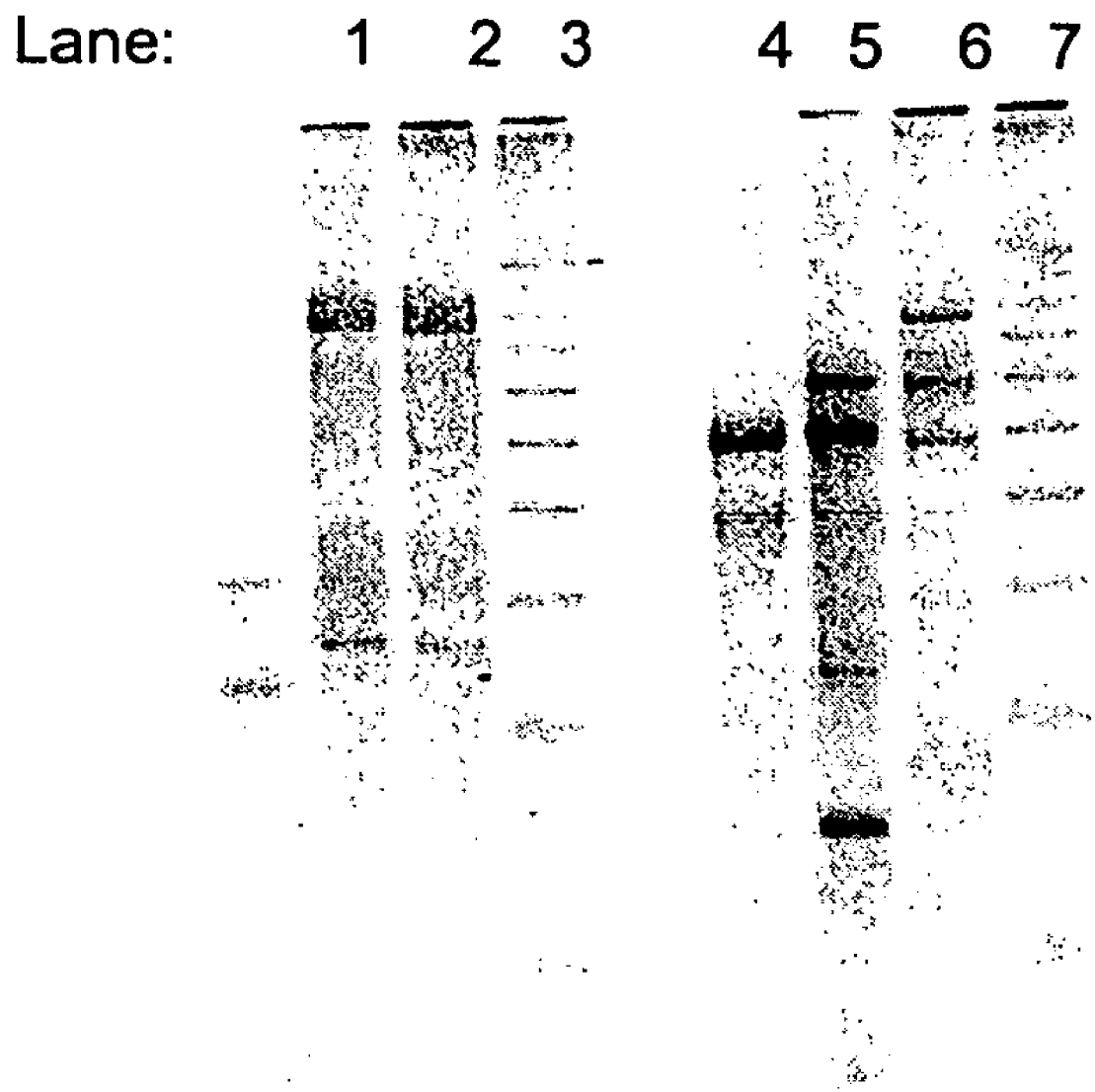

FIG. 15E shows the result of analysis by gel electrophoresis.

Figure 16:
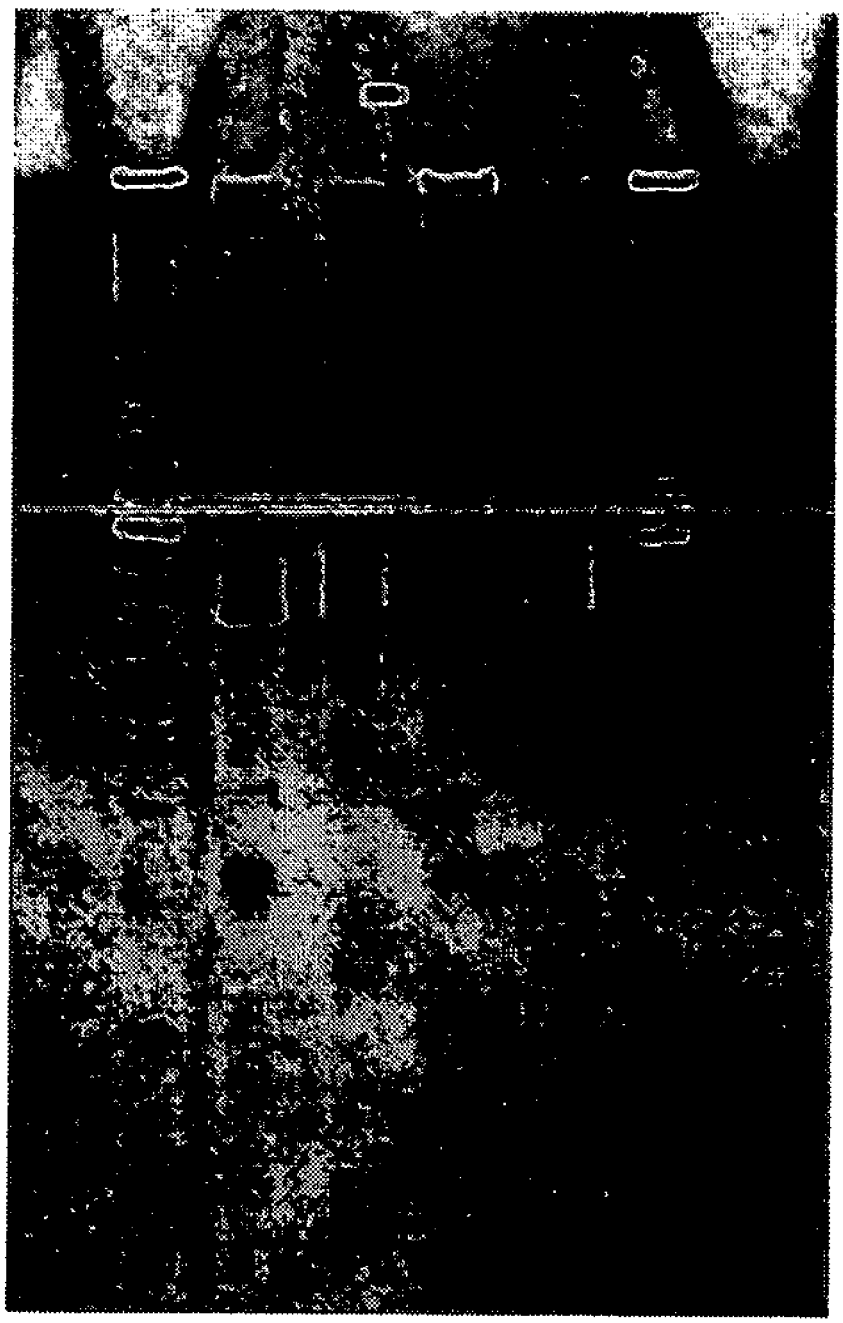

FIG. 16 shows the result of analysis by gel electrophoresis.

FIGS. 17A-17C illustrate oligo assembly to prepare a gene fragment.

Figure 17D:
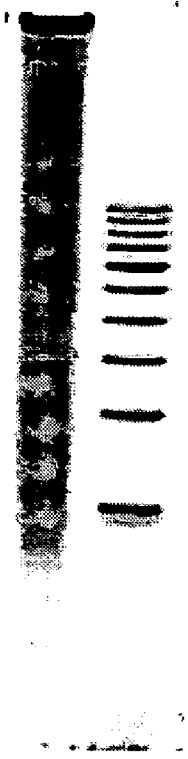
Figure 17E:
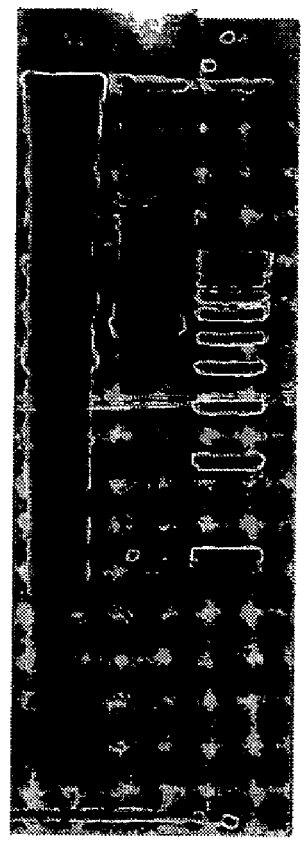

FIGS. 17D and 17E show the results from analysis by gel electrophoresis.

Figure 18:
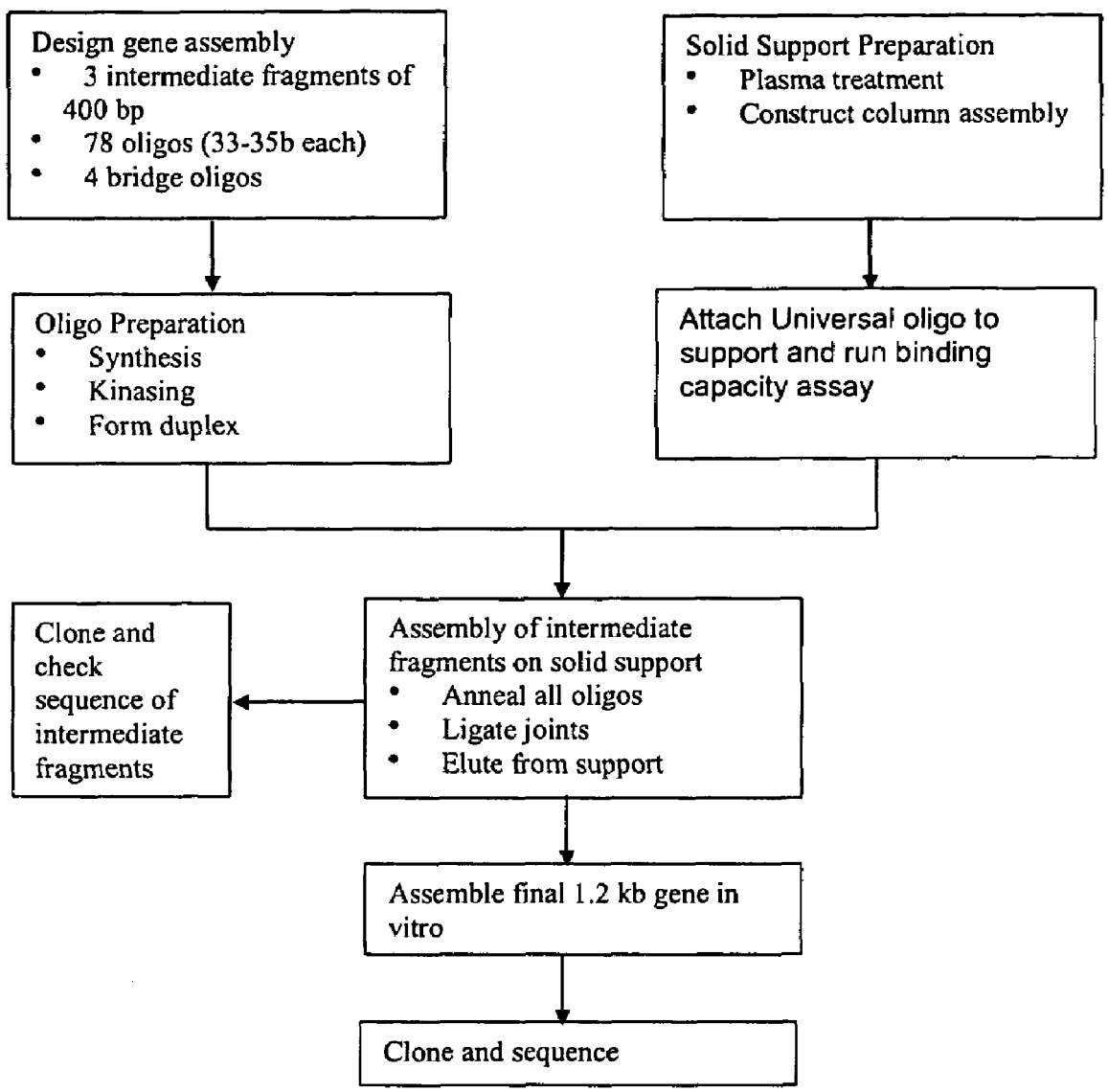

FIG. 18 provides a flowchart of a method to prepare a 1.2 kb gene.

Figure 19:
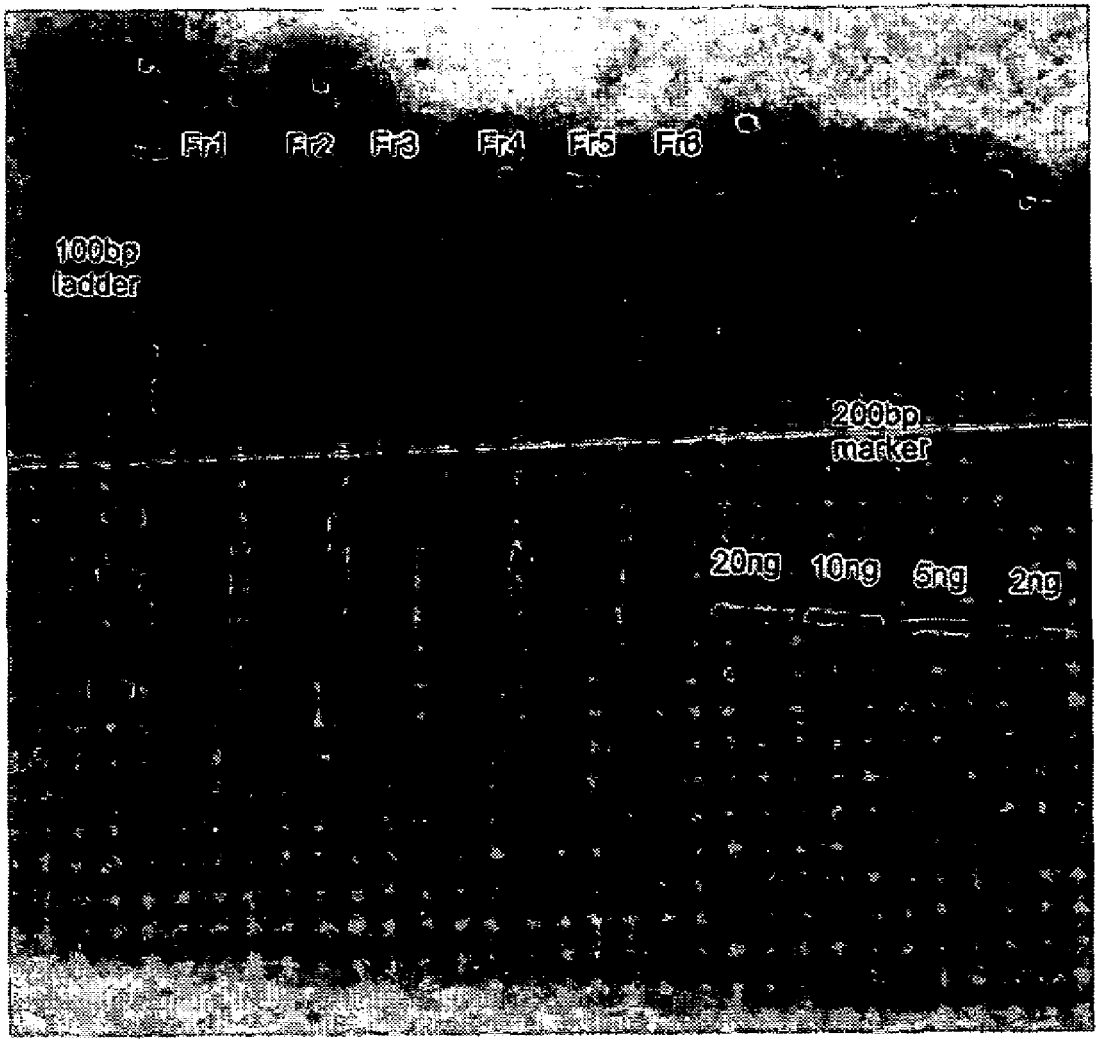

FIG. 19 shows the results from analysis by gel electrophoresis of gene fragments prepared by the solid phase gene assembly station of the invention.

DETAILED DESCRIPTION OF THE INVENTION

The present invention is directed to the synthesis of polynucleotides, and more particularly to synthesizing polynucleotides by a solid-phase process. Prior to setting forth details of the present invention, an overview of the invention and a clarification of some of the terms used to describe the invention will be provided.

A. Definitions and Conventions

As used herein, the terms "polynucleotide" and "gene", and their corresponding plural forms, are used interchangeably. Thus, the term "gene" does not necessarily refer to a nucleotide sequence also found in nature, although it can have this meaning, but more generally refers to a polynucleotide of any base sequence. As will be discussed in great detail below, the present invention uses solid phase chemistry to join oligos together and thereby assemble a gene. If the final desired gene has, e.g., 2,000 base pairs, then in one aspect of the invention, double-stranded fragments of this 2,000 bp gene are prepared by assembling oligos on a solid support, and then these gene fragments are assembled to form the final (2,000 bp) gene. For reasons discussed later, it is sometimes preferred to assemble oligos into gene fragments having on the order of 300-500 bps, and then assemble a plurality of those gene fragments into the final gene. For purposes of clarity, the product produced by the direct solid phase assembly of oligos will be referred to herein as a "gene fragment" or a "first polynucleotide". A product produced by the assembly of two or more "gene fragments," or first and second, etc., polynucleotides, will be referred to as a "gene".

The present invention prepares gene fragments in double-stranded form, wherein the nucleotide (nt) bases in a first polynucleotide molecule (sometimes referred to as a polynucleotide chain) are hydrogen-bonded to corresponding nucleotide bases in a second (adjacent) polynucleotide molecule. Under appropriate conditions, e.g., high temperature, the double-stranded (ds) form of a gene fragment can be converted to two single-stranded (ss) molecules. Accordingly, the terms "gene", "gene fragment", and "polynucleotide" can each be used to refer to both double-stranded and single-stranded forms. The term "polynucleotide molecule" will refer to one specific chain of nucleotides, which may be in either single-stranded or double-stranded form.

When the gene fragment is in double-stranded form, it will have a number of base pairs (bps). The present invention provides gene fragments having any number of base pairs. While the present invention can prepare short gene fragments, ie., gene fragments having less than 100 bps, there are alternative technologies known in the art to prepare short gene fragments. An advantage of the present invention is that it affords the preparation of long genes and long gene fragments, i.e., genes and gene fragments having more than 100 bps. In various embodiment of the present invention, genes and gene fragments having more than about (ca.) 100 bps, or more than ca. 200 bps, or more than ca. 300 bps, or more than ca. 400 bps, or more than ca. 500, or more than ca. 600 bps, or more than ca. 700 bps, or more than ca. 800 bps, or more than ca. 900 bps, or more than ca. 1,000 bps can be prepared. Most genes have less than ca. 5,000 bps, and so typically the present invention will be useful in preparing genes having ca. 100-5,000 bps from gene fragments having ca. 100-1,000 bps.

While the gene fragment produced by the present invention will have some nucleotides in base-paired form, not all of the nucleotides present in the gene fragment (or the gene) are necessarily in base-paired form. In fact, in many (but not all) instances, some of the nucleotides at one or both ends of a particular polynucleotide molecule will not be paired with any other bases, even though the internally-located nucleotides of that molecule are in base-paired form. A sequence of one or more non-base-paired nucleotide(s) at the end(s) of a polynucleotide molecule may be referred to herein as forming a "sticky end". These one or more non-base-paired nucleotides are considered "sticky" because they are available to hybridize with another single-stranded polynucleotide molecule, which is in contrast to nucleotides that are already in double-stranded form and so are no longer "sticky".

A double-stranded polynucleotide will be referred to herein as a "duplex", where a duplex necessarily contains two (a first and a second) polynucleotide molecules, where a contiguous sequence of nucleotides in a first polynucleotide molecule is hybridized to a contiguous sequence of nucleotides in the second polynucleotide molecule. The terms "hybridize" and "anneal" will be used interchangeably herein to refer to a process whereby two single-stranded polynucleotide molecules join together to form a duplex. Thus, the term "duplex" encompasses both genes and gene fragments.

In order for a duplex to form from two ss-polynucleotides, a sequence of nucleotides in the first polynucleotide molecule must be complementary to a sequence of nucleotides in the second polynucleotide molecule. The fact that the nucleotides derived from adenine (A) and guanine (G) are complementary to, and thus may base pair with the nucleotides derived from thymine (T) and cytosine (C) is well known in the art. As will be discussed in detail below, the present invention relies upon the phenomenon that two polynucleotides, upon being mixed together under appropriate conditions, may spontaneously hybridize to form a duplex. In order for this spontaneous hybridization to occur, a sufficient number of the nucleotides in the first polynucleotide molecule must be arranged in a manner that allows them to base pair with complementary nucleotides in the second strand. In other words, the two polynucleotide molecules must have complementary sequences.

For many purposes it is desired that all of the base pairs in a gene or gene fragment prepared by the present invention are either A/T or G/C, and mismatches (e.g., A/A, T/T, G/G, C/C, A/C, A/G, T/C and T/G base pairs) are undesirable. However, the present invention has flexibility in that it can purposely create some mismatched bases in a product gene or gene fragment. Thus, the term "duplex" as used herein does not require the complete absence of mismatched bases, and in fact some mismatches may be present in the duplex. However, as the number of these mismatches increases, the duplex loses stability, and eventually the duplex is not stable at room temperature. Accordingly, while a duplex prepared by the present invention may have one or more mismatched bases, the number of mismatched bases should not be so great that the duplex is not stable at room temperature.

The present invention joins oligonucleotides (oligos, or ODNs) together to form a gene or gene fragment. As used herein, the term "oligonucleotide" (oligo, ODN) refers to a short chain of nucleotides. Existing technology is available to produce polynucleotide molecules having less than about 100 nts, where this technology creates these molecules by "growing" a chain. In essence, this "growing" process entails joining a first nucleotide to a solid support, activating the first nucleotide, adding a reactive second nucleotide to the activated first nucleotide, allowing the second nucleotide to react with the first nucleotide to form a dinucleotide, washing away any unreacted materials and reaction by-products, activating the dinucleotide so the portion derived from the second nucleotide is reactive, and then repeating the process (ie., adding a reactive third nucleotide to the activated dinucleotide, allowing the third nucleotide to react with the dinucleotide to form a trinucleotide, etc., etc.). The oligonucleotide formed by the process is then released from the solid support.

The "growing" process works fairly well for producing short polynucleotides. However, each time a nucleotide is added to the chain, some error is introduced, e.g., two nucleotides are added to the chain instead of one, or no nucleotide is added to the chain. Accordingly, the yield of desired product decreases rapidly as the length of the polynucleotide increases. Due in part to this error rate, but also due to the slowness of this process and other reasons, the "growing" method is not suited for, and is not used to, prepare long genes, i.e., genes of much more than 100 nts.

The oligos of the present invention have at least 10 nts. Preferably, the oligos have at least 20, or at least 30, or at least 40, or at least 50, or at least 60, or at least 70, or at least 80, or at least 90, or at least 100 nts. In fact, longer oligos are generally preferred. The problem with using longer oligos is that when they are made using standard commercial technology, they are often impure in that a sample of, for example, a 50 base oligo (a "50-mer") may have 90% (by weight) 50-mer and some non-50-mer, e.g., some 48-mer, 49-mer, 51-mer 52-mer, etc. Furthermore, only ca. 90% of the 50-mer may have the desired nucleotide sequence. In general, while chromatography may be used to remove oligos that are shorter or longer than the desired oligo, the purification of a 50-mer to remove 50-mers that have an undesired nt sequence is very difficult. Accordingly, this step-growth process for preparing a gene has not been commercially successful.

An oligo of the present invention is a synthetic molecule comprising a chain of nucleotides (nts). The oligo will have at least 10 nts. The upper limit for the number of nts in the oligo is not critical. However, if the oligo itself is long (e.g., 300 nts or more) and the desired gene or gene fragment is short (e.g., only ca. 300 nts), then the method to make the oligo (and its complement) can be used to make the gene, and the present invention is not needed to make the gene! The present invention is directed to joining oligos together to form a longer polynucleotide, where for some reason the technology used to synthesize the oligos is inadequate, or not well suited to form a long polynucleotide having the desired number of nucleotides. Current technologies for making oligos on a commercial scale are adequate for making oligos having up to about 100 nts. Accordingly, in one aspect, the oligo of the present invention has 10 to about 100 nts.

As used herein, the term "a" refers to "one or more". For example, "a pump" refers to one or more pumps. In some instances, for purposes of clarity, the term "one or more" will be used, however, the terms "a" and "one or more" are generally interchangeable.

B. Method For Synthesizing Gene or Gene Fragment

1. Overview of Method

The present invention assembles oligos to form a gene by following three major steps. Step 1 is the assembly of oligos to form a gene fragment. To reiterate, if the gene fragment has the desired length, then the gene and gene fragment are one in the same. However, if the desired gene has more bps than a gene fragment, then in a second step the gene fragment is cloned and sequenced, to thereby obtain the gene fragment in highly pure form. In a third step, the purified gene fragments are assembled into the final large polynucleotide.

Figure 1:
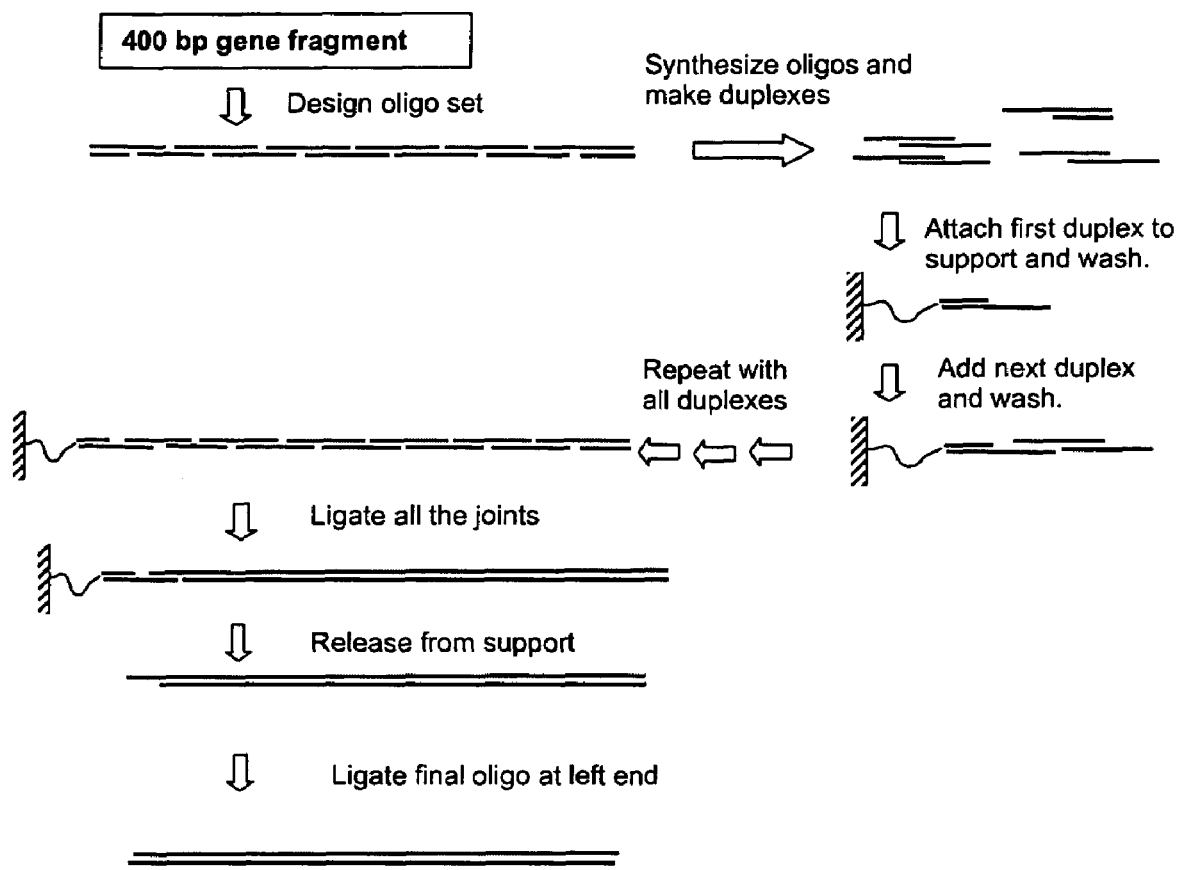

Step 1, assembly of the intermediate gene fragments, is illustrated in FIG. 1. In brief, three components are used in this process: 1) a solid support carrying a universal oligo, 2) a fragment-specific bridge oligo used to link the support to the growing fragment, and 3) the set of oligos that are used to build the gene fragment. The bridge oligo is composed of two sections, one complementary to the universal oligo coupled to the solid support and the second complementary to a "first oligo". The first oligo may be in single or double stranded form. When in double-stranded form, the first oligo provides a "sticky end" with which it can anneal to the bridge oligo. FIG. 1 shows the use of first oligo in duplex form, i.e., in a form where it has been pre-annealed with a second oligo. The bridge provides a reversible link between the support and the growing fragment and is removed after release of the fragment from the solid support. The bridge oligo is not included in the fragment clone or in the final gene.

Thus, the first step in building a gene is to decompose the sequence into gene fragments, and then decompose the sequence of the fragments into a set of overlapping oligos. These oligos are then synthesized by methods known in the art. While each oligo may be as short as 10 nucleotides, and may be as long as, or even longer than 100 nucleotides, in various aspects of the invention each oligo is 20-100 nts, or 20-80 nts, or 20-60 nts, or 20-40 nts, or 30-100 nts, or 30-80 nts, or 30-60 nts, or 30-40 nts. In a preferred aspect, each oligo is about 30-60 nucleotides in length and overlaps with two oligos in the opposite strand. Each overlapping region between two oligos can be annealed together to form a stable duplex at each joint at room temperature. While the oligos may be added sequentially to the growing chain, in one aspect two or more oligos are pre-annealed to form a duplex (having a sticky end) and the duplex is annealed to the stick end of the growing chain.

The assembly process begins by annealing a bridge oligo to a solid support derivatized with the universal oligo. After the annealing step the excess unattached bridge oligo is washed off from the solid support. Next, the first oligo, optionally in duplex form, is annealed to the bridge oligo. The excess unattached duplex is washed off from the solid support. This annealing and washing cycle repeats for each consecutive oligo or duplex until all the oligo are annealed together. A single enzymatic ligation reaction covalently connects all the joints of the gene at the end. Finally, the double stranded gene fragment is released from the solid support.

Thus, the present invention provides a method for gene assembly, comprising:

(a) providing a universal oligo coupled to a solid support;

(b) annealing a bridge oligo to the universal oligo to form a starting duplex having a sticky end;

(c) annealing a first oligo or first duplex to the sticky end to form a first intermediate duplex;

(d) annealing a second oligo or second duplex to the first intermediate duplex to form a second intermediate duplex;

(e) repeating step (d) as needed to form a final duplex;

(f) ligating the oligo(s) and duplex(es) of the final duplex together under conditions where the universal oligo and the bridge oligo do not ligate to each other or to any other oligo or duplex.

2. The Solid Support

As used herein, the term "solid support" has its usual meaning as understood by those skilled in the art of organic synthesis conducted on solid phase supports. To be useful in the present invention, a solid support is both a solid, i.e., not a liquid or a gas, and is insoluble in water at room temperature and pH 7. The solid support of the present invention is stable in the presence of water, that is, the solid support retains its chemical composition and form during long-term, e.g., 24 hour, exposure to water. A solid support useful in the present invention may undergo some change upon initial exposure to water, e.g., it may swell, but after this initial change the solid support is stable, i.e., unchanging as to chemical structure, in water. A surface of a solid support is accessible to contact with solutes dissolved in water, when the solid support is placed into the water.

The solid support will have a surface to volume ratio. Methods to determine surface to volume ratio are well known in the art, and commercial suppliers of solid supports for organic synthesis often report the surface to volume ratio of a solid support. Typically, a higher surface to volume ratio is preferred for a solid support of the present invention. This is because the preparation of a polynucleotide according to the present invention depends on extending a polynucleotide that is initially linked to the surface of the solid support. When the surface area of the solid support is increased for a fixed volume of solid support, it is typically possible to link more of the initial polynucleotide to the surface and thereby prepare more of the extended polynucleotide that is the desired product of the present invention. Accordingly, porous solid supports are preferred in the present invention.

The solid support preferably has one or more of the following properties: (a) the support should be non-swelling in solution to avoid entrapment of large molecules; (b) the support should not contain pores or crevices small enough to hinder further growth of the polymer chains; (c) the functional groups should be accessible at the support surface; (d) the support should be inert to reagents and conditions used in the process and not interfere with the assembly process; (e) the surface density of the functional group should be appropriate for gene assembly; and (f) surface coupling chemistry should be reproducible, efficient and economical.

A preferred solid support material for solid phase gene assembly is porous polyethylene or polypropylene. These surfaces may be derivatized by plasma treatment (R. Matson, J. Rampal and P. Coassin, *Analytical Biochemistry*, (1994), vol. 217, 306-310) followed by covalent coupling of the reactive groups introduced by the plasma treatment, to the universal linker oligo, by carbodiimide chemistry. The advantage of using one-piece, i.e., monolithic, porous frits as opposed to a collection of loose resin beads is that the frits allow for the repeated forward/reverse flow method to circulate a small volume of reagent around the solid surface during annealing and ligation reactions. This mixing mode is especially beneficial for large molecule solid phase reactions beyond 200-bp gene length. While not meaning to be bound by this theory, it is believed that the flow helps extend the long coiled ds-polynucleotide molecules and make their propagating ends more accessible to solution targets (T. Perkins, D. Smith and S. Chu, *Science*, (1997) vol. 276, 2016-2021; D. Smith, H. Babcock and S. Chu, *Science*, (1999) vol. 283, 1724-1727; C. Haber and D. Wirtz, *Biophysical Journal*, (2000) vol. 79, 1530-1536). The support is preferably a stationary support rather than a loose bead, in order to increase the efficiency of the coupling steps.

A preferred solid support material for use in the devices and methods of the present invention is porous polyethylene with 5-35 μm pores. This material is commercially available from several manufacturers such as Porex Technologies (Fairburn, Ga.) and Porvair Advanced Materials (Hendersonville, N.C.). Both companies are capable of molding the frits directly. Alternatively, these companies and other vendors are capable of dye stamping custom frit shapes from sheets or rods of the bulk material.

An alternative solid support material is a polystyrene resin that can be used in the same column described above. The advantage of using this material is that it can be used to prepare the solid support and couple oligo to it in conventional batch mode. The resin is packed tight and contained between two pieces of polyethylene frits in the same reactor column described above. Preparation of the solid support is simpler and more economical than preparing individual frits, although packing the columns may be more time-consuming.

Other organic solid supports that may be used in the present invention include, without limitation, polypropylene, polyacrylate and polymethacrylate. Instead of an organic solid support, and inorganic material may be used, where exemplary inorganic materials include, without limitation, metal oxides, e.g., silica or alumina.

The solid support may be in any convenient form, where suitable forms include, without limitation, monolithic porous materials and membranes. The solid support may be porous by virtue of being a collection of non-porous materials, for example, beads, fibers, or other particulate forms.

3. The Universal Oligo

The assembly process of the present invention begins with an oligonucleotide linked to a solid surface, where this particular oligonucleotide is referred to herein as the universal oligonucleotide, or universal oligo. The universal oligo is extended by contact with additional (second, third, etc.) oligos, optionally in duplex form, in the manner described below, to provide a double-stranded polynucleotide (ds-polynucleotide). A portion of the ds-polynucleotide is then separated from the solid support to provide both the desired ds-polynucleotide and the universal oligo still bound to the solid surface. One of the many benefits of the present invention is that the starting material, i.e., the universal oligonucleotide bound to a solid surface, is regenerated at the end of the polynucleotide synthesis, and can be used to generate additional polynucleotides. The oligonucleotide that is linked to the solid support is termed herein the universal oligonucleotide because the nucleotide sequence of the universal oligo is independent of the nucleotide sequence of the first polynucleotide, i.e., the universal oligo can be used "universally", i.e., for any sequence of first polynucleotide.

The manner in which the universal oligonucleotide is linked to the solid support is not critical to the present invention, so long as the universal oligonucleotide (i) is linked in such a way that it is accessible to hybridization reactions with a second oligonucleotide (termed herein the bridge oligonucleotide), and (ii) will remain linked to the solid support during the course of the extension reaction(s). Both oligonucleotides and solid supports are very well known in the art. Furthermore, methods to link oligonucleotides to solid supports are very well known in the art. Furthermore, oligonucleotide(s) linked to solid support(s) in the manner required by the present invention are very well known to one of ordinary skill in the art.

One common approach is to use a solid support with carboxylic acid functionality, and then react those carboxyl groups with amine-terminated oligonucleotides. The opposite approach is also commonly used in the art, i.e., using a solid support with amine functionality on the surface of the support, and reacting that support with a carboxylic acid-terminated oligonucleotide. In either case, an amide group links the oligonucleotide to the solid support.

By convention, oligonucleotides are recognized to have both a 3' and a 5' end. Either the 3' end or the 5' end of the universal oligo may be linked to the solid support according to the present invention. However, a special requirement of the support-bound universal oligonucleotide is that the end of the oligonucleotide that is not linked to the solid support, which will be referred to herein as the free end, must be both non-reactive and spatially similar or identical to a natural nucleotide. Options for achieving a non-reactive free end will be described later herein.

The number of nucleotides present in the universal oligo, and the base sequence of those nucleotides is not critical. Preferably, the universal oligo has 5-50 nucleotides. If the universal oligo has less 5 nucleotides, then it will not form a very stable hybrid with the bridge oligo. To achieve a reasonably stable hybrid, the universal oligo preferably has 10-30 nucleotides, e.g., about 20 nucleotides. While universal oligos having more than 30 nucleotides may be employed in the practice of the present invention, these relatively long universal oligos are not particularly advantageous (especially when a linker group is positioned between the universal oligo and the solid support), and generally are more expensive to create.

The base sequence of the universal oligo is not critical. Preferably, the sequence is selected so that the universal oligo will not form hairpins. Also, the sequence should be selected so that a hybrid of the sequence has a Tm (melting temperature for 50% of the duplexes) above the working temperature of the reaction, i.e., above about room temperature. Also, it is preferred that the universal sequence not have only A, or only T, or only G or only C.

4. Linker Groups

While the universal oligo may be directly linked to the solid support, in one aspect of the invention a linker group is positioned between the universal oligo and the solid support. The linker group is present, in part, as a matter of convenience. That is, some solid supports have reactive groups that are not reactive with a reactive group that is easily or economically present in a universal oligo. In this case, the linker group is bifunctional, and has functional groups that are reactive with both the solid support and the universal oligo. However, the linker group also serves the purpose of allowing the universal oligo to extend further into solution, and thus be more available to reaction with the bridge oligo. Accordingly, in one aspect of the invention a linker group is located between the solid support and the universal oligo.

In a preferred aspect, a segment of polyoxyalkylene is located between the solid support and the nucleotide sequence of the universal oligo. This segment of polyoxyalkylene is preferably polyoxyethylene. In one aspect, there are 2-50 oxyalkylene units in the segment of polyoxyalkylene, while in various other aspects there are 2-40, 4-40, 6-40, 2-30, 4-30, 6-30 oxyalkylene units in the polyoxyalkylene. While the polyoxyalkylene unit may contain more than 30 oxyalkylene groups, this tends to increase the cost of the universal oligo/solid support article. This polyoxyalkylene segment may contain phosphate groups. The phosphate groups are conveniently positioned within the polyoxyalkylene segment because, e.g., solid-phase synthesis approaches to oligo manufacture can be readily used to include polyoxyalkylene segments within or adjacent to the polynucleotide segment, in those cases where the polyoxyalkylene segments include phosphate groups.

5. The Bridge Oliqo and the Starting Duplex

Figure 2:
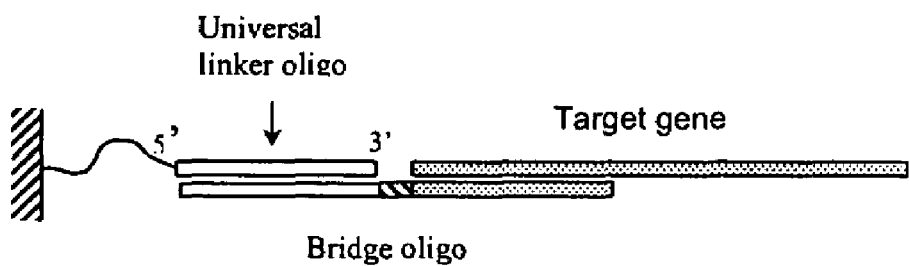

As illustrated in FIG. 2, a bridge oligo is annealed to both the universal linker oligo on the solid support and to one end of the target gene. This bridge oligo does not participate in the ligation and so it can be removed under mild denaturing conditions. There are several advantages of this method. A single solid support with a universal oligonucleotide simplifies production, quality control and inventory. The selective reversibility of the link allows for the release of the product gene or gene fragment from solid support easily under the correct buffer and the thermal conditions and thus avoids the addition of restriction site sequences to the target. A key advantage of the reversible linkage is that the solid support is reusable which means production of a new gene does not involve the process of manually loading new solid support.

In a first step according to the present invention, a bridge oligonucleotide is hybridized to the universal oligonucleotide. Methods to obtain a bridge oligonucleotide of any desired nucleotide sequence are very well known in the art. Indeed, such oligonucleotides are commercially available from many sources. The product of this first step is referred to as the starting (or initial) duplex.

A requirement of the starting duplex is that a portion of the bridge oligonucleotide is not hybridized to the universal oligonucleotide. Preferably, the portion of the bridge ODN that is not hybridized to the universal ODN consists of a sequence of contiguous nucleotides where the sequence is at least 5, or 6, or 7, or 8, or 9, or 10, or 11, or 12, or 13, or 14, or 15, or 16, or 17, or 18, or 19, or 20 or more nucleotides in length. Methods to form a suitable hybrid between a universal (support-bound) oligonucleotide and a bridge (solution phase) oligonucleotide are likewise very well known in the art.

The hybrid between the universal and bridge oligonucleotides should be relatively strong, at least relative to the hybrid that is formed between the bridge ODN and the first ODN that forms part of the first polynucleotide. In one aspect, the universal ODN has at least a 50% GC content, as G/C bonds are stronger than A/T bonds. A typical number of bases that is hybridized to form the first hybrid is 17. As the number of hybridized bases in this hybrid decreases, then the hybrid should typically contain a greater percentage of G/C base pairs, in order to maintain the strength of the hybrid. Typically, in order to provide sufficient strength to the hybrid, the first hybrid should have at least about 10 bases that are in hybridized form. While the hybrid can contain more than 17 hybridized bases, it is observed that when more than about 25 bases are in hybridized form, there is a greater chance for hybrids to form that do not have the desired base pairs. Nevertheless the upper limit for the number of hybridized bases in the first hybrid is greater than 25, even greater than 30.

6. First Intermediate Duplex

In a second step, which may be conducted prior to, concurrently with, or subsequent to the first step, a first ODN is allowed to contact the bridge ODN. The first ODN is called the "first" ODN because it is the first of the ODNs discussed so far that will become part of the first polynucleotide. The first ODN is at least partially complementary to, and therefore will hybridize to, a portion of the bridge ODN that is not complementary to, and thus is not hybridized to, the universal ODN. When the first ODN hybridizes to the bridge ODN, a second hybrid is thereby formed, where the second hybrid comprises the universal ODN hybridized to a first nucleotide region of the bridge ODN, and the first ODN hybridized to a second nucleotide region of the bridge ODN, where the first ODN additionally comprises a nucleotide region that does not hybridize to either the universal or bridge ODN.

When the second step is conducted concurrent with the first step, then the bridge and first ODNs are simultaneously allowed to contact the universal oligonucleotide. In one embodiment of this "concurrent" approach, the bridge and first ODNs are annealed to one another before they are contacted with the universal ODN. When the second step is conducted subsequent to the first step, then the first ODN hybridizes to the first hybrid. When the second step is conducted prior to the first step, then the universal and first ODNs are contacted with one another but do not hybridize, and when the bridge oligonucleotide is added it hybridizes to both the universal and bridge ODN.

This first intermediate hybrid must meet many requirements in order to be useful in the present invention. First, the free end of the universal ODN, i.e., that end not directly coupled to the solid support, must not covalently join to any other oligonucleotide during the course of the oligonucleotide ligation reaction. One way to achieve this goal is to make sure that the free end of the universal ODN does not contain a hydroxyl group. In the case of attaching the solid support to the 3' end of the universal ODN, the 5' end may lack a phosphate group in order to ensure it does not enter into a ligation reaction with another ODN. In addition, according to a preferred embodiment of the invention, the bridge ODN is designed such that there is a sequence of nucleotides, referred to herein as a gap sequence, that lies between the nucleotide sequence that hybridizes to the universal ODN and the sequence of nucleotides that hybridizes to the first ODN. This gap sequence effectively separates the free end of the universal ODN from the end of the first ODN that is closest to the free end of the universal ODN, by a distance equal to the length of the gap sequence, as these ends are present in the second hybrid.

As an additional criteria, the Tm (melting temperature) of the hybrid formed between the universal and bridge ODNs is preferably greater than the Tm of the hybrid formed between the bridge and first ODNs. In this way, the bridge and universal ODNs remained hybridized under conditions that melt (de-hybridize) the bridge and first ODNs.

7. Washing Steps

During each step in the process, the desired product should be present in purified form, i.e., free from undesired ODN. For instance, after the universal ODN is linked to the solid support, it is desired to wash away any non-linked (solution phase) universal ODN. Likewise, when it is desired to form the first intermediate hybrid, the bridge ODN is preferably washed away from the first hybrid before continuing the oligonucleotide extension reaction. Likewise, after the second intermediate hybrid is formed, any universal, bridge or first ODN that is not part of the second hybrid is preferably washed away so that it can no longer contact the second hybrid. In this way, the yield of the desired polynucleotide, as based on the molar amount of surface-bound universal ODN, tends to increase.

8. First Oligo vs. First Duplex

The first ODN may or may not be hybridized to a second ODN at the time when the first ODN hybridizes to the bridge ODN. However, a necessary feature of the first ODN is that even after it hybridizes to the bridge ODN, there is a nucleotide sequence available to hybridize to a second, partially complementary ODN. Likewise, for a third ODN, and a fourth ODN, etc. as needed to prepare the first polynucleotide or desired portion thereof. That is, each ODN, including the first, second, third, fourth, fifth, etc. ODN, hybridizes to two ODNs that are present in the complementary strand of the double-stranded polynucleotide prepared according to the present invention. In other words, each of first, second, etc. ODNs partially hybridize to two ODNs. When an ODN, e.g., the second ODN, is hybridized to two complementary ODNs, e.g., the first and third ODNs, there is preferably not a nucleotide gap between the two complementary ODNs, e.g., between the first and third ODNs when they are both hybridized to the second ODN. In this way, a ligase will be able to join together the first and third ODNs. In other words, in total, the first, second, third, etc. ODNs comprise each of the nucleotides that are present in the first polynucleotide or the desired portion thereof.

In an optional embodiment of the present invention, two or more ODNs may be ligated together before the final ligation reaction that forms the first polynucleotide. For example, after the first, second and third ODNs have been annealed together to form the first intermediate duplex, the resulting construct may be exposed to ligation conditions. This ligated product may then be exposed to fourth, etc. ODNs and/or duplexes in order to build towards preparing the first polynucleotide. Prior to the final ligation reaction, the surface-bound ODNs, in partially or non-ligated form, are referred to herein as the ODN construct.

9. Ligation

After each of the ODNs are hybridized to one another in the desired order, the fully hybridized construct is exposed to ligating conditions in order to covalently join the first, third, fifth, etc. ODNs to one another in sequence, and to covalently join the second, fourth, sixth, etc. ODNs to one another in sequence. After this ligation reaction, the only ODNs that have not been ligated to another ODN are the universal and bridge ODNs.

10. Gene Fragment Isolation

After the ligation reaction is completed, the product is exposed to denaturing conditions so that the ligated fragments are denatured from the bridge ODN, and the bridge ODN is denatured from the universal ODN. The final product from this sequence of reactions is the solid support linked to the universal ODN, the bridge ODN, and a first polynucleotide that is the product of the first, second, third, fourth, etc. ODNs. The universal oligo may now be used to prepare another gene or gene fragment.

C. From Gene Fragment to Gene

1. Assembly of Gene Fragments

In one aspect of the invention, the polynucleotides produced by ligating oligos together are fragments of the final desired polynucleotide (gene). As the number of oligos being ligated together increases, the likelihood that a specific polynucleotide has the desired sequence decreases. This is largely due to the fact that the oligos are not 100% pure. Accordingly, in a preferred aspect of the invention to prepare a desired polynucleotide having more than about 800 base pairs, two or more gene fragments are produced using the solid phase synthesis procedure described herein, and then those two gene fragments are joined together, preferably under ligation conditions, to create the final desired polynucleotide.

Thus, the first polynucleotide may or may not be the final desired target polynucleotide. In one aspect of the invention, the first polynucleotide is the final desired target, and it has end groups that allow it to be inserted into a vector or other construct that allows the first polynucleotide to be utilized, e.g., function as a template for mRNA synthesis. However, in another aspect of the invention, the first polynucleotide is not the final desired target. In order to prepare the final desired target, a second polynucleotide is prepared, preferably in the same manner as the first polynucleotide was prepared. These first and second polynucleotides are designed so that they each have an overhang nucleotide sequence, where an overhang nucleotide sequence in the first polynucleotide is complementary to an overhang nucleotide sequence in the second polynucleotide. In order to prepare the final target polynucleotide, the first and second polynucleotides are contacted in solution, in the presence of a ligase that joins the first and second polynucleotides together. As before, the target polynucleotide may be designed so that it can be inserted into a vector or other construct that allows the target to function as a template for mRNA synthesis.

In another aspect of the present invention, multiple polynucleotides, i.e., first, second, etc. polynucleotides, are prepared by the solid-phase process just-described, where these multiple polynucleotides can be joined together, e.g., via a ligation reaction, to form the target polynucleotide. In other words, the present invention provides that two or more polynucleotides, where at least one of these polynucleotides was prepared by the solid-phase synthesis method of the present invention, may be ligated together in order to form the target polynucleotide.

Thus, one aspect of the invention provides a method for assembling a gene or portion thereof on a solid support, the method comprising:

(a) assembling a first gene fragment on a solid support, the first fragment having at least 50 base pairs;

(b) separating the first fragment from the solid support to provide a first fragment in a solution;

(c) assembling a second gene fragment on a solid support, the second fragment having at least 50 base pairs and being non-identical to the first fragment;

(d) joining the first fragment to the support-bound second gene fragment, to provide a final gene; and (e) separating the gene of (d) from the solid support.

For clarification it is noted that the gene fragments in this and the method described are two nucleic acid molecules in duplex or partially duplex form—they are not a set of individual oligos which are hybridized together. Instead of combining only two gene fragments together, more than two gene fragments may be combined to prepare the desired gene. For example, the present invention provides a method wherein three gene fragments are combined, comprising:

(a) assembling a first gene fragment on a solid support, the first fragment having at least 50 base pairs;

(b) separating the first fragment from the solid support to provide a first fragment in a solution;

(c) assembling a second gene fragment on a solid support, the second fragment having at least 50 base pairs and being non-identical to the first fragment;

(d) separating the second gene fragment from the solid support to provide a second fragment in solution;

(e) assembling a third gene fragment on a solid support;

(f) joining the first fragment to the support-bound third gene fragment, to provide a longer gene fragment, and the joining the second gene fragment to the longer gene fragment to provide a final gene; and (g) separating the final gene from the solid support.

This method may be extended to allow for the combining of 4, 5, 6, 7 or more gene fragments to provide the final gene. These methods rely, in part, on leaving one of the gene fragments bound to the solid support, and then adding solution-phase gene fragments to the solid support-bound gene fragment. However, in another aspect of the invention, all of the gene fragments are combined together in solution. For instance, the present invention provides a method for assembling a final gene in solution, the method comprising:

(a) assembling a first gene fragment on a solid support, the first fragment having at least 50 base pairs;

(b) separating the first fragment from the solid support to provide a first fragment in a solution;

(c) assembling a second gene fragment on a solid support, the second fragment having at least 50 base pairs and being non-identical to the first fragment;

(d) separating the second fragment from the solid support to provide a second fragment in a solution;

(e) combining the first fragment and the second fragment in a single solution; and (f) covalently joining the first and second fragments of step (e) to provide a final gene in solution.

This method may be extended to preparing three, four, five, etc. gene fragments, and then combining those fragments in solution to provide the final desired gene.

D. Article Comprising a Solid Support Coupled to a Universal Oligo

1. Solid Support+Linker Group+Universal Oligo

In a separate aspect of the present invention there is provided an article comprising a solid support, a polynucleotide (e.g., the universal oligo described previously) and a linking group that is positioned between the support and polynucleotide. The linking group is covalently bonded to both the solid support and the polynucleotide, so this aspect of the invention provides an article that may be represented by the formula SS)-L-PN, where "SS)" represents the solid support, "L" represents the linking group, and "PN" represents the polynucleotide. The 5' end of PN may be directly bonded to L, in which case the article may be represented by the formula SS)-L-PN(5'), or the 3' end of PN may be directly bonded to L, in which case the article may be represented by the formula SS)-L-PN(3'), where these are two separate aspects of the invention.

The linking group is, or includes a (i.e., one or more) polyoxyalkylene group. In various embodiments, one or any two or more of the following criteria may be used to describe the article: the polyoxyalkylene group is a polyoxyethylene group; two polyoxyalkylene groups are present in the linking group, where these two polyoxyalkylene groups are separated by a phosphate group, thus providing a structure that may be represented by POA-PH-POA, where "POA" represents the polyoxyalkylene group and "PH" represents the phosphate group; three polyoxyalkylene groups are present in the linking group, where they are separated from one another by a phosphate group, i.e., the linker includes the structure POA-PH-POA-PH-POA; the linker further comprises a hydrocarbon group (HC), where the hydrocarbon group is located between the solid support and the polyoxyalkylene group, so as to provide a structure that may be represented by HC-POA-(optionally PH-POA, etc.), where "HC" represents the hydrocarbon group; the hydrocarbon group has a formula weight of 50-500 g/mol; the polynucleotide group consists of 5-50 nucleotides; the 5' end of the polynucleotide is coupled to the linker group and the 3' end of the polynucleotide contains a phosphate group or other group that is not ligatable with the 5' phosphorylated end of another oligo or duplex; the 5' end of the polynucleotide is coupled to the linker group and the 3' end of the polynucleotide terminates in a hydroxyl group.

Thus, in one aspect, the present invention provides an article that may be represented by the formula SS)-(POA-PH)$_n$-POA-HC-PN(3'), where n is an integer selected from 1-10.

2. Solid Support+Linker Group+Universal Oligo+Bridge Oligo

In another aspect, the present invention provides the article as just described (i.e., an article of the formula SS)-L-PN), which is annealed to a bridge oligo. The bridge oligo includes a linker polynucleotide region that is annealed to some or all of the nucleotides present in the "P" group. Preferably, the linker polynucleotide region consists of 5-50 contiguous nucleotides. The bridge oligo further includes a bridging polynucleotide region consisting of 5-50 contiguous nucleotides, where the bridging polynucleotide region does not anneal to the polynucleotide group of PN. The bridge oligo in annealed form with PN is termed herein the initial or starting duplex, where this starting duplex is one aspect of the present invention. In one aspect, the article is represented by the formula SS)-L-PN(3'), and the bridge oligo that anneals to PN lacks a phosphate group at the 3' end of the bridge oligo.

3. Solid Support+Linker Group+Universal Oligo+Bridge Oligo+First Oligo

In another aspect, the bridging polynucleotide region of the bridge ODN is annealed to a first oligo (A) or first duplex (A+B), where for convenience this discussion will refer to a first duplex. This situation is illustrated in FIG. 3, where |represents the solid support, and ———— and """""""" """""""" each represents polynucleotides.

Figure 3:
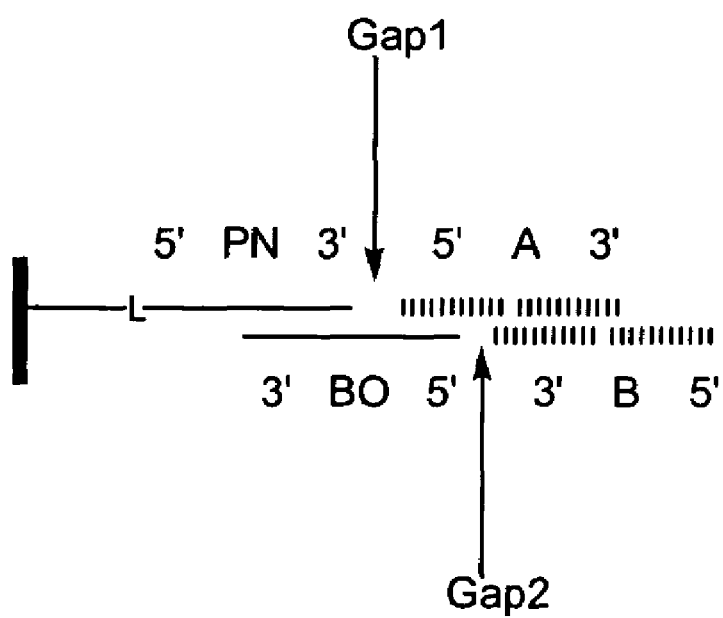

In this configuration, as shown in FIG. 3, it is desired that both the 3' and 5' ends of A be able to undergo a ligation reaction, and both the 3' and 5' ends of B be able to undergo a ligation reaction. However, it is necessary that neither the 3' end of PN nor the 5' end of BO undergo a ligation reaction when the construct shown in FIG. 3 is contacted with ligase. To achieve these goals, two approaches may be taken. The first is termed the gap approach, whereby both PN and A anneal to BO, but they anneal in such a way that a nucleotide gap, or spacer region, is formed between the 3' end of PN and the 5' end of A. This is shown as Gap 1 in FIG. 3. This gap is at least one nucleotide in length, and in various aspects of the invention the gap is 2, or 3, or 4, or 5, or 6 nucleotides in length. This same approach, i.e., creating a gap, can be employed to assure that the 5' end of BO does not ligate with the 3' end of B, where this approach entails forming a gap, shown as Gap 2, in FIG. 3, between these two ends.

An alternative approach is to cause the 3' end of PN to be "non-ligatable", i.e., structurally inconsistent with the action of a ligase. Since the 5' end of A will terminate in a phosphate group, in order to cause the 3' end of PN to be non-ligatable with the 5' end of A, the 3' end of PN should lack a hydroxyl group. For example, the 3' end of PN may have a phosphate group, so that both the 3' end of PN and the 5' end of A have phosphate groups, where two phosphate groups will not ligate together under the action of ligase. In this case, Gap 1 may be 0 nucleotides in length. Optionally, Gap 1 is 1 or more nucleotides in length and the 3' end of PN will be non-ligatable with the 5' phosphate group of A. This approach provides double protection against the 3' end of PN entering into a ligation reaction with A.

In various aspects of the invention: Gap 1 is 1 to about 5 nucleotides in length, PN has a 3' hydroxyl group, Gap 2 is 0 nucleotides and BO lacks a 5' phosphate group; Gap 1 is 1 to about 5 nucleotides in length, PN has a 3' hydroxyl group, Gap 2 is 1-5 nucleotides in length, BO has a 5' phosphate; Gap 1 is 0 nucleotides in length, PN lacks a 3' hydroxyl, Gap 2 is 0 nucleotides and BO lacks a 5' phosphate group; Gap 1 is 0 nucleotides in length, PN lacks a 3' hydroxyl, Gap 2 is 1 to about 5 nucleotides and BO has a 5' phosphate group.

4. Methods of Using Article

In another aspect, the present invention provides a method of polynucleotide assembly that utilizes the above-described article(s). That is, the present invention provides a method of polynucleotide synthesis that includes (a) providing an article as described above which comprises the solid support, the linker group, the universal oligo and the bridge oligo;

(b) annealing an oligo or duplex to the article of (a); and (c) using a ligase to join two or more oligos together and form a first target polynucleotide.

In an optional embodiment, the method further includes:

(d) separating the bridge oligo from the universal oligo.

In another optional embodiment, after the bridge oligo has been separated from the universal oligo, the universal oligo is annealed to another bridge oligo in order to allow the formation of a second target polynucleotide. In other words, the solid support-bound universal oligo is re-used to make another gene or gene fragment.

In another aspect, the present invention provides a method for polynucleotide assembly on a solid support in an aqueous environment, which can utilize methods for polynucleotide assembly as known in the art, with the inventive improvement including covalently coupling a universal oligo to a solid support, annealing a bridge oligo to the universal ODN to form a starting duplex, the starting duplex having a portion of the bridge ODN in single stranded form to provide a sticky end, and hybridizing a first oligo or first duplex to the sticky end of the starting duplex, where the first oligo/duplex is subsequently elaborated to form a target polynucleotide. In optional embodiments, one or more of the following criteria may be used to further define this inventive method: the universal oligo comprises a polyoxyalkylene group and a polynucleotide group, where the polyoxyalkylene group is located between the solid support and the polynucleotide group; the polyoxyalkylene group is a polyoxyethylene group; two polyoxyalkylene groups separated by a phosphate group are present between the solid support and the universal oligo; multiple polyoxyalkylene groups separated by phosphate groups are present between the solid support and the universal oligo; a hydrocarbon group is located between the universal oligo and the polyoxyalkylene group, where the hydrocarbon group has a formula weight of 50-500 g/mol; the universal oligo consists of 5-50 nucleotides; the universal oligo lacks a terminal phosphate group; the universal oligo has a terminal phosphate group; the bridge oligo comprises a linker polynucleotide region that is annealed to some or all of the nucleotides that form the universal oligo; the linker polynucleotide region of the bridge oligo consists of 5-50 contiguous nucleotides; the bridge oligo further comprises a bridging polynucleotide region consisting of 5-50 contiguous nucleotides, where the bridging polynucleotide region does not anneal to the nucleotides of the universal oligo; the bridging polynucleotide region is separated from the universal polynucleotide region by a spacer group, where the spacer group is a contiguous series of 1 to about nucleotides; and the method further includes annealing the bridging polynucleotide region of the bridge oligo to a first oligo or a sticky end of a first duplex, where the first oligo/duplex comprises a polynucleotide region that anneals to the bridge ODN, and the first oligo/duplex further comprises a polynucleotide region that is single-stranded but does not anneal to the bridge oligo; the single-stranded region of the first oligo/duplex that does not anneal to the bridge oligo has 5-50 nucleotides; the first target polynucleotide made by this method includes at least 100, or at least 200, or at lest 300, or at least 400, or at least 500 base pairs.

E. Mixing Conditions

In one aspect, the present invention provides a method of contacting a solid support-bound polynucleotide with a polynucleotide in solution (either of which may be in partially duplex form) in order to anneal the solution polynucleotide to the support-bound polynucleotide. While the support-bound polynucleotide preferably incorporates a universal oligo and a bridge oligo according to an aspect of the invention described previously, in the present aspect of the invention the support-bound polynucleotide need not have this particular configuration. In other words, the present method of contacting a solid support-bound polynucleotide with a polynucleotide in solution in order to anneal the solution polynucleotide to the support-bound polynucleotide is generally applicable to any support-bound polynucleotide.

In order to prepare a polynucleotide according to the present invention, a surface-bound partially double-stranded oligonucleotide (the starting duplex) is allowed to anneal to an incoming oligo or duplex. In order to continue extending the length of the surface-bound oligonucleotide(s), part of each incoming oligo/duplex will anneal to the support-bound partially double-stranded ODN construct, and the remainder of the incoming ODN will remain single-stranded so as to provide a site for further extension. The reaction conditions under which an incoming oligo or duplex is contacted with the surface-bound partially double-stranded ODN construct are quite important to achieve a high yield of annealed product. The yield of annealed product is the percentage of surface-bound partially double-stranded ODN that anneals to an incoming ODN.

In one aspect of the invention, the solution containing the incoming ODN contacts the surface of the solid support at a time when the partially double-stranded ODN construct is in an extended conformation. While not intending to be bound by this theory, the present inventor suggests that the ODN construct is in a thermodynamically stable from when it is coiled or folded over on itself when the ODN construct has reached a certain length. Thus, the thermodynamically stable form of the construct may, and often does, have the growing end buried within the ODN construct, or buried within or otherwise shielded by the rest of the ODN construct or even a neighboring ODN construct, and therefore away from contact with the solution. In order to bring this growing end into contact with an incoming ODN, it is helpful to have the growing end extended into solution rather than interacting with other solid support-bound ODNs. In order to achieve this extension, the present invention provides that the solution of incoming ODN is forced past the ODN construct, and/or the surface that supports the ODN construct, preferably in a vigorous manner. This force extends the growing end away from other ODN molecules and into solution, so that the growing end is more accessible to the incoming ODN.

Thus, in a preferred aspect, this extended conformation is achieved when the solution is forced past the solid surface. For instance, the surface may be the interior of a tube, and the solution is flowed through the tube at a sufficient rate to extend the conformation of the ODN construct. As another example, the surface may be a frit that divides a reaction chamber into two sub-chambers, and the solution is passed from one sub-chamber to the other at a sufficient rate to extend the conformation of the ODN construct. As another alternative, the ODN construct may be bound to the interior surface of a chamber, the solution containing the incoming ODN is poured into the chamber, and a stirring device, e.g., a mechanical stirrer, is placed within the solution so that stirring causes the solution to pass by the surface-bound ODN construct and force the growing end away from intimate contact with the ODN construct. This approach, where the solution of incoming ODN is forced past a stationary ODN construct, will be referred to as the static surface approach.

As an alternative, the solution of incoming ODN could be static and the surface linking the ODN construct may be pushed or dragged through the solution. For instance, the solution of incoming ODN could be located in a chamber, and the surface binding the ODN construct could be the fins of a stirring device, e.g., a mechanical stirrer. When the stirring device was in operation, the fin surfaces would be pushed through the solution and the partially double-stranded ODN construct would be forced into an extended confirmation. The direction in which the fins turn may be alternated, to achieve a washing machine-type action. In general, this approach whereby the surface coupled to the polynucleotide is forcefully moved through a solution, will be referred to herein as the static solution approach. The static solution approach is an example of repetitive flow-through mixing.

Whether the inventor's theory is correct or not, it is empirically observed that forcing the solution of incoming ODN past the surface-bound ODN construct, and/or forcing the surface-bound ODN construct through the solution of incoming ODN, leads to a desirable increase in the yield of the first polynucleotide, relative to the situation where neither is forced past another.

In order to achieve a high yield of annealed product it is preferable that a surface-bound ODN construct have multiple opportunities to contact incoming oligonucleotide in solution. In one aspect of the invention, this goal is achieved by repeatedly (e.g., two times, three times, four times) passing a fixed amount of oligonucleotide-containing solution across the surface that binds the partially double-stranded ODN construct. For instance, when the surface-bound partially double-stranded ODN construct is bound to a frit that separates two sub-chambers, the solution of incoming ODN can be transferred multiple times through the frit as it is transferred from one sub-chamber to the other. When the surface-bound partially double-stranded ODN construct is bound to the inside of a tube, the tube may form a loop and the solution of incoming ODN may be pumped repeatedly through the loop. This approach, where a fixed volume of oligonucleotide-containing solution is repeatedly passed by a location on the surface to which is bound the partially double-stranded ODN construct, will be referred to herein as the continuous flow-through contact or the recycling approach.

Alternatively, if enough oligonucleotide-containing solution is available, this goal may be achieved by passing an increasing amount of oligonucleotide-containing solution across the surface that binds the partially double-stranded ODN construct. For instance, oligonucleotide-containing solution may be pumped from a reservoir though a tube having the interior surface bound to partially double-stranded ODN construct, for a time sufficient to anneal the desired amount of surface-bound partially double-stranded ODN construct to incoming ODN. This approach, referred to as the non-cycling approach, typically requires more solution oligonucleotide than does the recycling approach in order to achieve the same yield of annealed product, and for this reason the non-recycling approach is the less preferred approach.

In the above-described methods, the same mechanical force is used to achieve both extension of the partially double-stranded ODN construct and multiple contacts between the partially double-stranded ODN construct and the incoming ODN in solution. This is a preferred aspect of the present invention. However, this approach requires that the force used to achieve multiple contacts between the partially double-stranded ODN construct and the incoming ODN in solution be sufficient to also achieve extension of the partially double-stranded ODN construct. For instance, when the polynucleotide is bound to the fins of a mechanical stirrer, the stirrer must be operating at a sufficient rotational velocity that the bound ODN construct is extended. Likewise, when the ODN construct is bound to the surface of a frit, the solution of incoming ODN must be passed across the frit from one chamber to another at a rate sufficient to cause the growing end of the ODN construct to extend into solution. As used herein, "mechanical force" refers to the amount of energy being put into the system in order to achieve movement of the solution and/or surface.

Whether the mechanical force is sufficient to cause extension of the surface-bound partially double-stranded ODN construct will depend on the solution viscosity and the exact configuration of the reaction vessel. For instance, the length and inner diameter of the column, or the pore size and thickness of the frit. For any particular configuration, the conditions necessary to achieve extension of the ODN construct may be readily determined by running a few exploratory reactions. For instance, after the configuration has been established, a set of reaction conditions is randomly selected and the yield of annealing achieved under those conditions is measured. Then, the mechanical force may be increased by a selected value, e.g., 50%, and the yield of annealing is measured under these new conditions. For example, the flow rate past a particular fixed point on the surface to which partially double-stranded ODN construct is bound, may be increased by about 50%. If these new reaction conditions achieve a greater yield of annealing, then the mechanical force may be further increased, e.g., by 50%, and the yield of annealing remeasured. If these new reaction conditions do not achieve a greater yield of annealing, then it may be that excess mechanical force was used in the first reaction, and a second reaction should be run using less, e.g., 50% less, mechanical force. In this way, one can readily achieve a plot of mechanical force vs. annealing yield. Typically, below a threshold mechanical force, varying the mechanical force will not increase the yield of annealing. Also typically, above a certain mechanical force, increasing the mechanical force will not lead to any further increase in the yield of annealing, but it instead may cause breakage of the DNA chain/ODN construct. One of ordinary skill in the art can select a suitable mechanical force and configuration based on specific constraints and goals.

As used herein, higher annealing yield is asserted to be caused by extension of the surface-bound partially double-stranded polynucleotide, and extension is asserted to be caused by mechanical force. This is the inventor's theory to explain the observed results. The actual observed result is that the annealing yield is not very high unless adequate mechanical force is used during the annealing reaction. That is, it is empirically observed that the annealing yield is quite low for relatively longer surface-bound partially double-stranded ODN constructs, unless some mechanical force is used whereby the solution and the surface are forced pass one another.

In a preferred aspect of the invention, a volume of solution is repeatedly passed across a surface area of solid support, where the surface area is bound to a partially double-stranded ODN construct, and the volume of solution contains oligonucleotide that is complementary to a single-stranded portion of the surface-bound ODN construct. Preferably, the volume of solution is repeatedly passed across the surface area of the solid support under a pressure such that a reduction in the pressure would result in a lower yield of ODN being annealed to the surface-bound partially double-stranded ODN construct, all of factors, e.g., time, oligonucleotide concentration, and temperature, being kept constant.

In a related aspect, surface-bound partially double-stranded ODN construct is forcibly moved through a solution containing incoming ODN, where the incoming ODN is at least partially complementary to the single-stranded portion of the surface-bound partially double-stranded ODN construct. Preferably, the surface-bound partially double-stranded ODN construct is forcibly moved through the solution with such a force that a reduction in the force would result in a lower yield of incoming ODN being annealed to the surface-bound partially double-stranded ODN construct, all of factors, e.g., time, oligonucleotide concentration, and temperature, being kept constant.

In one aspect the present invention provides that most, if not all of the surface-bound partially double-stranded ODN construct anneals to incoming oligonucleotide, and accordingly in various aspects the present invention provides that at least 50%, or at least 60%, or at least 70%, or at least 80%, or at least 90%, or at least 95% of the surface-bound partially double-stranded ODN construct anneals to incoming oligonucleotide, where the percent values are mol% based on the moles of partially double-stranded ODN construct that are bound to the solid support.

The effect of extending the growing end of the ODN construct by flow mixing on the annealing yield is not very noticeable when the ODN construct is relatively short, for example, less than about 200 nucleotides. However, as the ODN construct becomes longer, exposing the growing end to the solution becomes a more important factor in achieving a high annealing yield. Accordingly, in various aspects of the present invention, the surface-bound partially double-stranded ODN construct that is exposed to the growing end-extension conditions is greater than 200 nucleotides, or greater than 300 nucleotides, or greater than 400 nucleotides, or greater than 500 nucleotides, or greater than 600 nucleotides, or greater than 700 nucleotides, or greater than 800 nucleotides, or greater than 900 nucleotides, or greater than 1,000 nucleotides, or greater than 1,200 nucleotides, or greater than 1,400 nucleotides, or greater than 1,600 nucleotides, or greater than 1,800 nucleotides, or greater than 2,000 nucleotides, or greater than 2,500 nucleotides, or greater than 3,000 nucleotides, or greater than 3,500 nucleotides, or greater than 4,000 nucleotides, or greater than 5,000 nucleotides, where each of these values is optionally capped at about 6,000 nucleotides or 7,000 nucleotides, or 8,000 nucleotides, or 9,000 nucleotides or 10,000 nucleotides.

The use of "force" according to the present invention to achieve mixing between a support-bound partially double-stranded oligonucleotide and a solution of oligonucleotide is generally application to any system having these two components. Thus, the support-bound partially double-stranded oligonucleotide is preferably, but is not necessarily, the "starting duplex" defined above which was formed from a universal oligo and a bridge oligo.

Thus, in one aspect, the present invention provides a method for gene assembly, comprising:

(a) providing a partially double-stranded nucleic acid (ds-NA) coupled to a solid support;

(b) providing a solution of single stranded nucleic acid (ss-NA) that is at least partially complementary to a single stranded portion of the ds-NA;

(c) contacting the ds-NA of step (a) with the solution of step (b) under conditions where at least some of the solution passes by the ds-NA under influence of a force exerted in a direction, such that (i) the ss-NA anneals to the single-stranded portion of the ds-NA, and (ii) the direction is reversed at least 1 time so that at least some of the solution passes by the ds-NA at least twice.

In another aspect the present invention provide a method for gene assembly, comprising:

(a) providing a partially double-stranded nucleic acid (ds-NA) coupled to a solid support;

(b) providing a solution of single stranded nucleic acid (ss-NA) that is at least partially complementary to a single stranded portion of the ds-NA;

(c) contacting the ds-NA of step (a) with the solution of step (b) under conditions where at least some of the solution passes by the ds-NA under influence of a force, such that (i) the ss-NA anneals to the single-stranded portion of the ds-NA, and (ii) a reduction in the force will reduce the amount of ss-NA that anneals to the single-stranded portion of the ds-NA, under otherwise constant conditions.

In another aspect, the present invention provides a method for gene or gene fragment assembly, comprising the following steps:

(a) providing a partially double-stranded polynucleotide coupled to a solid support;

(b) providing a solution of a single-stranded or a partially double-stranded polynucleotide that is at least partially complementary to a single stranded portion of the partially double-stranded polynucleotide of step (a); and (c) contacting the solid support of step (a) with the solution of step (b) under the influence of a force exerted in a direction where at least some of the solution of step (b) passes by the partially double-stranded polynucleotide of step (a);

wherein the single-stranded or partially double-stranded polynucleotide of step (b) anneals to the single-stranded portion of the partially double-stranded polynucleotide of step (a). Preferably the single-stranded or partially double-stranded polynucleotide of step (b) is partially double-stranded.

In a preferred aspect, the present invention provides a method for gene or gene fragment assembly, comprising the following steps:

(a) providing a partially double-stranded polynucleotide coupled to a solid support;

(b) providing a solution of a single-stranded or a partially double-stranded polynucleotide that is at least partially complementary to a single stranded portion of the partially double-stranded polynucleotide of step (a);

(c) contacting the solid support of step (a) with the solution of step (b) under the influence of a force exerted in one direction where at least some of the solution of step (b) passes by the partially double-stranded polynucleotide of step (a); and (d) reversing the direction of the force exerted in step (c) at least once so that at least some of the solution of step (b) passes by the partially double-stranded polynucleotide of step (a) at least twice;

wherein the single-stranded or partially double-stranded polynucleotide of step (b) anneals to the single-stranded portion of the partially double-stranded polynucleotide of step (a).

Preferably, the direction of the force exerted in step (c) is reversed multiple times so that the partially double-stranded polynucleotide of step (a) is repetitively contacted with the solution of step (b) and the single-stranded or partially double-stranded polynucleotide of step (b) is partially double-stranded. The force exerted to pass the solution by the solid support may be constant, which is preferred, or may be variable. In preferred embodiments of these aspects, the solid support is porous, and the solution of step (b) is required to pass through the pores multiple times.

F. Quantitative Assays for Evaluating the Synthesis Process

Two assay methods may be used to quantify two of the important steps in solid phase gene synthesis process: (1) the solid support binding capacity and (2) estimation of solid phase ligation efficiency. These assays are described next.

1. Assay for Solid Support Binding Capacity.

The solid support used in the present gene assembly is covalently joined to a universal linker oligonucleotide, preferably having about 17 nucleotides. The binding capacity of the solid support surface is determined by the following fluorescence-based assay. The solid support with the linker oligo is first hybridized with a fluorescence-labeled complementary oligo. The unhybridized label oligo is removed by excessive washing and the wash effluent is monitored by fluorescence. The hybridized label oligo is then released by denaturing at elevated temperature and its quantity measured by fluorometer. The solid support typically has a binding capacity of about 1-3 pmole/cm$^2$ on the surface.

2. Assay for Estimating Solid Phase Stepwise Ligation Efficiency.

Like other solid phase based reactions, enzymatic ligation on solid phase is less efficient and slower than solution based reactions (V. Chan, D. Graves, P. Fortina and S. McKenzie, *Langmuir*, (1997) vol. 13, 320-329; M. Shchepinov, S. Case-Green and E. Southern, *Nucleic Acid Research*, (1997) vol. 25, 1155-1161; H. Hakala, E. Maki and H. Lonnberg, *Bioconjugation Chem*. (1998) vol. 9 316-321; and P. Stevens, M. Henry and D. Kelso, *Nuclei Acid Research*, (1999) vol. 27, 1719-1727). Loss of diffusion of one of the reagents and increased steric hindrance greatly reduce the reagent concentration in the vicinity of reaction loci. In addition, solid phase ligation efficiency may also depend on the overall length of the DNA chain. Therefore ligation efficiency at early stages of the assembly when the DNA is short may not represent the ligation efficiency at later stages of the assembly when the DNA becomes long.

Using the assay as described herein, the effects of several parameters on ligation efficiency were evaluated. It was discovered that the following parameters have direct impact on solid phase ligation efficiency. Their relative importance may not be generalized in a simple order because each factor comes into play at different stages of the reaction.

Ligase concentration
Ligation time and temperature
Solution target concentration
Oligo duplex overhang length
Solid support material
Distance between the propagating end and the solid surface
Ionic strength in buffer
Mixing during incubation To assess the efficiency of solid phase ligations, the model system shown in FIG. 4 is used, which combines fluorescence labeling and gel image analysis.

Figures 4A, 4B, 4C, 4D:
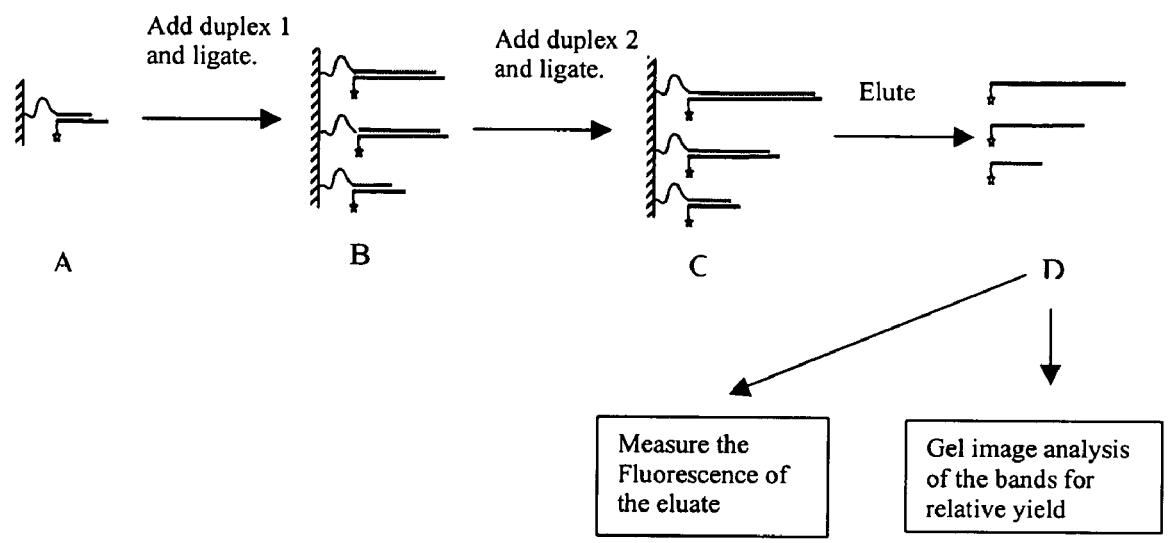

First, a fluorescently labeled oligo is hybridized to the linker oligo on the solid support producing a "sticky end" (FIG. 4A). Any unhybridized labeled oligo is removed by washing the solid support with annealing buffer. The first duplex that has the complementary "sticky end" is then annealed and ligated to the solid support tethered oligos in the presence of ligase and ligation buffer (FIG. 4B). Any unligated duplex 1 is removed by washing. The cycle is repeated for the second ligation cycle (FIG. 4C). Then the double stranded ligation products are denatured and the bottom strand eluted off the solid support (FIG. 4D). The solution containing the bottom strand is then analyzed on an acrylamide denaturing gel, and the intensity of each fluorescently labeled fraction is quantified by Kodak Digital Science™ 1D image analysis software. This method allows an estimation of the ligation efficiencies at various cycles in solid phase gene assembly.

The present invention, using flow-through porous materials as solid supports, has provided for the synthesis of 400 bp gene fragments with 35 base oligos in 12 cycles in 10-30% overall cumulative yield. This calculates as a theoretical per cycle yield of 85-90%.

G. Device for Gene Fragment and Gene Synthesis

1. Overview

In various aspects the present invention provides devices for gene or gene fragment synthesis, including devices that provide for automated solid phase gene or gene fragment assembly, as well as methods for using these devices in gene synthesis. In one aspect, the present invention provides a device for solid phase gene or gene fragment assembly, comprising:

i) a plurality of reaction chambers, each member of the plurality comprising
   (a) a solid support located within and spanning the chamber, the solid support comprising a porous region;
   (b) first and second orifices located such that a direct line from the first orifice to the second orifice passes by or through the solid support;
   (c) a first volume of the chamber located between the first orifice and the solid support; and
   (d) a second volume of chamber located between the second orifice and the solid support.

The device additionally preferably includes a valve and tubing system to provide fluid communication between the first orifice and a reservoir holding a solution of second oligonucleotide having a nucleotide sequence at least partially complementary to the nucleotide sequence of the first oligonucleotide. In operation, the solution of second oligonucleotide is preferably repetitively or continuously passed by or though the solid support. Thus, the present invention provides a method for solid phase gene assembly comprising:

i) providing a reaction chamber comprising
   (a) a solid support located within the chamber, the solid support being coupled to a first oligonucleotide; and
   (b) first and second orifices located such that a direct line from the first to the second orifice passes by or through the solid support;
ii) delivering a solution of second oligonucleotide through the first orifice and transporting the solution of second oligonucleotide by or through the solid support in the direction of the second orifice;
iii) repetitively or continuously passing the solution of second oligonucleotide by or though the solid support.

In another aspect of the invention, the present invention provides a device for automated solid phase gene or gene fragment assembly, comprising:

(a) a reaction block comprising a plurality of cavities adapted to hold a plurality of reaction vessels, wherein each reaction vessel, when present within a cavity, comprises a first orifice, a second orifice, and a solid support positioned within the interior of the reaction vessel between the first and second orifice; and
(b) a reagent delivery and mixing unit in fluid communication with the plurality of reaction vessels when present.

The reaction block of this device may additionally include one or more means to control or monitor the temperature of the reaction block; and/or one or more means to monitor the fluid level within a reaction vessel when present. The reagent delivery and mixing unit contains one or more pumps in fluid communication with one or more valves. In particular, a valve of the reagent delivery and mixing unit is positioned between the first orifice of a reaction vessel when present and a pump of the reagent delivery and mixing unit, where the valve is in fluid communication with the pump, the reaction vessel and one or more liquid storage containers such that a liquid in one of the liquid storage containers is transported from the liquid storage container through the valve into the reaction vessel by the action of the pump.

The automated device may additionally include one or more means to immobilize the plurality of reaction vessels within the plurality of the cavities of the reaction block.

Preferably, the automated device also includes a microplate holding apparatus, which may contain a temperature monitoring and control means. The device may additionally include a multi-microplate storage system, which may contain a temperature monitoring and control means, and/or a means to transport a microplate from the multi-microplate storage system to the microplate holding apparatus.

The device may additionally contain a microplate-well seal-piercing means.

The device may additionally contain a barcode reader to identify reagents (such oligos) and solutions used during the operation of the device and/or one or more means to analyze the products of the processes performed by the device, such as a spectrophotometer or a fluorescence plate reader.

Preferably the device contains a computer control unit, where the computer control unit executes pre-programmed commands to operate the various components of the device, including, but not limited to, the various temperature and control means, the means to monitor the fluid levels within a reaction vessel, the reagent delivery and mixing unit, the multi-microplate storage system, the means to transport a microplate from the multi-microplate storage system to the microplate holding apparatus, the microplate well seal-piercing means, and/or the means to analyze the products of the processes performed by the device.

In a preferred embodiment, a device for automated gene fragment or gene assembly of the invention comprises:

(a) a reaction block comprising a plurality of cavities adapted to hold a plurality of reaction vessels, wherein each reaction vessel, when present within a cavity, comprises a first orifice, a second orifice, and a solid support positioned within the interior of the reaction vessel between the first and second orifice;
(b) a reagent delivery and mixing unit in fluid communication with the plurality of reaction vessels when present;
(c) a microplate holding apparatus;
(d) one or more means to immobilize the plurality of reaction vessels when present within the plurality of cavities of the reaction block;
(e) one or more means to monitor or control the temperature of the reaction block, the multi-microplate storage system or the microplate holding apparatus;
(f) a computer control unit, where the computer control unit executes pre-programmed commands to operate the various components of the device;
(g) optionally, a multi-microplate storage system;
(h) optionally, a means to transport a microplate from a multi-microplate storage system to a microplate holding area; and
(i) optionally, a microplate well seal-piercing means.

2. Reaction Vessels

In one aspect, gene or gene fragment synthesis according to the present invention is performed within a reaction vessel. Each reaction vessel, when present in a cavity, has an interior solid surface to which oligonucleotide is coupled. FIGS. 5A, 5B, 5C, 5D and 5E illustrate five configurations of the solid surface. In FIG. 5A, the solid surface is a fiber that extends from the interior wall of the vessel. In FIG. 5B, the solid surface is a sleeve that is adjacent to the interior wall of the vessel. In FIG. 5C, the solid surface is a porous plug that spans the width of the vessel, effectively dividing the interior of the vessel into two sub-chambers. In FIG. 5D, two rigid porous barriers span the width of the reaction vessel and define a space located between the barriers which is filled with beads. The beads are the solid support to which the oligonucleotide is coupled. In FIG. 5E, the solid surface is a brush that is suspended in the reaction vessel, where the brush may be rotated through the solution by operation of a motor. Other surface configurations may alternatively be utilized.

Figure 6A:
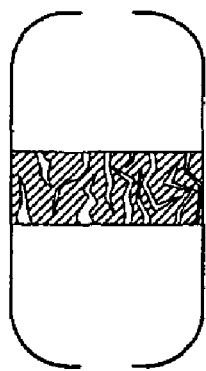
FIGS. 6A-6C illustrate relative arrangements of orifices in a reaction vessel that may be used in the present invention.
Figure 6B:
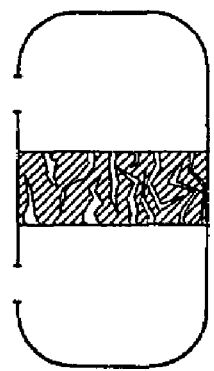
Figure 6C:
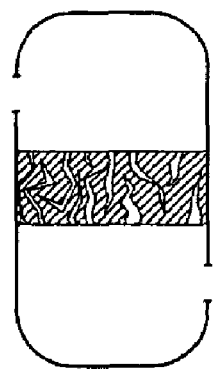

In addition to containing oligonucleotide coupled to a solid support, each reaction vessel has two orifices. Each orifice can be used to transfer solutions and reagents into and out from the reaction vessel. The orifices should be positioned so that a direct path from one orifice to the other orifice proceeds past or through the solid support. Using the reaction vessel of FIG. 5C with a porous plug as the solid support as an example, FIGS. 6A, 6B and 6C show three possible placements for the two holes (orifices). In FIG. 6A, the holes are placed at the top and bottom of the reaction vessel, with the porous plug in the middle. In FIG. 6B, the holes are placed one above the other, on the same side of the reaction vessel. In FIG. 6C, the holes are placed on opposite sides of the reaction vessel. In each case, one hole is placed above the porous plug and the other hole is placed below the porous plug so that a direct line between the two holes passes through the porous plug. The term "flow through reactor" refers to a reaction vessel that has two holes positioned so that a direct path from one hole to the other hole proceeds past or through the solid support.

Figure 7A:
FIGS. 7A-7C depict three reaction vessels that may be used in the present invention.
Figure 7B:
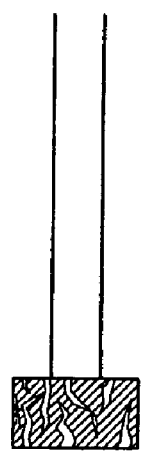
Figure 7C:

In another aspect, the solid support is located at a termini of the reaction vessel, i.e., at or near one of the orifices. This is illustrated in FIGS. 7A, 7B and 7C wherein the solid support is a porous plug. In FIG. 7A, the porous plug is located at the end of, but inside of, the reaction vessel. In FIG. 7B, the porous plug is located at the end of, but outside of, the reaction vessel. In FIG. 7C, the reaction vessel has a tip, and the porous plug is located within this tip.

A similar system is described in U.S. Pat. No. 5,437,979, which may be utilized to perform the method of the present invention. The system of the '979 Patent utilizes a pipette tip to hold liquid drawn from a receptacle, where the tip retains a chemical species immobilized on a solid support. As applied to the present invention, the first oligonucleotide may be immobilized in the pipet tip, and the solution of second oligonucleotide may be placed in the receptacle. The solution of second oligonucleotide is drawn into the pipet tip, then expelled, and this process is repeated at least once, preferably multiple times. The '979 Patent discloses to use one or two porous frits to hold the solid support in place. When adapted for use in the present method, two porous frits will be needed in order to immobilize the beads.

The use of pipet tips is not a preferred embodiment of the method of the present invention because pipet tips secured in place by friction fit, such as disclosed in the '979 Patent, often leak at the junction where the tip joins the rest of the apparatus. Even small leaks can be troublesome to the method of the present invention because of (1) the multiple times the solution of second oligonucleotide passes across the solid support, and (2) the multiple times new solutions of oligonucleotide and wash solutions are introduced to the reaction vessel. Pipet tips are designed for one or two time use, not for extended use. Thin-walled pipet tips often distort under extended use, and the friction fit they are intended to have with a pipet is lost.

As mentioned previously, a preferred solid support material for use in the devices and methods of the present invention is porous polyethylene with 5-35 μm pores. This material is commercially available from several manufacturers such as Porex Technologies (Fairburn, Ga.) and Porvair Advanced Materials (Hendersonville, N.C.). Both companies are capable of molding the frits directly. The raw porous polyethylene frits may be subjected to plasma treatment in order to introduce amine groups to the surface. $4^{th}$ State, Inc. of Belmont, Calif. is one of several vendors that advertise plasma treatment services. After plasma treatment the support will be press fitted into the reaction vessels.

Preferably, the solid support is coupled to a universal oligo through a linker group. For example, a 5'-carboxyl-terminated-PEGylated linker oligo may be coupled to the solid support as discussed above. The oligo coupling and assay reactions are all run at room temperature using the same reagents across all the columns. The gene fragment and gene solid phase assembly station described below can be used to couple the universal oligo (plus linker, if desired) to the solid support.

The use of a universal oligo and a bridge oligo with the reaction vessels of the devices of the present invention is very useful because it allows the reaction vessels to be repetitively used to prepare a new gene or gene fragment, and this reusable characteristic can be accomplished robotically. That is, it is not necessary for a person to replace a solid support with a new solid support in the reaction vessels of the devices of the present invention when one gene fragment is complete and the assembly of another gene fragment begins. The gene fragment can be simply washed off the solid support, leaving the universal oligo bound to the support, and the process of gene assembly initiated by the addition of an appropriate bridge oligo to the solid support/universal oligo. Thus, in one aspect, the present invention provides for the sequential preparation of multiple gene fragments from the same reaction vessel, wherein a gene fragment is washed from the solid support within the reaction vessel, and then a new bridge oligo is introduced to that solid support to re-initiate gene fragment assembly.

In a preferred embodiment, the devices of the invention incorporate means to monitor the level of fluid in each reaction vessel. Such means are well known in the art (see, e.g., U.S. Pat. No. 5,539,386) and may be incorporated into the reaction block of the devices of the present invention.

3. Reagent Delivery and Mixing Unit

Each of the reaction vessels of the invention is in fluid communication with one or more pumps. The same pump may be in fluid communication with all or a portion of the plurality of reaction vessels. In one aspect, a single pump is in fluid communication with all of the plurality of reaction vessels. This aspect is advantageous in that the expense of purchasing and maintaining multiple pumps is reduced. In another aspect, each reaction vessel is in fluid communication with a separate, unique pump. This aspect is advantageous because it affords maximum flexibility of operation, i.e., each reaction vessel can be individually controlled, and all of the reaction vessels need not be subjected to the same operation conditions. Having each reaction vessel in fluid communication with a unique pump is also advantageous because malfunction at one reaction vessel has little or no impact on the operation of the other reaction vessels. One of the two orifices that are present in each reaction vessel is in fluid communication with a pump.

In order to achieve gene assembly according to the present invention, a solution of a second oligonucleotide is needed. This solution of second oligonucleotide is added to the reaction vessel and allowed to contact the first oligonucleotide which is bound to the solid support. The solution of second oligonucleotide will enter the reaction vessel via one of the vessel's two orifices. A pump provides the force by which the solution of second oligonucleotide is moved into the reaction vessel.

Under action of the pump, the solution of second oligonucleotide within the reaction vessel is transported toward the reaction vessel's second orifice. In the course of this transport, the solution of second oligonucleotide contacts the solid support having first oligonucleotide bound thereto, and the first and second oligonucleotides thereby come into contact with one another.

In one aspect, an important feature of the gene fragment and gene assembly method of the present invention is that the solution of second oligonucleotide is made to travel from the first orifice, across or by the solid support toward the second orifice, and after allowing the first and second oligonucleotides to contact one another, the solution reverses direction. That is, after traveling in a direction from the first orifice to the second orifice, the solution is caused to travel in the opposite direction, i.e., from the second orifice toward the first orifice. Thereafter, the solution reverses direction yet again, and repeats its travel in a direction from the first orifice toward the second orifice. This change in direction is repeated multiple times, so that the solution is passed back and forth, back and forth, etc., across the solid support having the first oligonucleotide bound thereto. This process of passing the solution back and forth across the solid surface will be referred to herein as repetitive flow-through contact.

The present inventor has surprisingly discovered that repetitive flow-through contact increases the yield of gene assembly. That is, repetitive flow-through contact increases the number of first oligonucleotides that become bound to second oligonucleotides. The mechanism of action behind this surprising discovery is not yet known for certain, and has been discussed previously herein. Basically, the mechanism of gene assembly according to the present invention entails having the first oligonucleotide anneal to the second oligonucleotide according to standard nucleotide base-pairing rules. For this annealing process to occur, the first oligonucleotide needs to be in a form sufficiently extended that its nucleotide bases are exposed to, and able to come into contact with, the bases of the second oligonucleotide. The repetitive flow-through contact aspect of the present invention is believed to encourage extension of the first oligonucleotide to thereby allow and encourage annealing between the bases of the first and second oligonucleotides.

Repetitive flow-through contact is considered to be particularly important when the first oligonucleotide is bound inside the pores of a porous solid support. A porous solid support is a preferred solid support according to the present invention because it provides for a large surface to volume ratio, thereby allowing a relatively large number of first oligonucleotides to be bound to a relatively small volume of solid support. In this situation, it is considered important to provide continuous, or at least frequent flow of solution inside the pores of the solid support. This frequent flow is thought to encourage the first oligonucleotide to remain in a relatively extended form and thereby be relatively more reactive with second oligonucleotide.

Figure 8A:
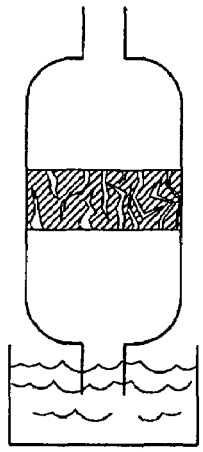
FIGS. 8A-8E illustrate a repetitive flow-through mixing process of the present invention.
Figure 8B:
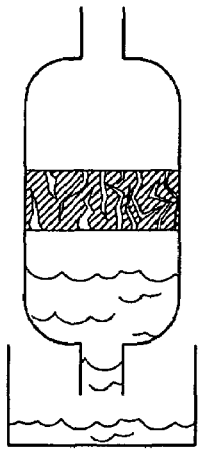
Figure 8C:
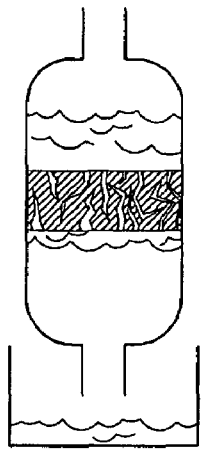
Figure 8D:
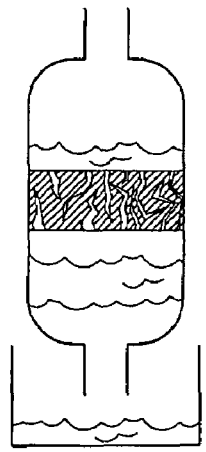
Figure 8E:
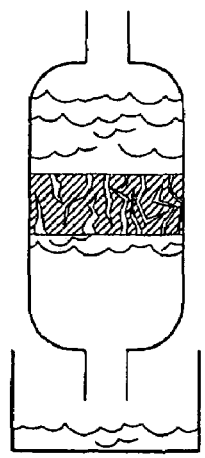

Repetitive flow-through contact is illustrated in FIGS. 8A-8E, again using the reaction vessel of FIG. 5C for illustration purposes. In FIG. 8A, the reaction vessel is elongated and the solid support is a porous matrix that spans the reaction vessel and is located approximately mid-way along the length of the reaction vessel. This porous solid support, or frit, divides the reaction vessel into two sub-chambers, i.e., first and second sub-chambers. Under action of a pump, as illustrated in FIG. 8B, a solution of the second oligonucleotide is drawn from a reservoir though the first orifice of the reaction vessel and into the reaction vessel. The solution is drawn into the first chamber until it entirely bathes the solid support, and until further movement toward the second orifice will expose the solid support to air in the first chamber, which is the state illustrated in FIG. 8C. In this particular embodiment, the solution of the second oligonucleotide is held in place by one or more of vacuum between the pump and the solution of the second oligonucleotide and capillary forces that inhibit the solution from flowing back out the first orifice. Thereafter, the force exerted by the pump pushes the solution of second oligonucleotide back toward the first orifice. Preferably, the solution of second oligonucleotide continues to entirely bathe the solid support. This is illustrated in FIG. 8D. FIGS. 8C and 8D illustrate repetitive flow-through contact. Repetitive flow-through contact can be continued, as illustrated in FIG. 8E, where the force exerted by the pump is reversed and draws the solution of second oligonucleotide back toward the second orifice.

Figure 9:
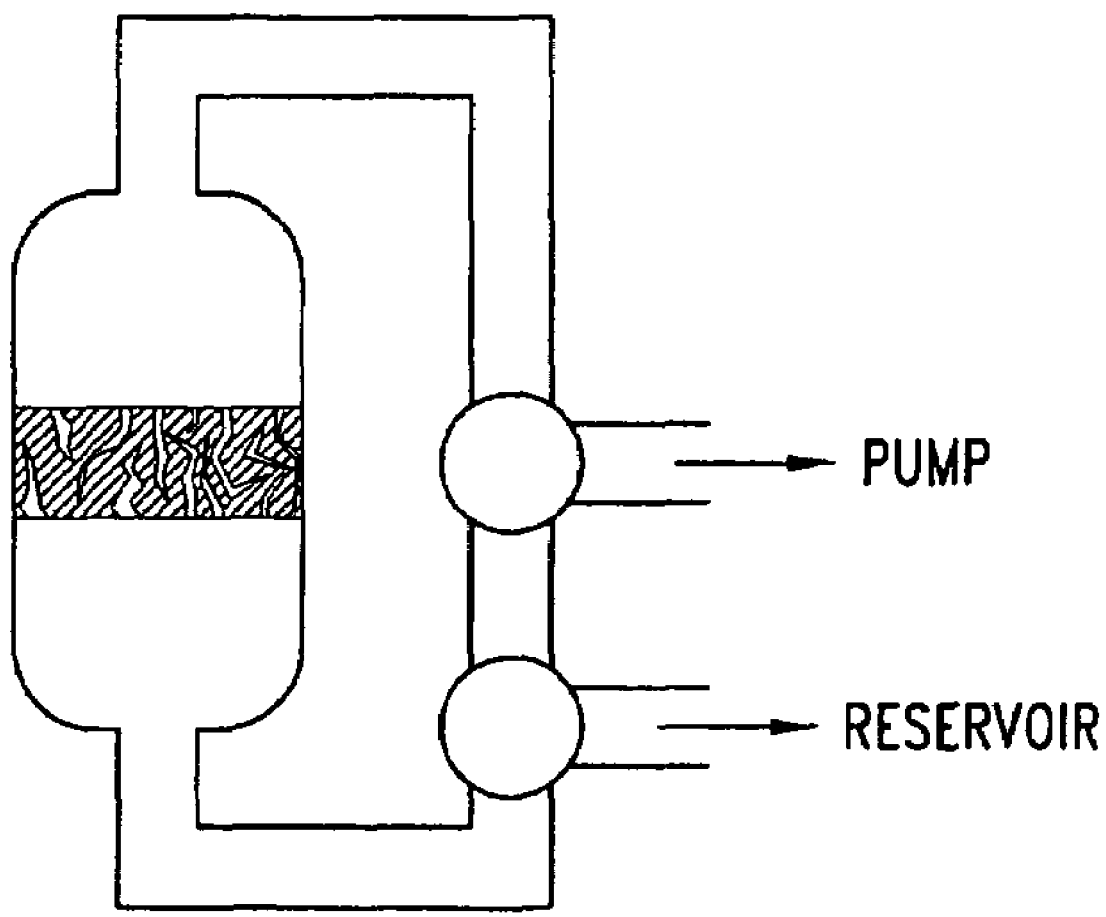
FIG. 9 illustrates a device that may be used to provide continuous flow-through mixing according to the present invention.

In another aspect, the method of the present invention provides a variation on repetitive flow-through contact that will be referred to herein as continuous flow-through contact. In this mode, the solution of second oligonucleotide is continuously passed from the first orifice across the solid support and through the second orifice. In order to minimize the amount of solution of second oligonucleotide needed to achieve continuous flow-through contact, the solution may be recycled as shown in FIG. 9, which utilizes the reaction vessel of FIG. 5C for illustrative purposes. As shown in FIG. 9, a reaction vessel is provided having a porous solid support, or frit, spanning the sides of the reaction vessel. The second oligonucleotide is introduced into the reaction vessel from a reservoir, and then the valve to the reservoir is shut off. A pump then causes the solution of second oligonucleotide to continuously cycle through the reaction vessel in either a clockwise or counterclockwise direction. The direction of flow of the solution may be occasionally or periodically reversed if desired, to thereby provide repetitive flow-through contact.

In a preferred device of the invention, the reaction vessel is a column fitted with a porous solid support, or frit (FIG. 10A). In this design, the reaction vessel is fitted with a frit and a Luer fitting on the top that is coupled to a programmable syringe pump and connects to buffer reservoirs through a 3-way switch valve. With this reaction vessel and syringe pump configuration, reagents (oligos and ligase) are drawn through the bottom of the reaction vessel from a microplate positioned beneath the reaction vessel. Mixing of the reagents within the reaction vessel is accomplished by pumping up and down with the same syringe pump and flowing the solution through the porous solid support. Washing buffer is delivered from the top of the reaction vessel through the switch valve. Waste is washed from the reaction vessel by pumping solution through the reaction vessel into waste collection vessels positioned beneath the reaction vessel. With such a setup, a programmable syringe pump can handle all the steps in gene fragment assembly process. This design may be extended to a multi-column device as illustrated in FIG. 10B.

The reagent delivery and mixing unit is an important element in the automated solid phase gene and gene fragment assembly station. This is the component of the device containing the pumps, tubing and valves required to deliver the reagents and appropriate solutions and buffers to the appropriate reaction vessels. A preferred component of the unit is a programmable parallel syringe pump unit that controls both the reagent delivery and mixing operations. This unit is able to create a consistent pressure difference to deliver small volumes of oligo solutions uniformly across the entire solid support surface. This unit also provides a continuous flow of reagents across and through the solid supports in the reaction vessels in the device. This unit also provides the means by which the direction of this continuous flow may be reversed.

In one aspect of the invention, each reactor vessel is coupled to a separate syringe from the top of the reaction vessel. Alternatively, two more of the reaction vessels may be coupled to a single syringe. At the beginning of each reaction cycle, the oligos in a multi-well microplate are positioned under the reaction block and each oligo solution is withdrawn into the reaction vessel through an orifice at the bottom of the reaction vessel. Then the syringe pump is programmed to pump up and down continuously at a certain rate and volume displacement so that the solution flows through the porous solid support back and forth constantly. At the end of the cycle, the solution is flushed from the reaction vessel to a waste collector. After each annealing reaction, a repeated wash cycle is done with fresh washing buffer added from the top of the reaction vessel through a switching valve between the syringe pump and the reaction vessel (FIG. 10).

The use of an individual syringe for each reaction vessel provides reliable and consistent control of the flow rates and volumes of solution and fluid in each reaction vessel and across the entire reaction block. With designs based on a single syringe pump or a vacuum chamber for the entire reaction block, it is more difficult to ensure that every reaction vessel is uniform, however, this approach may also be used.

4. Reaction Block

Figure 10C:
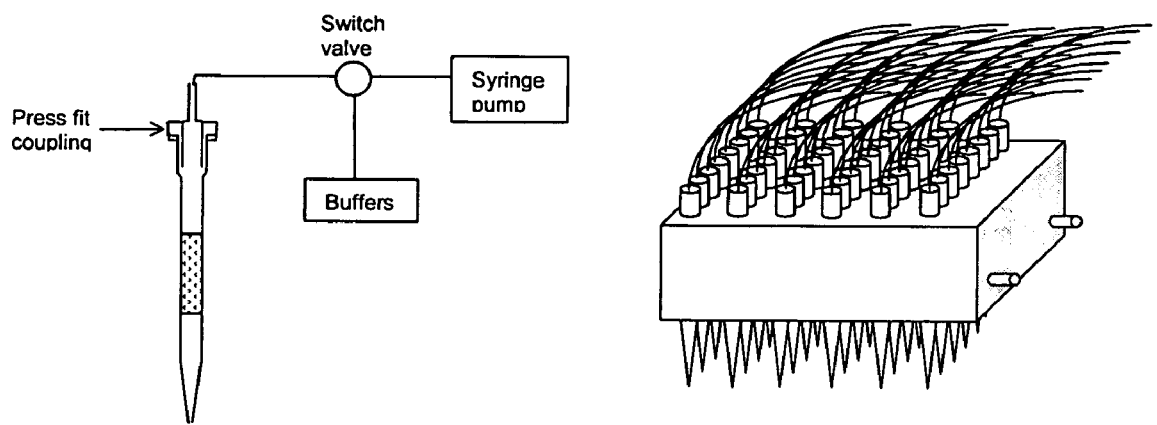
FIG. 10C illustrates a reaction block containing a plurality of reaction vessels within a plurality of cavities that may be used in gene synthesis according to the present invention.
Figure 10C:
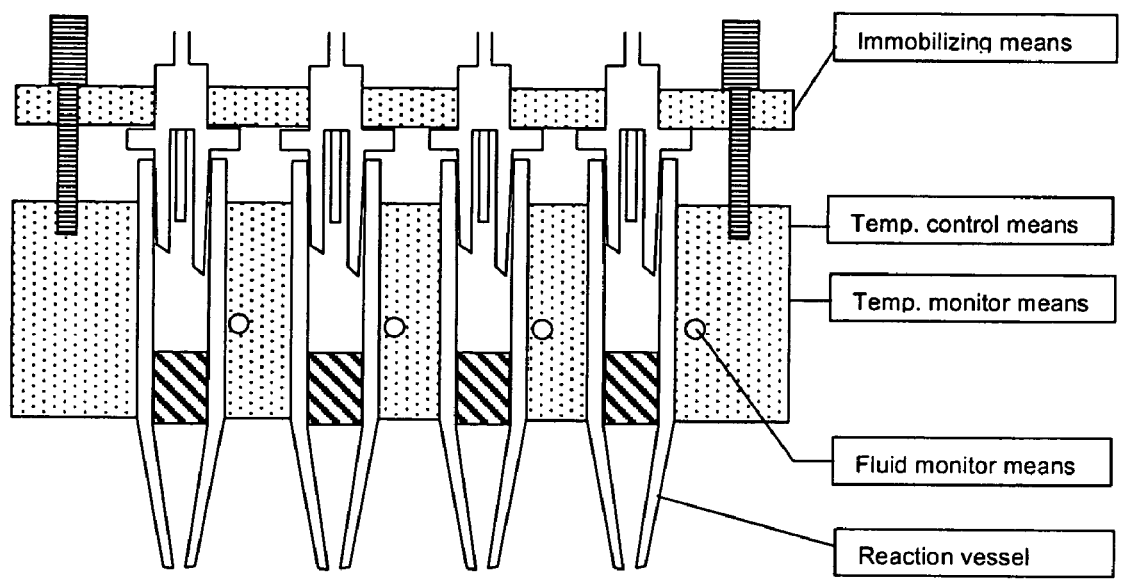

In one aspect, the solid phase gene fragment or gene assembly systems of the invention comprises a reaction block comprising a plurality of cavities adapted to hold a plurality of reaction vessels, as illustrated in FIG. 10C. In one embodiment, the reaction block contains a means to allow for individual temperature control for each reaction vessel. In another aspect, the reaction block contains a means to allow for uniform temperature control across the entire block. In another embodiment, the reaction block contains a means to monitor the fluid levels within each reaction vessel. The central element of the reaction block is the reaction vessel (FIG. 10B and FIG. 10C) wherein each reaction vessel contains a solid support therein. An reaction block of this type may be manufactured for the purposes of this invention by a fabricator in business for this purpose. The reaction vessels may be made from a moldable plastic that is inert, autoclaveable, and has adequate heat transfer characteristics and low DNA adsorption. The molded part is preferably dimensionally stable so that the reaction vessel may be held in place with a friction fit into the reaction block and the solid phase frit may in turn be held in place with a friction fit within the vessel. The top of each reaction vessel preferably has a coupling joint that connects and disconnects easily to the reagent delivery and mixing unit tubing. Each reaction vessel preferably has a pointed tip that can reach the bottom of standard 96-well microplate to pick up small volume of reagents. The volume of the reactor vessel is preferably about three times the bulk volume of the solid support fitted therein. The reaction block that holds the plurality of reaction vessels preferably arranges the reaction vessel in a manner compatible with 96-well microplate formats to facilitate upstream and downstream automation. The reaction block preferably includes temperature control and monitoring means(e.g., +/−1° C. or +/−2° C., ramp rate of 10° C. per minute). A schematic diagram of a reaction, and a block of reactions, is shown in FIG. 10B and FIG. 10C.

The reaction vessels may be held in place within the reaction block by an immobilizing means as illustrated in FIG. 10C. Such means serves to secure the reaction vessels within the cavities of the reaction block to prevent their movement during the operation of the device, particularly when reagents and solutions are being pumped into and/or through a reaction vessel. Preferably the immobilizing means is securely attached to the reaction block and to the coupling joint present at the top of each reaction vessel.

5. Temperature Control

The reaction blocks have heating and cooling capability from ambient temperature to 100° C. in +/−1° C. precision. The temperature control and monitoring unit is preferably programmable with an interface to a central computer control unit. The reaction block and the temperature control and monitoring unit may be fabricated by any of a number of fabricators, e.g., J-KEM Scientific (St. Louis, Mo.).

6. Multi-Microplate Storage System, Robotic Plate Transport System, Microplate Holding Apparatus, and Microplate-Well Seal-Piercing Means In one aspect of the invention, a multi-microplate storage system and robotic microplate transport system is incorporated into the overall design of the device. This piece of equipment serves to store and deliver reagents (oligos) to each cycle of the solid phase annealing reactions. The robotic microplate transport system serves to transport individual microplates to and from a microplate holding apparatus. The microplate holding apparatus serves to position one or more microplates underneath the reaction block of the device in such a way as to allow delivery of the reagents contained in the individual wells of the microplate into the reaction vessels in the reaction block. Preferably, prior to the storage of the microplates in the multi-microplate storage system, the wells of the individual microplates are sealed by a sealant material to prevent evaporation or degradation of the reagents contained in the wells of the microplates or to prevent contamination of the reagents by other reagents and solutions during the delivery process. Such seals must be pierced or punctured, preferably by a piercing means, before the reagents contained in the wells of the microplate can be delivered to the appropriate reaction vessel during the gene fragment and gene assembly process. Such piercing or puncturing means are commercially available and can easily be incorporated into the device of the invention. Preferably the piercing means pierces or punctures the seals of only those wells that contain reagents that are required at the time. In an alternative embodiment, the sealant material used to seal the wells of the microplate self-seals after the seal is pierced or punctured by the seal piercing means in order to allow for the re-use of the reagent contained in the well without further degradation, evaporation or contamination. In addition, it is preferred that the temperature of the multi-microplate storage system and the microplate holding apparatus is monitored and controlled within desired ranges, preferably by one or more temperature monitor and control unit that is controlled by a central computer unit.

Assembly of 48 400-bp gene fragments involves about 10 annealing cycles. The oligos for these cycles may be supplied in 10 microtiter plates. Since the entire batch cycle will run up to about 2 days at a time, the oligos have to be kept in waiting mode without significant evaporation and degradation. One solution is to have a temperature and humidity controlled multi-microplate storage system coupled with a microplate transport robotic arm. Such equipment is currently available through various vendors.

Arranging the reaction vessels into a reaction block along the lines depicted in FIG. 10B is particularly desirable because the arrangement is complementary to the arrangement of wells in a multiwell microtiter plate. In one aspect of the invention, all of the reagents needed to make a gene or gene fragment are placed into a single 96-well microplate, and the reactor block has eight reactors. This provides up to 12 independent sets of wells from which reactants (e.g., first oligo/first duplex, second oligo/second duplex, ligase, etc.) may be delivered to the reaction vessel. The washing buffer is located in a separate reservoir, and accessed via tubing and pump action.

7. Develop Process Quality Control Protocols

Means by which to analyze the products or processes performed by the device are desirably included at each critical step in the gene fragment and gene assembly process. Such quality control protocols are well known in the art or described herein, such as the assays for solid support binding capacity and ligation efficiency. The final eluted gene and gene fragments may be verified by well known gel electrophoresis procedures. In addition, such means may be included within the device itself, such as a spectrophotometer or a fluorescence plate reader. Such instruments are well known in the art and could be incorporated within the device as desired.

8. Automated Synthesis

In one aspect, the present invention is directed to automated solid phase gene assembly system using a solid phase gene process. This system includes several important components, as illustrated in FIG. 11. In its simplest configuration, the solid phase gene assembly station comprises a reaction block as described herein, a temperature control unit, a reagent delivery and mixing unit, a microplate holding apparatus and a central computer control unit. The station may also comprise a multi-microplate storage system and a microplate robot for transporting the microplates to and from the microplate holding apparatus. The station may also comprise a microplate-well seal-piercing means to allow access to the reagents contained in the wells during the assembly process. The station may also incorporate a barcode reader and analytical instruments, such as a spectrophotometer and a fluorescence plate reader.

The reaction block holds the individual reaction vessels and maintains temperature of each reaction cycles. The multi-microplate managing system keeps and manages the oligo supplies for all the cycles involved in building the 400 bp gene fragments. The reagent delivery and mixing unit includes the pumps, valves and tubing required to deliver the various reagents and solutions of the assembly process and will control the addition and removal of oligos and buffers as well as the mixing of the reagents during the assembly process. The central computer control unit is programmable and executes pre-programmed commands to operate the various components of the station, including the temperature control unit, the multi-microplate storage system (coupled with the microplate robot), the reagent delivery and mixing unit and the seal-piercing means.

The following examples are provided by way of illustration and not limitation. Methodology for cloning nucleic acid sequences and determining the sequence of those nucleic acids is well known to those skilled in the art of the present invention. Exemplary techniques are described, for example, in the following laboratory research manuals: Sambrook et al., "Molecular Cloning" (Cold Spring Harbor Press, 3rd Edition, 2001) and Ausubel et al., "Short Protocols in Molecular Biology" (1999) (incorporated herein by reference in their entireties), where these reference texts may be referred to in order to obtain additional details for carrying out procedures as described herein.

EXAMPLES

Example 1

Building a 310-Base Pair Gene on a Particulate Solid Support

Acid-Treatment of Resin

Aminomethylated polystyrene resin (3 grams, ~100 micron in diameter, Aldrich) was mixed with 4 ml of concentrated hydrochloric acid (HCl) and 12 ml of water in a glass scintillation vial. The resin was stirred in the acidic solution at room temperature for 1.5 hr. The acid-treated resin was washed with water until the pH of the filtrate reached 5-6. This procedure was repeated on a second batch of amionmethylated polystyrene resin using acetic acid in place of concentrated HCl, and dimethylformamide (DMF) in place of water, as the acid-treating conditions. The batches of acid-treated aminomethylated polystyrene resin were stored as wet solids at 4° C.

The two washed, acid-treated resins were qualitatively tested for surface amine content using tri-nitrobenzene sulfonic acid (TNBSA). Untreated resin was tested in the same manner, to provide a control experiment. The results are shown in Table 1. When the resin turned a dark orange color, this indicated a high amine content on the surface. When the resin turned a light yellow color, this indicated a low amine content on the surface. Under these test conditions, the untreated resin barely turned yellow. However, the longer the untreated resin was maintained at 40° C., the more yellow coloration became apparent.

TABLE 1

| SURFACE AMINE CONTENT ON AMINOMETHYLATED POLYSTYRENE RESIN | |
|---|---|
| Acid treatment method | TNBSA test color of the resin |
| Untreated resin | no noticeable color change |
| Acetic acid/DMF | slightly yellow |
| Concentrated HCl/H$_2$O | dark orange |

Resin-Oligo Coupling

The aminopolystyrene resin that had been treated with concentrated HCl and then washed with water (as prepared in part A above) was covalently coupled to linker oligo as described below. The linker oligo contained an Oligonucleotide portion comprising 17 nucleotide bases, a spacer group, and at its 5' end a primary amine group, as illustrated in the following structure wherein m is selected from integers within the range of 1 to 50, n is selected from integers within the range of 1 to 20, and p is selected from 0 and integers within the range of 1 to 10.

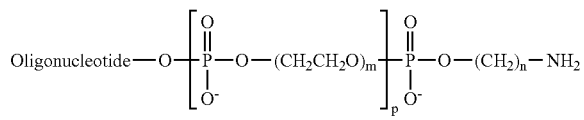

The spacer used in the present experiments was either a single polyethylene glycol unit flanked by two phosphate groups as indicated by the foregoing structure where p=1, or two polyethylene glycol units separated by a phosphate group and flanked by two phosphate groups, as shown by the foregoing structure where p=2. These linker oligos were prepared by Trilink Biotechnologies, Inc. (San Diego, Calif., USA; @trilinkbiotech.com). The linker oligos were coupled to separate batches of resin using cyanuric chloride chemistry as described below. The same process may be employed with linker oligos having more than two polyethylene glycol units.

A selected linker oligo was dissolved in deionized water to form a 1 mM solution. To prepare cyanuric chloride activated linker oligo, 20 microliters (20 nmoles) of the linker oligo solution was mixed with 50 microliters of 1M borate at pH 8.4. To this mixture was added 14 microliters of a freshly prepared cyanuric chloride solution, which was prepared by dissolving 30.8 mg cyanuric chloride (Aldrich Chemicals, recrystallized from toluene) in 580 microliters acetonitrile (Allied Signal). The reaction was carried out at room temperature for 40 min. The product mixture was eluted from a Sephadex G-50 (Sigma) gel column with 0.1 M borate at pH 8.4 to remove excess cyanuric chloride. The cyanuric chloride-activated linker oligo was lyophilized and then dissolved in 80 microliters of deionized water. The recovery of the oligo was 14 nmoles.

Before coupling the cyanuric chloride-activated linker oligo to the treated and washed aminopolystyrene resin (the solid support), the solid support (0.5 ml in packed volume) was treated with 1 ml 0.5 M borate at pH 8.4 for 5 minutes, and then the borate solution was removed by filtration. The cyanuric chloride-activated linker oligo was then added to the solid support and the mixture maintained at room temperature for 1 hour. After this reaction period, the liquid was removed from the solid by filtration, and the solid resin was washed with 2 ml 0.1 M borate at pH 8.4 three times before performing the capping reaction described below. Each washing step consisted of contacting the washing solution with the solid support, and after agitation of the mixture, the liquid was removed from the solid by filtration.

Capping Reaction

The unreacted —$NH_2$ groups on the aminomethylated polystyrene resin were capped with acetic anhydride by mixing the solid support with 100 microliters 0.5 M borate, 500 microliters 1-methyl-2-pyrrolidinone (NMP, Aldrich Chemicals) and 500 microliters acetic anhydride (Fisher Scientific) at room temperature for 1.5 hours. The liquid was removed from the solid by filtration, and then the solid support was washed with 2 ml 1 -methyl-2-pyrrolidinone/water (50/50 v/v) three times, 2 ml 1 mM EDTA three times, 2 ml 10 mM Tris/1 mM EDTA/0.1% sodium dodecylsulfate solution three times and finally 2 ml 10 mM Tris/2 mM EDTA three times. Each washing step consisted of contacting the washing solution with the solid support, and after agitation of the mixture, the liquid was removed from the solid by filtration. The resin was stored at 4° C.

Assay the Amount of Linker Oligo on the Solid Support by Molecular Beacon

Molecular beacon technology is well known as a sensitive method to detect a specific nucleotide sequence in a solution-phase oligonucleotide (i.e., an oligonucleotide dissolved in solution). According to the current invention, we have successfully applied molecular beacon technology to directly assay the amount of linker oligo that is immobilized on a solid support. This method avoids overestimating the linker oligo content of the solid support as occurs when employing assay techniques that are commonly used for other solution-based determinations.

The molecular beacon (prepared by Trilink) used according to the present assay has a central portion composed of 17 nucleotides that have a base sequence complementary to the base sequence of the nucleotides that are present in the linker oligo. Flanking this central portion on either end are 6 nucleotide bases that are complementary to each other, i.e., the 6 bases on one end of the beacon are complementary to the 6 bases on the other end of the beacon. At its 3' end, the beacon is linked a fluorescent group (specifically, FAM), while at its 5' end the beacon is a quencher DABCYL. The molecular beacon by itself, i.e., when not in the presence of an oligonucleotide that is complementary to the central portion of the beacon, does not produce significant fluorescence signal.

Before performing the assay, 15 microliters (packed volume) of the solid support that has been coupled to the linker oligo was washed with 1 ml 2×SSPE buffer (0.3 M NaCl, 0.02M mono-sodium phosphate, 2 mM EDTA at pH 7.6). Then 5 microliters of the molecular meacon solution (10 pmoles/microliter) was added to the solid support. The mixture was placed under gentle shaking at room temperature overnight. Then the solid support was washed with a SDS wash solution (0.05% sodium dodecylsulfate, 0.5 M NaCl, 5 mM Tris, 1 mM EDTA) six times at 1 ml volume of washing solution each time.

The washed solid support was suspended in solution by adding 170 microliters 32 wt % sucrose. The sugar solution keeps the solid polystyrene spheres suspended in solution without settling for 10 minutes or longer. The stable solid sphere suspension was directly placed in a fluorimeter. Its fluorescence signal intensity was compared with a control sample suspension, which contained the same amount of solid support resin but without any molecular beacon. The net gain in fluorescence signal was converted to picamoles (pmoles) by using a standard calibration line with known amounts of molecular beacon that were annealed to the same linker oligo in solution, i.e., the linker oligo was dissolved in several solutions and various known amounts of molecular beacon were added to these solutions. According to this assay, the above described polystyrene resin contained 1-2 pmoles linker oligo per microliter of packed volume of resin.

Oligonucleotide Design

The nucleotide sequence of a target polynucleotide (a gene) having 310 base pairs with a CTTTC sequence at both 3' ends was obtained, as illustrated in FIG. 12A. This gene was conceptually broken down into a family of short oligonucleotide sequences (oligos) as identified in FIG. 12B where the letters A through U provide names for specific oligos, and the numbers (e.g., 30, 33, 35) designate the number of nucleotides present in a particular oligo. As shown in FIG. 12B, oligos in the interior of the gene each consisted of 33-35 bases while oligos near the ends of the gene (oligos K and U) were somewhat shorter. The breaks between oligos were designed to occur such that each interior oligo overlapped with two partially-complementary oligos in the complementary strand over a length of 15-17 nucleotides. The oligos that formed the ends of the gene were designed to overlap with their complementary oligo over a length of 15-16 nucleotides. After these oligos were designed, they were synthesized by standard solid-phase technology.

In order to achieve synthesis of the gene, two "bridge" oligos were designed and synthesized. These bridge oligos are designated "bridge oligo L" (in FIG. 12C) and "bridge oligo R" (in FIG. 12D). Each bridge oligo consists of three regions of nucleotides, as defined by the function these regions perform in the polynucleotide assembly process. Each bridge oligo contained a contiguous set of nucleotides, termed a "gap sequence" of nucleotides, that lies between a first contiguous sequence of nucleotides that anneals to the first region of the universal oligo, and a second contiguous sequence of nucleotides that anneals to the first region of the first oligo that will be incorporated into the target polynucleotide. This gap sequence of nucleotides does not anneal to either the first region of the universal oligo or the first region of the first oligo. In fact, the primary purpose of the gap sequence is to assure that the first region of the universal oligo does not come into ligatable vicinity to the first region of the first oligo. Two oligos that are each partially annealed to another oligo, will ligate to each other only if they are in "ligatable vicinity" to one another. Essentially, this means that there cannot be a gap between two oligos both annealed to an oligo, in order for the two oligos to be in "ligatable vicinity" to one another.

The gap sequence is at least one nucleotide in length. Preferably, in order to further reduce the likelihood that the universal oligo will ligate to the first oligo of the target polynucleotide, the gap sequence is more than one nucleotide in length, e.g., 2, or 3, or 4, or 5, or 6, or 7, or 8 or more nucleotides in length. The specific nucleotides present in the gap sequence is not critical, so long as those nucleotides do not anneal to either the universal oligo or the first oligo of the target polynucleotide. Since G and C nucleotides are stronger hydrogen bonders that A and T nucleotides, in one aspect the gap sequence is formed from A and/or T nucleotides, at least predominantly. In FIGS. 12C and 12D, the gap sequence is represented by five "A" nucleotides.

In addition to this "gap sequence", each bridge oligo was designed and synthesized to contain a nucleotide sequence that complemented the nucleotide bases (17 of them, in this Example) present in the universal oligo that was immobilized to the solid support. In addition, the bridge oligo contains a nucleotide base sequence (16 bases in this Example) that is complementary a contiguous sequence of nucleotides in the first oligo of the target polynucleotide. As can be seen from FIGS. 12C and 12D, the 5 nucleotide "gap sequence" prevents ligation from occurring between the 3'OH from the universal oligo and the 5' phosphate of the first oligo.

All of the oligos, except for the bridge oligos, that were used in this gene assembly process were phosphorylated. They were synthesized and purified by HPLC by Metabion Company (Germany). The lyophilized oligos were all suspended in purified water (Millipore, Bedford, Mass., USA; @Millipore.com) at about 100 pmole/microliter concentration.

Gene Assembly on Solid Support

Sets of complementary oligos, either two or three members to a set, were combined and allowed to anneal to form double-stranded hybrids. The particular sets are shown and identified by the terms "0A", "1A", etc. in FIGS. 12E and 12F. The annealing process entailed combining the relevant oligos in 1×SSPE buffer at 65° C. for 15 min., which allowed the oligos to anneal to one another. The two bridge oligos "L" and "R" can be annealed to the solid support as a single strand oligo or can be annealed to their neighboring oligo duplex "3A" and "4A" respectively to form triplets prior to joining to the solid support. For those short oligos at the end of the gene, double-stranded triplets were made. As indicated in FIGS. 12E and 12F, the sets were each given a sequential name for ease of identification.

Solutions of the hybrids identified in FIGS. 12E and 12F were used in the following assembly process. About 75 microliter packed volume of solid support with a total of about 100 pmoles linker oligo coupled to it was added into the cartridge (Orochem Technologies, Westmont, Ill., USA) illustrated in FIG. 12G.

The storage buffer was removed and the support was washed with 0.4 ml of 2×SSPE buffer 3 times. The delivering of buffers and reagents was done via pipet tips and the removal of the buffers and reagents was done with a disposable syringe. It is important to pull the plunger before attaching the syringe to the cartridge to avoid dislocating the frits and loosing the solid support resins.

The fragments identified in FIG. 12E were assembled by sequential annealing 3A, 2A, 1A and 0A to solid support contained in the cartridge. Likewise, the fragments identified in FIG. 12F were assembled by sequential annealing 4A, 5A, 6A, 7A and 8A to solid support in a separate cartridge. The annealing process consisted of mixing 50 microliters 2×SSPE buffer and 400 pmoles of the duplex or triplex solution and gently shaking the cartridge at room temperature for 2 hours. Between each annealing cycle, a washing process consisting of treating the support with 0.4 ml refrigerated 2×SSPE five times, was used to remove any excess duplex.

After all the fragments were annealed together, the solid support was washed with 0.4 ml refrigerated 2×SSPE buffer five times, 0.4 ml refrigerated ligation wash buffer (50 mM Tris-HCl, 10 mM $MgCl_2$, 10 mM dithiothreitol, 25 µg/ml BSA, pH 7.5) twice and 100 microliter 1× ligation buffer (50 mM Tris-HCl, 10 mM $MgCl_2$, 10 mM dithiothreitol, 1 mM ATP, 25 µg/ml BSA, pH 7.5) once. The ligation reaction was carried out by adding 50 microliter 1× ligation buffer and 800 cohesive end units T4 DNA ligase (New England Biolabs, Beverly, Mass., USA; @neb.com) to the cartridge and gently shaking the cartridge at room temperature for 3 hours. Then the solid support was washed with 0.4 ml refrigerated 2×SSPE three times.

The ligated gene fragments were released from the solid support by repeatedly washing the solid support with 0.4 ml 50° C. deionized water. Typically, three washing cycles were sufficient to release all DNA from the solid support. The elute solution was combined and concentrated to 25 microliters by centrifuging in a YM-30 MicroCon Ultrafiltration device (Millipore).

A gel analysis was done to verify the size of the DNA fragments. A 6% native acrylamide gel was used with 1×TBE running buffer (89 mM Tris, 89 mM boric acid and 2 mM EDTA, pH 7.6). 2.5 Microliters of solution containing each fragment was mixed with 2 microliters of the loading dye (Gesura Type II 6×) and 40% sucrose mixture (1/1 v/v). The gel was run at a constant 150 volts and post stained with SYBR Gold (Molecular Probes, Eugene, Oreg., USA; @probes.com). The result is shown in FIG. 12H. In FIG. 12H, Lanes 1 and 4 are 20 bp marker sequences. Lane 2 is the left fragment (174 bp) and Lane 3 is the right fragment (196 bp). The gel confirmed that both the left and the right fragments had the correct sizes and were the major products. By the intensity of the image, estimated yield of both fragment products were 80-90 pmoles.

The final joining together of the left and right fragments was done in solution. The concentrated left and right fragment solutions were mixed with 5 microliters 10× ligation buffer and 800 cohesive units T4 DNA ligase. The ligation reaction was carried out at 37° C. for one hour followed by heating to 65° C. for 15 minutes. This process was repeated two more times each with a fresh dose of 400 units ligase. The product mixture was placed in a YM-30 MicroCon ultrafiltration device diluted with 400 microliters of 10 mM Tris/1 mM EDTA buffer. The solution was concentrated to less than 50 microliter. Then 400 microliters of deionized water was added and the solution was spun down to under 50 microliters. The latter process was repeated and the final product was retrieved in a 50 microliter solution. An aliquot of the product was analyzed on a 5% acrylamide gel, with the result shown in FIG. 12I. The image in FIG. 12I shows 4 bands: Lanes 1 and 2 are the final ligation product at different loading concentrations. Lane 3 is a 20 bp marker, and Lane 4 is a 100 bp marker. Lanes 1 and 2 show the final gene product (at 310 bp), unreacted left and right fragments with its bridge oligo (196 and 176 bp) and the annealed bridge oligos (60 bp). The final product was cloned and sequenced to verify that it had the desired sequence.

Example 2

Building a 240-Base Pair Gene on a Porous Polyethylene Support

Couple Linker Oligo to Polyethylene Frits by Carbodiimide.

Polyethylene frits of 9 mm diameter and 1.5 mm thickness with 7 and 20 micron pore size were purchased from Orochem Technologies (Westmont, Ill., USA; @orochem.com). Primary amine groups were introduced onto the surface of the PE frits by a plasma process performed by $4^{th}$ State Inc. (Belmont, Calif., USA; @4thstate.com). All subsequent reactions and processes involving frits were carried out in a polypropylene cartridge as depicted in FIG. 12G (also purchased from Orochem Technologies). The frit is held in place by friction with the walls of the container.

Reagent and buffers are delivered to the frit from the top of the cartridge, mixed through the pores of the frit by a syringe pumping the liquid up and down through the frit, and removed from the frit by an empty syringe. The bottom opening of the cartridge is plugged during the reaction. Before coupling the linker oligo to the frit, the frit was succinylated by placing the frit in a 10% succinic anhydride in 0.1 M sodium acetate (pH 4.5) solution for 17 hours at room temperature. The succinylated frit was washed with water at room temperature, followed by 0.1 M sodium acetate (pH 6-7) once at 45° C. and twice at room temperature, and finally with water three times at room temperature.

The succinylated polyethylene frits were then coupled to the 17 nucleotide linker oligonucleotide containing a poly (ethylene glycol) (n=12) spacer at its 5'-end terminating with a primary amine (prepared by Trilink Biotechnologies, Inc.). Each frit was placed into 50 µl of 0.1 M morpholinoethanesulfonic acid (MES) at pH 4.5 with a linker oligonucleotide concentration of 6 µM and an ethyldimethylaminopropyl carbodiimide hydrochloride (EDC) concentration of 0.4 M at room temperature for 3 hours. After the reaction, the frit was washed six times with a wash buffer (0.3 M sodium chloride, 10 mM Tris, 1 mM EDTA and 0.1% sodium dodecyl sulfate, pH 8) and twice with 2×SSPE (0.3 M sodium chloride, 20 mM sodium phosphate, 2 mM EDTA, pH 7.6). The frits are stored in 2×SSPE at 4° C.

Hybridization Capacity Assay by Fluorescence

In order to determine the capacity of the frit to anneal to oligonucleotides, the following assay was conducted. A polyethylene frit coupled to the linker oligonucleotide was combined with a solution of fluorescently-labeled oligonucleotide having a nucleotide sequence complementary to the nucleotide sequence of the linker oligonucleotide. The frit was then washed to remove excess (non-hybridized) complementary oligo. The frit was then exposed to conditions that eluted the hybridized complementary oligos, and the fluorescence signal from the eluted solution was measured.

The annealing reaction (with the complementary oligonucleotide) was carried out in 2×SSPE at room temperature for two hours. Washing was done with 2×SSPE and the completeness of the washing was monitored by fluorescence. The hybridized fluorescently-labeled oligonucleotide was eluted from the frits by 1 ml 50° C. Millipore water three times. Over 95% of the fluorescence signal was obtained from the first elution. Comparison to a standard calibration of solutions of known amounts of the labeled complimentary oligo allowed a determination that the hybridization capacity for the 7 um pore frit is 170 pmoles/frit, and the hybridization capacity for the 20 um pore frit is 175 pmoles/frit.

Gene Assembly on Polyethylene Frits

The target gene has 240 base pairs including a 5 base overhang on one end and a 17 base overhang on the other end, as illustrated in FIG. 13A.

As with the experiment described in Example 1, and as illustrated in FIG. 13B, this target gene was "cut" into a family of oligos having 33-35 bases for the interior oligos and shorter sequences at the ends. Each interior oligo overlaps with two complimentary oligos over a span of 15-17 nucleotides, and the end oligos overlap with one complimentary oligo over a span of 15-16 nucleotides. A bridge oligo marked with **** was designed to be added to the left end of the gene. The bridge oligo does not have a phosphate at the 5' end so it does not participate in the ligation of the gene. The overhang region of the bridge oligo has 17-base sequence that compliments the linker oligo on the polyethylene frits.

All of the oligos used in this gene assembly were synthesized by the well know phosphoamidite chemistry on a commercial automatic synthesizer (ABI) and phosphorylated by kinase. After the oligos were synthesized, they were annealed to form doublets or triplets at 15-25 pmole/µl in 1×SSPE buffer at 65° C. for 15 min. The exact arrangement of the doublets and triplets for this gene is illustrated below. They were each given a sequential name for ease of identification. The solution containing the doublet- or triplet-fragments was allowed to cool to room temperature by itself. The fragments are identified by codes ranging from 1A to 6A in FIG. 13C. These fragment-containing solutions were used in the following assembly process.

A single piece of polyethylene frit coupled with the linker oligo was placed in the cartridge. The storage buffer was removed and the frit was washed with 0.4 ml of 2×SSPE buffer 3 times. The first oligo triplex 1A, 300 pmoles total, was added to the frit with 50 µl 6×SSPE buffer. The solution was pumped up and down through the frit by a syringe. The annealing was carried out for 1 hour and 30 minutes. A 2×SSPE wash (0.5 ml, five times) followed the annealing step to remove unhybridized oligo triplet. This process was sequentially repeated for oligo doublets 2A, 3A, 4A, 5A and finally for triplet 6A.

After all the oligos for the gene were annealed together, the frit was washed with 0.4 ml refrigerated ligation wash buffer (50 mM Tris-HCl, 10 mM $MgCl_2$, 10 mM dithiothreitol, 25

μg/ml BSA, pH 7.5) once and 100 microliter 1× ligation buffer (50 mM Tris-HCl, 10 mM MgCl$_2$, 10 mM dithiothreitol, 1 mM ATP, 25 μg/ml BSA, pH 7.5) once. The ligation reaction was carried out by adding 50 microliter 1× ligation buffer and 800 cohesive end units T4 DNA ligase (New England Biolabs) to the cartridge and mixing the reaction content by pumping the solution up and down at room temperature for 3 hours using a syringe. Then the frit was washed with 0.5 ml 6×SSPE three times and 0.5 ml 2×SSPE three times.

The ligated gene was released from the frit by washing the frit with 0.4 ml 50° C. Millipore water three times. The eluted solutions were combined and concentrated to about 20 microliters by centrifuging in a YM-30 MicroCon Ultrafiltration device (Millipore).

A gel analysis was done to verify the size of the DNA fragments. A 5% pre-cast native acrylamide gel (Bio-Rad Laboratories, Hercules, Calif., USA; @bio-rad.com) was used with 1×TBE running buffer (89 mM Tris, 89 mM boric acid and 2 mM EDTA, pH 7.6). The gel was run at a constant 160 volts and post stained with SYBR Gold (Molecular Probes). The result (FIG. 13D) confirmed that the expected gene fragment with the correct size was the major product. The sample in the left lane in FIG. 13D is a 200 bp ladder. The sample in the right lane is the assembled product mixture.

Example 3

Comparing Solid Phase Gene Assembly on Solid Support With and Without PEG Spacer Separate batches of aminomethylated polystyrene resin were coupled to two different linker oligos. One linker oligo contained a PEG spacer (n=24) between the terminal amine group and the oligonucleotide (17b oligonucleotide-PEG (n=24)-NH$_2$). The other linker oligo did not contain any spacer and had carboxylic acid termination (17b oligonucleotide-COOH) where both oligos were obtained from Trilink. The oligo with PEG spacer was coupled to the polystyrene support using the coupling method described in Example 1. The linker oligo without a spacer was coupled to a different batch of the same polystyrene support and also to polyethylene frits using the carbodiimide method described next.

Before coupling, 150 ul packed volume of polystyrene resin was washed with 1 ml 0.1 M pH 4.5 morpholinepropane sulfonic acid (MOPS) twice. The coupling reaction was carried out with 3 μl carboxy function containing oligo (1 nmole/μl) and 20 μl EDC solution (26.6 mg EDC in 500 μl Millipore water) in 100 μl 0.1 M pH 4.5 MOPS at room temperature for 1.5 hours. After the reaction, the resin was washed 450 μl 0.5 M borate/0.25 M sodium chloride five times. The residual amines were capped with acetic anhydride by mixing with 300 μl mixture of acetic anhydride/N-methylpyrrolidinone/0.5 M borate, (8/2/2 v/v/v) at room temperature for 1.3 hours. The resin was then washed three times with a mixture containing 50/50 (v/v) N-methylpyrrolidinone/1 mM EDTA, three times with 1 mM EDTA (pH 8), twice with a wash buffer (0.3 M sodium chloride, 10 mM Tris, 1 mM EDTA and 0.1% sodium dodecyl sulfate, pH 8) and five times with 10 mM Tris/1 mM EDTA (pH 8).

The hybridization capacity of both polystyrene resins was assayed by the molecular beacon method described in Example 1. They were both at about 0.7 pmole/pl packed resin. The hybridization capacity of the polyethylene frit was assayed by the method described in Example 2. It was determined to be 84 pmoles per frit.

Assemble a 134 Base-pair Gene

Analogously to the approach described in Example 1, the target gene was "cut" into a series of oligos, each having 30-33 nucleotide bases. A shorter sequence of 22 bases was placed at the end of the bottom strand. Each interior oligo overlapped with two complementary oligos over a span of 15-18 nucleotide bases. As shown in FIG. 14A, the first oligo in the top strand is labeled with a fluorescent group FAM (◉) at its 5' end. A bridge oligo marked with **** was added to the left end of the gene. The bridge oligo does not have a phosphate at the 5' end so it does not participate in the ligation of the gene. Also, the bridge oligo is fluorescently labeled at its 3' end.

Fluorescently-labeled oligos were synthesized by Trilink Inc. All other oligos were synthesized by the well know phosphoamidite chemistry on a commercial automatic synthesizer. All single-stranded oligonucleotides were annealed to form either doublets or triplet hybrids at 25-30 pmole/μl in 1×SSPE buffer at 65° C. for 15 min. The exact arrangement of the doublets and triplets for this gene is illustrated in FIG. 14B. They were each given a sequential name for ease of identification. The solution containing the hybrids was allowed to cool to room temperature by itself. These hybrid solutions were used in the following assembly process.

Into each fritted polypropylene cartridge was placed 100-150 μl packed solid support coupled with linker oligo. In the case of the polyethylene frit, the oligo coupled frit was directly placed into the cartridge instead of using untreated (virgin) frit. The storage buffer was removed and the support was washed with 0.4 ml of 2×SSPE buffer 3 times. The first oligo triplex 0A, 200 pmoles total, was added to each support with 50 μl 6×SSPE buffer. The annealing mixture was vortexed at room temperature for 1 hour 45 minutes. A 6×SSPE wash (0.4 ml, five times) followed the annealing reaction to remove unhybridized oligo triplet. The process was repeated for oligo doublets 1A, 2A and 3A sequentially, each with an annealing time of 1 hour at room temperature.

After all the oligos for the gene were annealed together, the solid support contained in the cartridge was washed twice with 0.4 ml refrigerated ligation wash buffer (50 mM Tris-HCl, 10 mM MgCl$_2$, 10 mM dithiothreitol, 25 μg/ml BSA, pH 7.5) and 50 μl 1× ligation buffer (50 mM Tris-HCl, 10 mM MgCl$_2$, 10 mM dithiothreitol, 1 mM ATP, 25 μg/ml BSA, pH 7.5) once. The ligation reaction was carried out by adding 50 μl 1× ligation buffer and 800 cohesive end units T4 DNA ligase (New England Biolabs) to the cartridge and mixing the reaction content by pumping the solution up and down at room temperature for 3 hours. Then the support was washed with 0.5 ml 2×SSPE 5 times.

The ligated gene was released from the support by washing the support with 0.4 ml 50° C. Millipore water three times. The eluted solutions were combined and concentrated to about 20 microliters by centrifuging in YM-30 MicroCon Ultrafiltration device (Millipore). A gel analysis was done to verify the size of the DNA fragments.

An 8% native acrylamide gel was used with 1×TBE running buffer (89 mM Tris, 89 mM boric acid and 2 mM EDTA, pH 7.6). The gel was run at a constant 175 volts and imaged before and after staining with SYBR Gold (Molecular Probes). The gel images are shown below in FIGS. 14C and 14D, where the lane assignments are: (1) gene built on polystyrene support coupled with linker oligo that contain a PEG spacer; (2) gene built on polyethylene frit coupled with linker oligo without any spacers; (3) gene built on polystyrene support coupled with linker oligo without spacers; (4) 20 bp ladder (Gensura). FIG. 14C shows the gel before staining, and FIG. 14D shows the gel after staining.

Before and after staining, the images are consistent. Product built on solid support with a spacer showed as the most intensive band in the product mixture (lane 1). Product built on the same type of support without a spacer failed in the assembly process with a very intensive band of the FAM labeled bridge oligo between 20 and 40 bp position (Lane 3). The gene built on polyethylene frit (Lane 2) is similar to the bands in Lane 1 except that the overall intensity is rather low.

Example 4

Comparison with Different Overhand Sizes

A polystyrene sphere solid support coupled with a linker oligo that contained a PEG (n=6) spacer was used for this example. The coupling method was the same as described in Example 1. The solid support had a hybridization capacity of 1 pmole/µl packed resin.

Oligonucleotide Design

A target gene of 134 base-pairs was designed to be built from two different sets of oligonucleotides. One set had long over hangs, in the range of 15-18 bases (see FIG. 15A). The other set had short overhangs of only 4 bases (see FIG. 15B). In each set, the first top strand had a fluorescent group (FAM, ⊛) on the 5' end and the bridge oligo had a FAM group on the 3' end.

All FAM-labeled oligos were made by Trilink Inc. All of the oligos used in the long overhang set were synthesized and phosphorylated on a commercial oligonucleotide synthesizer (Beckman). All of the oligos used in the short overhang set were prepared and phosphorylated by Life Technologies Inc.

Gene Assembly of 17-Base Overhang Oligonucleotide on Solid Support

Each of the top strand oligonucleotide was annealed to a separate complementary bottom strand oligonucleotide to form duplexes in 1×SSPE buffer at 65° C. for 15 min. The bridge oligo was annealed with the first duplex to form a triplet. The resulting fragments are identified in FIG. 15C.

To join the fragments together, about 120 microliter packed volume of solid support with a total of about 100 pmoles linker oligo coupled to it was washed with 1 ml of 2×SSPE buffer 3 times. The first oligo triplet (0A, 400 pmoles total) was added to the support with 100 µl 2×SSPE buffer. The annealing mixture was vortexed at room temperature for 2 hours. A 2×SSPE wash (0.4 ml, five times) followed the annealing process in order to remove unhybridized oligo triplet. This process was repeated for oligo doublets 1A, 2A and 3A sequentially, each with an annealing time of 2 hours at room temperature and a 2×SSPE wash (0.4 ml, five times).

After all the oligo duplexes for the gene were annealed together, the solid support was washed three times with 1 ml refrigerated ligation wash buffer (50 mM Tris-HCl, 10 mM MgCl$_2$, 10 mM dithiothreitol, 25 µg/ml BSA, pH 7.5) and 90 µl 1× ligation buffer (50 mM Tris-HCl, 10 mM MgCl$_2$, 10 mM dithiothreitol, 1 mM ATP, 25 µg/ml BSA, pH 7.5) three times. The ligation reaction was carried out by adding 70 µl 1× ligation buffer and 800 cohesive end units T4 DNA ligase (New England Biolabs) to the cartridge and mixing the reaction content by vortexing at room temperature for 2 hours. Then the support was washed with 1 ml wash solution (0.3 M sodium chloride, 10 mM Tris, 1 mM EDTA and 0.1% sodium dodecyl sulfate, pH 8) 5 times. The ligated gene was released from the support by washing the support with 0.4 ml 50° C. Millipore water three times. The elute solutions were combined and concentrated to about 20 microliters by centrifuging in YM-30 MicroCon Ultrafiltration device (Millipore).

Gene Assembly of 4-Base Overhang Oligonucleotide on Solid Support

All the top strand oligonucleotide was annealed to one complementary bottom strand oligonucleotide to form a duplex in 1×SSPE buffer at 65° C. for 15 min. The bridge oligo was annealed with the first triplet to form a tetrad. The resulting fragments are identified in FIG. 15D.

About 110 microliter packed volume of solid support with a total of about 100 pmoles linker oligo coupled to it was washed with 1 ml of 2×SSPE buffer 3 times. The bridge oligo (350 pmoles) in 100 µl 2×SSPE buffer was annealed to the solid support at room temperature during 1 hour. Then quadruplet 0A/1A (400 pmoles total, 31 pmole/µl) was added. The annealing mixture was vortexed at room temperature for 1 hour 40 min. A 2×SSPE wash (0.4 ml, four times) followed the annealing step to remove unhybridized oligos. The annealed oligos were ligated with 100 cohesive end units T4 DNA ligase in presence of 100 µl 1× ligation buffer at room temperature for 2 hours. The ligated product on the solid support was washed with 2×SSPE (0.4 ml, 5 times).

The annealing and ligation process was repeated for oligo doublets 2A, 3A and 4A sequentially. Before starting the annealing and ligation of a new duplex, a small amount of the solid support was removed as a sample for each ligation product. After the last duplex was annealed and ligated, the products, including the small sample withdrawn after each cycle, were eluted with 400 µl 55° C. water three times. The eluted solutions were combined and concentrated to about 50-60 microliters by centrifuging in YM-30 MicroCon Ultrafiltration device (Millipore).

Gel Analysis

A gel analysis was done to verify the size of the DNA fragments. A 8% native acrylamide gel was used with 1×TBE running buffer (89 mM Tris, 89 mM boric acid and 2 mM EDTA, pH 7.6). 6-7 microliters of the each fragment was mixed with 3 microliters of the loading dye (Gesura Type II 6X) and 40% sucrose mixture (1/1 v/v). The gel was run at a constant 150 volts and post stained with SYBR Gold (Molecular Probes). The resulting gel is shown in FIG. 15E. In FIG. 15E, Lanes 1 and 2 show the 17-base overhang assembly product. Lanes 3 and 7 are a 20 bp marker. Lanes 4-6 show the 4-base overhang assembly product after ligation of 2A (see Lane 4), after ligation of 3A (see Lane 5) and after ligation of 4A (see Lane 6).

The result confirmed the production of the correct sized gene of 145 bp from both oligo sets. However the 17-base overhang set only produced one major product while the 4-base overhang oligo set produced products of all three ligation cycles.

Example 5

Re-Use the Solid Support Coupled with a Generic Linker Oligo

Generally, solid supports coupled with a generic linker oligonucleotide described in this invention are re-usable. After one gene is assembled and eluted off from the solid support, the support may be washed with Millipore water and then 2×SSPE, and stored at 4° C. in purified water. The support can be used again to assemble another gene. Such process can be repeated multiple times.

A 355 bp gene was assembled using the same procedure described in Example 1. A "left" and a "right" fragment were separately assembled on two different polystyrene resin supports and then combined to make the final gene. The assembly was compared using freshly prepared solid support and previously used/cleaned support. The amounts of reagents used in both cases were identical. Eluted fragments were analyzed on 6% acrylamide gel, as shown in FIG. 16. In FIG. 16, lanes 1 and 6 are 20 bp ladder, lane 3 is the right fragment (169 bp including the long overhang sequence) assembled on previously used support, lane 5 is the right fragment assembled on fresh support, lane 2 is the left fragment assembled on previously used support and stopped after 4 annealing cycles (166 bp), and lane 4 is the left fragment assembled on fresh support after 6 annealing cycles (230 bp). The gel demonstrates that a previously used support can produce the same quality and yield of polynucleotide as a fresh support.

Example 6

Building a 425-Base Pair Gene on Porous Polyethylene Support

Couple Linker Oligo to Polyethylene Frits by Carbodiimide.

Polyethylene frits of 9 mm diameter and 1.5 mm thick with 7 and 20 micron pore size were purchased from Orochem Technologies (Westmont, Ill.). Primary amine groups were introduced to the surface of the PE frits by a plasma process by $4^{th}$ State Inc. All subsequent reactions and processes involving frits were carried out in a polypropylene cartridge (also purchased from Orochem Technologies) as illustrated in FIG. 12G. Reagent and buffers were delivered to the frits from the top of the cartridge, mixed through the pores of the frit by a syringe pumping the liquid up and down and removed from the frit by an empty syringe. The bottom opening of the cartridge is plugged during the reaction.

Before coupling to an oligonucleotide, the frits were succinylated in 10% succinic anhydride in 0.1 M sodium acetate (pH 4.5) for 17 hours at room temperature. The succinylated frits were washed with water at room temperature, then 0.1 M sodium acetate (pH 6-7) once at 45° C. and twice at room temperature and, finally with water three times at room temperature. The succinylated polyethylene frits were then coupled to a 17 base linker oligonucleotide containing a 5' poly(ethylene glycol) (m=12 in formula (1)) spacer and a terminal primary amine ($R^1$=amino in formula (1)), as prepared by Trilink Biotechnologies, Inc. The coupling was done in 50 μl volume per piece of frit in 0.1 M morpholinoethanesulfonic acid (MES) at pH 4.5 with a linker oligonucleotide concentration of 6 μM and EDC concentration of 0.4 M at room temperature for 3 hours. After the reaction, the frit was washed six times with a wash buffer (0.3 M sodium chloride, 10 mM Tris, 1 mM EDTA and 0.1% sodium dodecyl sulfate, pH 8) and twice with 2×SSPE (0.3 M sodium chloride, 20 mM sodium phosphate, 2 mM EDTA, pH 7.6). The frits were stored in 2×SSPE at 4° C.

Hybridization Capacity Assay by Fluorescence

The assay was carried out by annealing the polyethylene frits coupled with the linker oligonucleotide to a fluorescently labeled complementary oligonucleotide, washing the frits to remove excess complementary oligos, eluting the hybridized oligo and measuring the fluorescence of the eluted solution, in analogy to the process described in Example 1. The annealing was carried out in 2×SSPE at room temperature for two hours. Washing was done with 2×SSPE and the completeness of the washing was monitored by fluorescence. The hybridized fluorescently-labeled oligonucleotides were eluted from the frits using 1 ml 50° C. Millipore water three times. Over 95% of the fluorescence signal was from the first elution. By comparison to a standard calibration of the labeled complimentary oligo, the hybridization capacity for the 7 μm pore frit was determined to be 170 pmoles/frit and that for the 20 μm pore frit was determined to be 175 pmoles/frit.

Gene Assembly on Polyethylene Frits

The target gene has 425 base pairs including a 17 base overhang at both 5' ends, as generally illustrated in FIG. 17A.

In analogy to the process described in Example 1, this 425 bp polynucleotide was cut into a set of 24 oligos, each having a sequence length of 33-35 nucleotide bases, as illustrated in FIG. 17B. The oligos overlapped with oligos in the complementary strand, with overlaps of 16-17 bases as described in earlier Examples. A bridge oligo (marked with ****) which has a nucleotide sequence complementary to both the left 5' overhang of the gene and the linker oligo on the solid support, was designed for use in the gene assembly. The bridge oligo did not have a phosphate group at its 5' end so it could not participate in any ligation reactions. The bride oligo merely acts as a removable splint between the gene and the solid support. All the oligos used in this gene assembly were synthesized by the well know phosphoamidite chemistry on a commercial automatic synthesizer (ABI) and phosphorylated by kinase.

To begin the synthesis process, all single-stranded oligonucleotides were annealed to duplex at 19 pmole/μl in 1×SSPE buffer at 65° C. for 15 min. The exact arrangement of the doublet and triplet hybrids for this gene is illustrated below in FIG. 17C. They were each given a sequential name for ease of identification. The solutions containing the hybrids were allowed to cool to room temperature. These hybrid-containing solutions are used in the following assembly process.

A single piece of polyethylene frit coupled with the linker oligo was placed in the cartridge. The storage buffer was removed and the frit was washed with 0.4 ml of 2×SSPE buffer 3 times. The first oligo (triplet 1A, 300 pmoles total) was added to the frit with 50 μl 6×SSPE buffer. The solution was pumped up and down through the frit by a syringe. The annealing was carried out for 1 hour and 30 minutes. A 2×SSPE wash (0.5 ml, five times) followed the annealing process in order to remove unhybridized oligo triplet. The process was repeated for oligo hybrid 2A to 12A sequentially, except that the annealing time was reduced to one hour.

After all the oligos for the gene were annealed together, the frit was washed with 0.4 ml refrigerated ligation wash buffer (50 mM Tris-HCl, 10 mM $MgCl_2$, 10 mM dithiothreitol, 25 μg/ml BSA, pH 7.5) once and 100 microliter 1× ligation buffer (50 mM Tris-HCl, 10 mM $MgCl_2$, 10 mM dithiothreitol, 1 mM ATP, 25 μg/ml BSA, pH 7.5) once. The ligation reaction was carried out by adding 50 microliter 1× ligation buffer and 1200 cohesive end units T4 DNA ligase (New England Biolabs) to the cartridge and mixing the reaction content by pumping the solution up and down at room temperature for 3 hours. Then the frit was washed with 0.5 ml 6×SSPE five times and 0.5 ml 2×SSPE once.

The ligated gene was released from the frit by washing the frit with 0.4 ml 50° C. Millipore water three times. The eluted solutions were combined and concentrated to about 20 microliters by centrifuging in a YM-30 MicroCon Ultrafiltration device (Millipore). A gel analysis was done to verify the size of the DNA fragments. A 5% pre-cast native acrylamide gel (BioRad) was used with 1×TBE running buffer (89 mM Tris, 89 mM boric acid and 2 mM EDTA, pH 7.6). The gel was run at a constant 130 volts and post stained with SYBR Gold (Molecular Probes). The result, shown in FIG. 17D with a 100 bp ladder, confirmed that the expected gene fragment with the correct size was one of the major products.

A polymerase chain reaction (PCR) was carried out on the final gene fragment using the first of the top strand oligo and the last of the bottom strand oligo as primers. The PCR product was also analyzed by 5% acrylamide gel, with the result being shown in FIG. 17E. The left lane was the PCR product of the assembled gene fragment. The center lane was a PCR control sample of about 520 bp. The right lane is a 100 bp marker. The 425 mer fragment is clearly shown on the gel.

Example 7

Synthesis of a 1 Kb Gene Fragment

The model gene we built is an *E. coli* Lac repressor gene (LacI) of 1199-bp. The construction of this model gene is shown in the flow chart in FIG. 18. Three intermediate gene fragments, each about 400 bp, were prepared on a solid support. The final 1.2 kb gene was assembled using solution based technology. Oligos are synthesized on a commercial oligo-synthesizer in house.

The solid support was polyethylene frits of 7-20 micron pore size and the reactor housing was a polypropylene SPE cartridge. Both the frits and the cartridge were purchased from Orochem Inc. (Westmont, Ill.). The surface of the frits was derivatized by plasma treatment at 4th State Inc. (Belmont, Calif.). A universal linker oligo of 17 nucleotides was coupled to a PEG spacer at its 5' end and terminated with a primary amine group. This linker oligo was covalently linked to the solid support by aqueous phase carbodiimide chemistry. The binding capacity of the solid support was determined by the fluorescence assay described elsewhere herein.

Each intermediate fragment construct consisted of 12 pairs of oligos. They were assembled separately on solid support by 12 repeated annealing-washing cycles. The annealed fragments were ligated by T4 DNA ligase. The gene fragments were released from the solid support by eluting with warm water. Their sizes were confirmed by polyacrylamide gel electrophoresis. The entire cycle time to assemble the 400 bp fragments manually was 18 hours.

The intermediate fragments were amplified by PCR to generate cleaner product and to increase quantity of material for later process. The final gene assembly was done in solution phase by yeast homologous recombination technique (K. Oldenburg, K. Vo, S. Michaelis and C. Paddon, *Nuclei Acid Research*, (1997), vol. 25, 451-452; and P. Gunyuzlu, G. Hollis and J. Toyn, *Biotechniques*, (2001), vol. 31, 1246-1250). The final assembled gene was cloned and sequenced. Of the six full size clones examined, each contained 4-5 random single nucleotide errors, which can be corrected. This error rate and type are comparable to those found in solution phase assembled genes of similar size (data not included). Upon sequencing one of the 400 bp intermediate fragments it was discovered that 4 correct sequences were obtained from 10 clones. The errors were again random and mostly single nucleotide substitution, deletion or insertion.

Example 8

Synthesis of a 1 Kb Gene Gragment Using Automated Solid Phase Gene Assembly Station In a similar process as described above in Example 1-4 and 6, the constituent gene fragments from the target 1 kb gene in Example 7 were assembled using the automated solid phase gene assembly station (device) of this invention.

The target 1 kb gene was divided into six gene fragments (Fr1, Fr2, Fr3, Fr4, Fr5 and Fr6), each between 180-240 bp long. These six fragments were simultaneously assembled on 6 individual reaction vessels contained inside the reaction block.

The process executed on the automated device includes derivatizing the solid support, coupling of the universal linker oligonucleotide, assaying the universal linker oligonucleotide hybridization capacity, assemblying gene fragment, enzymatic ligation and finally removing the gene fragment from the solid support. The entire process was pre-programmed and operated by the computer control unit. The bridge oligonucleotide and sequential oligonucleotide duplexes for each fragment were contained and sealed in one 96-well microtiter plate positioned on the microtiter plate holding apparatus, which was kept at 4° C. The reaction block maintained the temperature required for each step of the process. The eluted gene fragments were visualized by acrylamide gel electrophoresis as indicated in FIG. 19. All fragments shows correct size when compared to the ladder.

All of the above U.S. patents, U.S. patent application publications, U.S. patent applications, foreign patents, foreign patent applications and non-patent publications referred to in this specification and/or listed in the Application Data Sheet are incorporated herein by reference, in their entireties.

From the foregoing, it will be appreciated that, although specific embodiments of the invention have been described herein for purposes of illustration, various modifications may be made without deviating from the spirit and scope of the invention. For example, the methods, compounds and compositions of the present invention may be used in solid-phase DNA synthesis, and/or automated chemical DNA synthesis, where genes are preferred DNA molecules.

What is claimed is:

1. A method of preparing a double-stranded polynucleotide product in solution, comprising the following steps:
   (a) providing a partially double-stranded polynucleotide coupled to a solid support, wherein the partially double-stranded polynucleotide coupled to the solid support comprises an universal oligonucleotide and a bridge oligonucleotide, wherein one end of the universal oligonucleotide is coupled to the solid support and the other end of the universal oligonucleotide is non-reactive under ligating conditions and wherein the universal oligonucleotide is annealed to a portion of the bridge oligonucleotide;
   (b) contacting a solution of a first single-stranded polynucleotide or a first partially double-stranded polynucleotide, both of which are at least partially complementary to the portion of the bridge oligonucleotide that is not annealed to the universal oligonucleotide, with the partially double-stranded polynucleotide coupled to the solid support of part (a);
   (c) passing the solution of part (b) in one direction by the partially double-stranded polynucleotide coupled to the solid support of part (a) at a rate of flow to allow for the single-stranded polynucleotide or the partially double-stranded polynucleotide in the solution of part (b) to anneal to the portion of the bridge oligonucleotide that is not annealed to the universal oligonucleotide;
   (d) passing the solution of part (b) in an opposite direction from the previous direction by the partially double-stranded polynucleotide coupled to the solid support of part (a) at a rate of flow in order to allow for the first single-stranded polynucleotide or the first partially double-stranded polynucleotide in the solution of part (b) to anneal to the portion of the bridge oligonucleotide that is not annealed to the universal oligonucleotide; and (e) repeating part (d) multiple times as needed to form a first intermediate duplex coupled to the solid support wherein at least 80% of the first single-stranded polynucleotide or the first partially double-stranded polynucleotide in the solution of part (c) anneals to the portion of the bridge oligonucleotide that is not annealed to the universal oligonucleotide and wherein the first intermediate duplex comprises a nucleotide region that is not annealed to the bridge oligonucleotide;

(f) contacting the first intermediate duplex with a solution of a second single-stranded polynucleotide or a second partially double-stranded polynucleotide, both of which are at least partially complementary to the nucleotide region of the first intermediate duplex that is not annealed to the bridge oligonucleotide;

(g) passing the solution of part (d) in one direction by the first intermediate duplex at a rate of flow to allow for the second single-stranded polynucleotide or the second partially double-stranded polynucleotide in the solution of part (f) to anneal to the first intermediate duplex;

(h) passing the solution of part (f) in an opposite direction from the previous direction by the first intermediate duplex at a rate of flow in order to allow for the second single-stranded polynucleotide or the second partially double-stranded polynucleotide in the solution of part (f) to anneal to first intermediate duplex; and (i) repeating part (h) multiple times as needed to form a second intermediate duplex wherein at least 80% of the second single-stranded polynucleotide or the second partially double-stranded polynucleotide in the solution of part (f) anneals to the nucleotide region of the first intermediate duplex that is not annealed to the bridge oligonucleotide and wherein the second intermediate duplex comprises a nucleotide region that is not annealed to the first intermediate duplex;

(j) repeating steps (b) through (e) as needed to form a final annealed polynucleotide product coupled to the solid support;

(k) exposing the final annealed polynucleotide product to ligating conditions and denaturing conditions to provide the double-stranded polynucleotide product, wherein the universal oligonucleotide does not form part of the double-stranded polynucleotide product.

2. The method of claim 1 wherein the solution of part (b) is a solution of a partially double-stranded polynucleotide.

3. The method of claim 1 wherein the solution of part (b) passes by the partially double-stranded polynucleotide coupled to the solid support of part (a) at a constant rate of flow.

4. The method of claim 1 wherein the solution of part (b) passes by the partially double-stranded polynucleotide coupled to the solid support of part (a) at a variable rate of flow.

5. The method of claim 1 wherein the solid support is porous.

6. The method of claim 5 wherein the solution of part (b) is required to pass through the pores of the solid support multiple times.

* * * * *